United States Patent
Lupher, Jr. et al.

(10) Patent No.: US 9,884,899 B2
(45) Date of Patent: Feb. 6, 2018

(54) METHODS FOR TREATING FIBROSIS USING CRP ANTAGONISTS

(75) Inventors: Mark L. Lupher, Jr., Chester Springs, PA (US); Teresa K. Surowy, Kenosha, WI (US); Shawn Li, Exton, PA (US); David Paul Hesson, Malvern, PA (US); Michael Scott Kramer, Harleysville, PA (US)

(73) Assignee: Promedior, Inc., Lexington, MA (US)

( * ) Notice: Subject to any disclaimer, the term of this patent is extended or adjusted under 35 U.S.C. 154(b) by 432 days.

(21) Appl. No.: 12/215,700

(22) Filed: Jun. 27, 2008

(65) Prior Publication Data
US 2009/0202520 A1  Aug. 13, 2009

Related U.S. Application Data

(60) Provisional application No. 60/958,634, filed on Jul. 6, 2007.

(51) Int. Cl.
*A61K 39/395* (2006.01)
*C07K 14/47* (2006.01)
*G01N 33/68* (2006.01)

(52) U.S. Cl.
CPC ..... *C07K 14/4737* (2013.01); *G01N 33/6887* (2013.01); *G01N 2333/4709* (2013.01); *G01N 2333/4737* (2013.01); *G01N 2800/085* (2013.01); *G01N 2800/382* (2013.01)

(58) Field of Classification Search
None
See application file for complete search history.

(56) References Cited

U.S. PATENT DOCUMENTS

| | | | |
|---|---|---|---|
| 4,233,969 A | 11/1980 | Lock et al. | |
| 4,556,056 A | 12/1985 | Fischer et al. | |
| 4,782,014 A * | 11/1988 | Serban et al. | 435/7.95 |
| 5,092,876 A | 3/1992 | Dhawan et al. | |
| 5,272,258 A * | 12/1993 | Siegel et al. | 530/388.25 |
| 5,591,709 A | 1/1997 | Lindenbaum | |
| 5,654,186 A | 8/1997 | Cerami et al. | |
| 5,698,589 A | 12/1997 | Allen | |
| 5,750,345 A * | 5/1998 | Bowie | 435/6 |
| 5,804,446 A | 9/1998 | Cerami et al. | |
| 5,846,796 A | 12/1998 | Cerami et al. | |
| 5,989,811 A * | 11/1999 | Veltri et al. | 435/6 |
| 6,037,458 A | 3/2000 | Hirai et al. | |
| 6,054,121 A | 4/2000 | Cerami et al. | |
| 6,071,517 A | 6/2000 | Fanger et al. | |
| 6,126,918 A | 10/2000 | Pepys et al. | |
| 6,174,526 B1 | 1/2001 | Cerami et al. | |
| 6,365,570 B1 | 4/2002 | Van Kessel et al. | |
| 6,406,698 B1 | 6/2002 | Svehang et al. | |
| 6,537,811 B1 | 3/2003 | Freier | |
| 6,600,019 B2 | 7/2003 | Prayaga et al. | |
| 6,660,843 B1 | 12/2003 | Feige et al. | |
| 6,872,541 B2 | 3/2005 | Mills | |
| 7,666,432 B2 | 2/2010 | Gomer et al. | |
| 7,763,256 B2 | 7/2010 | Gomer et al. | |
| 8,012,472 B2 * | 9/2011 | Gomer et al. | 424/130.1 |
| 8,057,802 B2 * | 11/2011 | Gomer et al. | 424/198.1 |
| 8,187,599 B2 | 5/2012 | Gomer et al. | |
| 8,187,608 B2 * | 5/2012 | Gomer et al. | 424/198.1 |
| 8,247,370 B2 * | 8/2012 | Pelura | 514/1.1 |
| 8,329,659 B2 * | 12/2012 | Willett | 514/20.9 |
| 8,497,243 B2 | 7/2013 | Hesson et al. | |
| 2002/0058284 A1 | 5/2002 | Winkel | |
| 2003/0003567 A1 | 1/2003 | Barber et al. | |
| 2003/0022245 A1 | 1/2003 | Mills | |
| 2003/0162180 A1 * | 8/2003 | Pricop | 435/6 |
| 2004/0068095 A1 | 4/2004 | Shimkets et al. | |
| 2004/0121343 A1 * | 6/2004 | Buechler et al. | 435/6 |
| 2005/0182042 A1 | 8/2005 | Feldman et al. | |

(Continued)

FOREIGN PATENT DOCUMENTS

| | | |
|---|---|---|
| EP | 0 206 302 A2 | 12/1986 |
| EP | 1 090 630 A1 | 4/2001 |

(Continued)

OTHER PUBLICATIONS

Portolano et al., J Immunol. Feb. 1, 1993;150(3):880-7.*
Rudikoff et al., Proc Natl Acad Sci U S A. Mar. 1982;79(6):1979-83.*
William E. Paul, M.D., editor, Fundamental Immunology, 3d ed. Raven Press, 1993, p. 242.*
Janeway et al., Immunobiology, 3rd edition, Garland Publishing, 1997, pp. 3:1-3:11.*
Ghiassi-Nejad et al., Expert Rev Gastroenterol Hepatol. Dec. 2008;2(6):803-16. doi: 10.1586/17474124.2.6.803.*
Tanigaki et al., Circ Res. Jan. 16, 2015;116(2):368-84. doi: 10.1161/CIRCRESAHA.116.302795.*
Khreiss et al., Circulation. Apr. 27, 2004;109(16):2016-22. Epub Mar. 29, 2004.*
Stein et al., J Clin Invest. Feb. 2000;105(3):369-76.*

(Continued)

*Primary Examiner* — Michael Szperka
(74) *Attorney, Agent, or Firm* — Lisa M. Warren, Esq.; Morse, Barnes-Brown & Pendleton, P.C.

(57) ABSTRACT

The application provides methods for determining a patient's risk for developing fibrosis or a fibrosis-related disorder. Concentrations of C reactive protein (CRP) and serum amyloid protein (SAP) are measured from a biological sample to determine the SAP-to-CRP ratio. This ratio can then be compared with one or more SAP-to-CRP reference ratios to determine a patient's risk for developing a fibrosis related disorder. The diagnostic methods can also be used to determine the severity of fibrosis in a patient afflicted with such a disease. Furthermore, methods for treating patients having a fibrosis-related disorder are provided. For example, a patient that has a lower SAP-to-CRP ratio than one or more reference values may be treated with an SAP agonist and/or CRP antagonist to treat or prevent a fibrosis disorder. The methods may further comprise determining the R131/H131 polymorphism of FcγRIIA as a risk factor for developing fibrosis or a fibrosis-related disorder.

10 Claims, 9 Drawing Sheets

(56) References Cited

U.S. PATENT DOCUMENTS

| | | | |
|---|---|---|---|
| 2005/0238620 A1* | 10/2005 | Gomer et al. | 424/85.2 |
| 2007/0048855 A1 | 3/2007 | Gamez et al. | |
| 2007/0065368 A1 | 3/2007 | Gomer et al. | |
| 2007/0065866 A1 | 3/2007 | Gomer et al. | |
| 2008/0038192 A1* | 2/2008 | Gervais | 424/1.49 |
| 2008/0044429 A1 | 2/2008 | Johnson et al. | |
| 2009/0074754 A1 | 3/2009 | Hesson et al. | |
| 2009/0074771 A1 | 3/2009 | Koenig et al. | |
| 2009/0202520 A1 | 8/2009 | Lupher, Jr. et al. | |
| 2010/0111898 A1 | 5/2010 | Pelura | |
| 2010/0260781 A1 | 10/2010 | Murray | |
| 2010/0266578 A1 | 10/2010 | Murray | |
| 2010/0317596 A1 | 12/2010 | Willett et al. | |
| 2010/0323970 A1 | 12/2010 | Willett | |

FOREIGN PATENT DOCUMENTS

| | | | |
|---|---|---|---|
| JP | 11319542 A | 11/1999 | |
| WO | WO-1992/021364 A1 | 12/1992 | |
| WO | WO-94/27640 A1 | 12/1994 | |
| WO | WO-1995/005394 A1 | 2/1995 | |
| WO | WO-95/33454 A1 | 12/1995 | |
| WO | WO 97/16568 A1 | 5/1997 | |
| WO | WO-1997/026906 A1 | 7/1997 | |
| WO | WO-99/41285 A1 | 8/1999 | |
| WO | WO-99/45900 A1 | 9/1999 | |
| WO | WO-2001/074300 A1 | 10/2001 | |
| WO | WO-2003/031572 A2 | 4/2003 | |
| WO | WO-2003/097104 A1 | 11/2003 | |
| WO | WO-2004/009823 A1 | 1/2004 | |
| WO | WO-2004/016750 A2 | 2/2004 | |
| WO | WO-2004/058292 A2 | 7/2004 | |
| WO | WO 2004/059293 A2 | 7/2004 | |
| WO | WO-2004/059318 A2 | 7/2004 | |
| WO | WO-2004/076486 A1 | 9/2004 | |
| WO | WO 2004076486 A1 * | 9/2004 | |
| WO | WO-2005/110474 A2 | 11/2005 | |
| WO | WO-2005/115452 A2 | 12/2005 | |
| WO | WO-2006/002438 A2 | 1/2006 | |
| WO | WO-2006/002930 A2 | 1/2006 | |
| WO | WO 2006002930 A2 * | 1/2006 | |
| WO | WO-2006/028956 A2 | 3/2006 | |
| WO | WO 2006/039418 A2 | 4/2006 | |
| WO | WO-2007/047207 A2 | 4/2007 | |
| WO | WO-2007/047796 A2 | 4/2007 | |
| WO | WO-2008/070117 A1 | 6/2008 | |
| WO | WO 2008070117 A1 * | 6/2008 | A61K 38/1716 |
| WO | WO-2009/009019 A2 | 1/2009 | |
| WO | WO-2009/009034 A2 | 1/2009 | |
| WO | WO 2010/104959 A1 | 9/2010 | |
| WO | WO 2010/104961 A1 | 9/2010 | |
| WO | WO 2010/115032 A1 | 10/2010 | |
| WO | WO-2010/141918 A1 | 12/2010 | |

OTHER PUBLICATIONS

Barna et al., "Activation of Human Monocyte Tumoricidal Activity by C-reactive Protein". Cancer Research. 47(5):3959-3963 (1987).

Bharadwaj et al., "Serum Amyloid P Component Binds to Fcγ Receptors and Opsonizes Particles for Phagocytosis". Journal of Immunology. 166(11):6735-3741 (2001).

Bharadwaj et al., "The Major Receptor for C-reactive Protein on Leukocytes Is Fcγ Receptor II". Journal of Experimental Medicine. 190(4):585-590 (1999).

Chen et al., "Platelet FcγRIIA HIS131ARG polymorphism and platelet function: antibodies to platelet-bound fibrinogen induce platelet activation". Journal of Thombosis and Haemostasis. 1(2):355-362 (2003).

Flesch et al., "The FCGR2A—Arg131 variant is no. major mortality factor in the elderly—evidence from a German centenarian study". International Journal of Immunogenetics. 33:277-279 (2006).

Kucuk et al., "Effect of a Selective Cyclooxygenase-2 Inhibitor on Renal Scarring". European Surgical Research. 38(5):451-457 (2006).

Pilling et al., "Reduction of Bleomycin-Induced Pulmonary Fibrosis by Serum Amyloid P" The Journal Immunology. 179(6):4035-4044 (2007).

Pilling, D., et al., "Inhibition of fibrocyte differentiation by serum amyloid P," J. Immunol. 171(10):5537-5546 (2003).

Zhang et al., "C-reactive protein impairs human CD14+ monocyte-derived dendritic cell differentiation, maturaion and function". European Journal of Immunology. 36(11):2993-3006 (2006).

International Search Report, PCT/US2008/008315 dated Mar. 11, 2009.

Abe, R., et al., "Peripheral Blood Fibrocytes: Differentation Pathway and Migration to Wound Sites," The Journal of Immunology, 166(12):7556-7562 (2001).

Aiba, S., et al., "Immunoglobulin-Producing Cells in Plasma Cell Orificial Mucositis," Journal of Cutaneous Pathology, 16(4):207-210 (1989).

Alles, V. V., et al., "Inducible expression of PTX3, a new member of the pentraxin family, in human mononuclear phagocytes," Blood, 84(10):3483-3493 (1994).

Ashcroft, T., et al., "Simple Method of Estimating Severity of Pulmonary Fibrosis on a Numerical Scale," J Clin Pathol, 41(4):467-470 (1988).

Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169(11):6490-6497 (2002).

Azuma, H., et al., "Superagonistic CD28 Antibody Induces Donor-Specific Tolerance in Rat Renal Allografts," American Journal of Transplatation, 8(10):2004-2014 (2008).

Bain, J., et al., "The Specificities of Protein Kinase Inhibitors: An Update," Biochem. J, 371(Pt 1):199-204 (2003).

Bickerstaff, M. C. M., et al., "Serum Amyloid P Component Controls Chromatin Degration and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," The Journal of Immunology, 166(7):4498-4506 (2001).

Castano, A. P., et al., Serum Amyloid P Inhibits Fibrosis Through FcγR-Dependent Monocyte-Macrophage Regulation in Vivo. Sci. Transl. Med. 1(5):1-26 (2009).

Chesney, J., et al., "Peripheral Blood Fibrocytes: Mesenchymal Precursor Cells and the Pathogenesis of Fibrosis," Curr.Rheumatol. Rep, 2(6):501-505 (2000).

Chesney, J., et al., "Regulated Production of Type I Collagen and Inflammatory Cytokins by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRlla on HL-60 Granulocytes," The Journal of Immunology, 168:1413-1418 (2002).

Christner, R. B., et al., "Binding of Human Serum Amyloid P-Component to Phosphocholine", Archives of Biochemistry and Biophysics, 314(2):337-343 (1994).

(56) References Cited

OTHER PUBLICATIONS

Clark, R. A. F., "Fibrin and Wound Healing," Annals New York Academy of Sciences 936:355-367 (2001).
Crouch, E., "Patholbiology of Pulmonary Fibrosis," Am J Physiol Lung Cell Mol Physiol, 259(4 Pt 1):L159-L184 (1990).
D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).
Daëron, M., "Fe Receptor Biology," Annual Review of Immunology 15:203-234 (1997).
Daëron, M., "Structural Bases of FcγR Functions," Int Rev Immunol. 16(1-2):1-27 (1997).
De Beer, F. C., et al., "Fibronectin and C4-Binding Protein are Selectively Bound by Aggregated Amyloid Component", J Exp Med., 154(4):1134-1149 (1981).
De Beer, F. C., et al., "Isolation and Characterization of C-Reactive Protein and Serum Amyloid P Component in the Rat," Immunology 45(1):55-70 (1982).
De Beer, F. C., et al., "Isolation of Human C-Reactive Protein and serum Amyloid P Component," Journal of Immunological Methods, 50(1):17-31 (1982).
de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).
De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.
Du Clos, T. W., "C-Reactive Protein Reacts With the U1 Small Nuclear Ribonucleoprotein," The Journal of Immunology, 143(8):2553-2559 (1989).
Du Clos, T. W., et al., "Reply to Human C-reactive protein does not bind to fc gamma RIIa on phagocytic cells," The Journal of Clinical Investigation, vol. 107(5):643 (2001).
Duchemin, A. M., et al., "Association of Non-Receptor Protein Tyrosine Kinases with the Fc Gamma RI/Gamma-Chain Complex in Monocytic Cells," The Journal of Immunology, 158(2):865-871 (1997).
Emsley, J., et al., "Structure of Pentameric Human Serum Amyloid P Component," Nature 367(6461):338-345 (1994).
Garden, A. S., et al., "Head and Neck Radiation and Mucositis," 1(1):30-34 (2007).
Gerhard et al., "The Status, Quality, and Expansion of the NIH Full-Length cDNA Project: The Mammalian Gene Collection (MGC)," Genome Research, 14(10B):2121-2127 (2004).
Gewurz, H., et al., "Structure and Function of the Pentraxins," Current Opinion in Immunology, 7(1):54-64 (1995).
Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).
Giorgini, A., et al., "Blockade of Chronic Graft-Versus-Host Disease by Alloantigen-induced CD4+CD25+Foxp3+ Regulatory T Cells in Nonlymphopenic Hosts," Journal of Leukocyte Biology, 82(5):1053-1061 (2007).
Gregory, S. G., et al., "The DNA Sequence and Biological Annotation of Human Chromosome 1", Nature 441(7091):315-321 (2006).
Guyre, C. A., et al., "Receptor Modulation by FcγRI-Specific Fusion Porteins is Dependent on Receptor Number and Modified by IgG," The Journal of Immunology, 167(11):6303-6311 (2001).
Hamazaki, Hideaki, "Structure and significance of N-linked sugar unit of human serum amyloid P component," *Bichimica et Biophysica Acta*, 1037(3):435-438 (1990).
Harris, J. M., et al., "Pegylation a Novel Process for Modifying Pharmacokinetics," Clin. Pharmacokinetics, 40(7):539-551 (2001).

Hartlapp, I., et al., "Fibrocytes Induce an Angiogenic Phenotype in Cultured Endothelial Cells and Promote Angiogenesis In Vivo," The FASEB Journal, 15(12):2215-2224 (2001).
Heegaard, N. H. H., et al., "Ligand-Binding Sites in Human Serum Amyloid P Component," Eur. J. Biochem. 239(3):850-856 (1996).
Hicks et al., "Serum amyloid P component binds to histones and activates the classical complement pathway", The Journal of Immunology, 149:3689-3694 (1992).
Hind, C. R. K., et al., "Human Serum Amyloid P Component, a Circulating Lectin with Specificity for the Cyclic 4,6-Pyruvate Acetal of Galactose: Interactions with Various Bacteria", Biochem. J., 225(1):107-111 (1985).
Hind, C. R., et al, "Binding specificity of serum amyloid P-component for the pyruvate acetal of galactose," Journal of Experimental Medicine, 159(4):1058-1069 (1984).
Hohenester, E., et al., "Crystal Structure of a Decameric Complex of Human Serum Amyloid P Component with Bound dAMP", J. Mol. Biol. 269(4):570-578 (1997).
Huang, Z. Y., et al., "The Monocyte Fcγ Receptors FcγRI/γ and FcγRIIA Differ in their Interaction with Syk and with Src-Related Tyrosine Kinases," J Leukoc Biol 76(2):491-499 (2004).
Hundt, M., et al., "Treatment of Acute Exacerbation of Systemic Lupus Erythematosus with High-Dose Intravenous Immunoglobulin," Rheumatology (Oxford), 39(11) 1301-1302 (2000).
Hutchinson, W. L., et al., "Human Serum Amyloid P Component is a Single Uncomplexed Pentamer in Whole Serum," Molecular Medicine, 6(6):482-493 (2000).
Janeway, et al., Immunobiology, 3rd edition, Garland Publishing, pp. 3:1-3:11 (1997).
Jenny, N. S., et al., "Serum Amyloid P and Cardiovascular Disease in Older Men and Women Results from the Cardiovascular Health Study," Arterioscler. Thromb. Vasc. Biol., 27:352-358 (2007).
Junqueira, L. C.,et al., "Picrosirius Straining Plus Polarization Microscopy, A Specific Method for Collagen Detection in Tissue Sections," Histochem. J, 11(4):447-455 (1975).
Kessel, A., et al., Intravenous Immunoglobulin Therapy Affects T Regulatory Cells by Increasing Their Suppressive Function, The Journal of Immunology, 179(8):5571-5575 (2007).
Kieman, U. A., et al., "Proteomic Characterization of Novel Serum Amyloid P Component Variants from Human Plasma and Urine," Proteomics 4(6):1825-1829 (2004).
Kisseleva, T., et al., "Bone Marrow-Derived Fibrocytes Participate in Pathogenesis of Liver Fibrosis," Journal of Hepatology, 45(3):429-438 (2006).
Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2003).
Kolstoe et al., "Molecular dissection of Alzheimer's disease neuropathology by depletion of serum amyloid P component", *PNAS*, 106(18):7619-7623 (2009).
Korade-Mirnics, Z.,et al., "Src Kinase-Mediated Signaling in Leukocytes," J Leukoc Biol., 68(5):603-613 (2003).
Lai, J. Y., et al., "Potent Small Molecule Inhibitors of Spleen Tyrosine Kinase (Syk)," Bioorganic & Medicinal Chemistry Letters, 13(18):3111-3114 (2003).
Lei, K. K., et al., "Genomic DNA Sequence for Human C-Reactive Protein," J. Biol. Chem. 260(24):13377-13383 (1985).
Lindenbaum, E. S., et al., "Serum-Free Cell Culture Medium Induces Acceleration of Wound Healing in Guinea-Pigs," Burns, 21(2):110-115 (1995).
Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).
Lu, J., et al., "Structural Recognition and Functional Activation of FcγR by Innate Pentraxins," Nature, 456(7224):989-992 (2008).
Majno, G., "Chronic Inflammation: Links With Angiogenesis and Wound Healing," American Journal of Pathology, 153(4):1035-1039 (1998).
Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).

(56) References Cited

OTHER PUBLICATIONS

Marnell, L. L., et al., "C-Reactive Protein Binds to FcγRI in Transfected COS Cells," The Journal of Immunology, 155(4):2185-193 (1995).
Metz, C. N., "Fibrocytes: A Unique Cell Population Implicated in Wound Healing," Cell. Mol. Life Sci., 60(7):1342-1350 (2003).
Mold, C., et al., "Serum Amyloid P Component and C-Reactive Protein Mediate Phagocytosis Through Murine FcγRs," The Journal of Immunology, 166(2):1200-1205 (2001).
Moore, B. B., et al., "CCR2-Mediated Recruitment of Fibrocytes to the Alveolar Space After Fibrotic Injury," American Journal of Pathology, 166(3):675-684 (2005).
Mori, L., et al., "Fibrocytes Contribute to the Myofibroblast Population in Wounded Skin and Originate From the Bone Marrow," Exp Cell Res., 304(1):81-90 (2005).
Mortensen, R. F., et al., "Regulation of phagocytic leukocyte activities by C-reactive protein," Journal of Leukocyte Biology, 67(4):495-500 (2000).
Murphy, T. M., et al., "Extrahepetic Transcription of Human C-Reactive Protein," Journal of Experimental Medicine, 73(2):495-498 (1991).
Murray, L. A., et al., "Serum Amyloid P Therapeutically Attenuates Murine Bleomycin-induced Pulmonary Fibrosis Via Its Effects on macrophages," PLoS, 5(3):e9683 (2010).
Ohnishi, S. et al., "Isolation and Characterization of the Complete Complementary and Genomic DNA Sequences of Human Serum Amyloid P Component," J. Biochem, 100(4):849-858 (1986).
Oliveira, E. B., et al., "Primary Structure of Human C-Reactive Protein," The Journal of Biological Chemistry, 254(2):489-502 (1979).
Oriente, A., et al., "Interleukin-13 Modulates Collagen Homeostasis in Human Skin and Keloid Fibroblasts," The Journal of Pharmacology and Experimental Therapeutics, 292(3):988-994 (2000).
Osmand, A. P., et al., Partial Amino-Acid Sequences of Human and Rabbit C-Reactive Proteins: Homology with Immunoglobulins and Histocompatibility AntigensProc. Natl. Acad. Sci. U.S.A., 74(3):1214-1218 (1977).
Pachence, J., et al., "Tissue-Activated Delivery—Novel Methods for Site-Directed Drug Delivery," Drug Delivery Technology, 3(1):40-45 (2003).
Painter, R. H., "Evidence that C1t (amyloid P-component) is not a subcomponent of the first component of complement (CI)"; J. Immunol., 119(6):2203-2205 (1977).
Paul, William E., M.D., editor, Fundamental Immunology, 3d ed. Raven Press, p. 242 (1993).
Pepys et al., Glycobiology of Human Serum Amyloid P Component Amyloid Amyloidosis, *Proc. Int. Symp. Amyloidosis*, pp. 177-179 (1994).
Pepys, et al., "Targeted pharmacological depletion of serum amyloid P component for treatment of human amyloidosis", *Nature*, 471:254-259 (2002).
Pepys, et al., Human serum amyloid P component is an invariant constituent of amyloid deposits and has a uniquely homogeneous glycostructure, PNAS, 91:5206-5606 (1994).
Pepys, M. B., "Isolation of serum amyloid P-component (Protein SAP) in the Mouse," Immunology, 37(3):637-641 (1979).
Pepys, M. B., et al., "Amyloid P Component. A Critical Review," Amyloid: Int. J. Exp. Invest., 4(4):274-295 (1997).
Pepys, M. B., et al., "Serum Amyloid P Component is the Major Calcium-Dependent Specific DNA Binding Protein of Serum," Biochemical and Biophysical Research Communications, 148(1):308-313 (1987).
Philips, R. J., et al., "Circulating Fibrocytes Traffic to the Lungs in Response to CXCL 12 and Mediate Fibrosis," The Journal of Clinical Investigation, 114(3):438-446 (2004).
Pilling, D., et al., "Aggregated IgG Inhibits the Differentiation of Human Fibrocytes," Journal of Leukocyte Biology, 7996):1242-1251 (2006).
Pontet, M., et al., "One step preparation of both human C-reactive protein and Cit," FEBS Letters, 88(2):172-175 (1978).
Portolano et al., Lack of Promiscuity in Autoantigen-Specific H and L Chain Combinations as Revealed by Human H and L Chain "Roulette" J. Immunol., 150(3):880-887 (Feb. 1, 1993).
Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).
Prelli, F., et al., "The Primary Structure of Human Tissue Amyloid P Component From a Patient with Primary Idiopathic Amyloidosis," The Journal of Biological Chemistry, 260(24):12895-12898 (1985).
Quan et al., "The role of circulating fibrocytes in fibrosis" Current Rheumatology Reports. 8(2): 145-150 (2006).
Rudikoff et al., Single amino acid substitution altering antigen-binding specificity. Proc Natl Acad Sci USA, 79(6):1979-1983 (Mar. 1982).
Russo, F. P., et al., "Bone Marrow Functionality Contributes to Liver Fibrosis," Gastroenterology Week Jul. 31, 2006, 130(6):83-84.
Sada, K., et al., "Structure and Function of Syk Protein-Tyrosine Kinase," J Biochem, 130(2):177-186 (2001).
Saeland, E., at al., "Human C-reactive Protein Does not Bind to FcγRIIa on Phagocytic Cells," The Journal of Clinical Investigation, 107(5):641-643 (2001).
Sawada et al., "The Ace Inhibitor, Quinapril, Ameliorates Peritoneal Fibrosis in an Encapsulating Peritoneal Sclerosis Model in Mice" Pharmacological Research. 46(6): 505-510 (2002).
Schmidt, M., et al., "Identification of Circulating Fibrocytes as Precursors of Bronchial Myofibroblasts in Asthma," The Journal of Immunology, 171(1):380-389 (2003).
Shoenfeld, Y., et al., The mosaic of Autoimmunity: Prediction, Autoantibodies, and Therapy in Autoimmune Diseases—2008, Israel Medical Association Journal, 10(1)13-19 (2008).
Shrive, A. K., et al., "Three Dimensional Structure of Human C-Reactive Protein," Nature Structural Biology, 3(4):346-354 (1996).
Siebert et al., "Effect of enzymatic desialylation of human serum amyloid P component on surface exposure of laser photo CIDNP (chemically induced dynamic nuclear polarization)-reactive histidine, tryptophan and tyrosine residues," *FEBS Letters*, 371(1):13-6 (1995).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRIIa on Human Monocytes and Neutrophils is Allele-Specific," The Journal of Clinical Investigation, 105(3):369-376 (2000).
Su, L., et al., "Distinct Mechanisms of Stat Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).
Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).
Toubi, E., et al., "High Dose Intravenous Immunoglobulins: An Option in the Treatment of Systemic Lupus Erythematosus," Human Immunology, 66(4):395-402 (2005).
Tridandapani, S., et al., "Regulated Expression and Inhibitory Function of FcgammaRIIb in Human Monocytic Cells," Journal of

(56) References Cited

OTHER PUBLICATIONS

Biological Chemistry, The American Society for Biochemistry and Molecular Biology, Inc, 277(7):5082-5089 (2002).
Trinchieri, G., "Interleukin-12 and the Regulation of Innate Resistance and Adaptive Immunity," Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).
Turner, M., et al., "Tyrosine Kinase SYK: Essential Functions for Immunoreceptor Signalling," Immunology Today, 21(3):148-154 (2000).
Underwood, D. C., et al., SB 239063, "A p38 MAPK Inhibitor, reduces Neutrophilia, Infamatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yang, L., PhD, et al., "Identification of Fibrocytes in Postburn Hypertrophic Scar," Wound Repair and Regeneration, 13(4):398-404 (2005).
Zahedi K., "Characterization of the Binding of Serum Amyloid P To Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Barabino and Dana, "Animal Models of Dry Eye: A Critical Assessment of Opportunities and Limitations," Investigative Ophthalmology & Visual Science, vol. 45(6): 1641-1646 (2004).
Brasil et al., "Tear film analysis and its relation with palpebral fissure height and exophthalmos in Graves' ophthalmopathy," Arquivos Brasileiros de Oftalmologia, vol. 58(5): 615-618 (2005). (Abstract).
<http://en.wikipedia.org/wiki/Pentraxins> downloaded from the internet on Apr. 16, 2013.
<http://en.wikipedia.org/wiki/Serum_amyloid_P_component> downloaded from the internet on Apr. 16, 2013.
Agostini, et al., "Chemokine/Cytokine Cocktail in Idiopathic Pulmonary Fibrosis," Proc. Am. Thorac. Soc., 3(4):357-363 (2006).
Agostini, et al., Proc. Am. Thorac. Soc., 3:357-363 (2006).
Booth, D. R., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).
Boysen, S. et al., "Recombinant human serum amyloid P component from Pichia pastoris: production and characterization," Protein Expression and Purification, vol. 35(2): 284-292 (2004).
Chatziantoniou, et al., "Is Kidney Injury a Reversible Process," Curr. Opin. Nephrol. Hypertension, 17(1):76-81 (2008).
Duckworth, et al., "The Structure of Agar Part I. Fractionation of a Complex Mixture of Polysaccharides," Carbohydrate Research, 16:189-197 (1971).
Garcia de Frutos et al., "Serum Amyloid P Component Binding to C4b-binding Protein," The Journal of Biological Chemistry: 270(45):26950-26955 (1995).
Gehring, et al., "Effect of Topically Applied Dexpanthenol on Epidermal Barrier Function and Stratum Corneum Hydration," Arzneim-Forsch./Drug Res., 50(11):659-663 (2000).
Giri, S., et al., "Antifibrotic Effect of Decorin in a Bleomycin Hamster Model of Lung Fibrosis," Biochemical Pharmacology, 54:1205-1216 (1997).
Heegaard, N.H.H., "Microscale characterization of the structure-activity relationship of a heparin-binding glycopeptide using affinity capillary electrophoresis and immobilized enzymes," Journal of Chromatography, vol. 853(1-2):189-195 (1999).
Hogaboam et al., "Chronic Airway Hyperreactivity, Goblet Cell Hyperplasia, and Peribronchial Fibrosis during Allergic Airway Disease Induced by Aspergillus fumigatus," American Journal of Pathology, vol. 156(2), pp. 723-732 (2000).
Ilium, Lisbeth, "Nasal Drug Delivery-possibilities, problems and solutions," Journal of Controlled Release, vol. 87(1-3):187-198 (2003).
Ishaque, et al., "Role of Vitamins in Determining Apoptosis and Extent of Suppression by bcl-2 During hybridoma Cell Culture," Apoptosis, 7(3):231-239 (2002).
Kawashima et al., Pulmonary delivery of insulin with nebulized DL-lactide/glycolide copolymer (PLGA) nanospheres to prolong hypoglycemic effect, Journal of Controlled Release, vol. 62(1-2): 279-287 (1999).
Kiernan, U.A., et al., "Selected Expression Profiling of Full-Length Proteins and Their Variants from Human Plasma," Clin. Proteomics 1:7-16 (2004).
Kinoshita CM, et al., "A Protease-Sensitive Site in the Proposed Ca2+-Binding Region of Human Serum Amyloid Component and Other Pentraxins." Protein Sci., 1:700-709 (1992).
Moreira et al., "Serum amyloid P attenuates M2 macrophage activation and protects against fungal spore-induced allergic airway disease," Journal of Allergy and Clinical Immunology, vol. 126(4), pp. 712-721 (2010).
Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998). Note: Only pp. 6-8 have been provided).
Rudinger, J., "Characteristics of the amino acids as components of a peptide hormone sequence," Peptide Hormones:1-7 (1975).
Russo, et al., "Liver Fibrosis; Bone Marrow Functionality Contributes to Liver Fibrosis," 130(6) Gastroenterology Week Jul. 31, 2006 pp. 83-84 (2006).
Schwalbe, et al., "Pentraxin Family of Proteins Interact Specifically with Phosphorylcholine and/or Phosporylethanolamine," Biochemistry, 31:4907-1645 (1992).
Siebert, Hans-Christian et al., "Comparison between intact and desialylated human serum amyloid P component by laser photo CIDNP (chemically induced dynamic nuclear polarization) technique: An indication for a conformational impact of sialic acid," Glycoconjugate Journal, vol. 14(8):945-949 (1997).
Wang, Q., et al., "Effect of Antibody Against Integrin α4 on Bleomycin-Induced Pulmonary Fibrosis in Mice," Biochemical Pharmacology, 60:1949-1658 (2000).Wang, et al., Biochem. Pharmacol., 60:1949-1958 (2000).
Weimann, et al., "Studies of Wound Healing: Effects of Calcium D-Panthothenate on the Migration, Proliferation and Protein Synthesis of Human Dermal Fibroblasts in Culture," Interat. J. Vit. Nutr. Res., 69(2):113-119 (1999).
Yu, L., et al., "Therapeutic Strategies to Halt Renal Fibrosis," Current Opinion in Pharmacology, 2:177-181 (2002).
Banham et al., "FOXP3+ regulatory T cells: Current controversies and future perspectives," European Journal of Immunolgoy, vol. 36(11): 2832-2836 (2006).
Hori, Shohel, "Journal of Clinical and Experimental Medicine", vol. 227(5); 294-298 (2008) (abstract).

(56) References Cited

OTHER PUBLICATIONS

Mascarenhas, J., "Rationale for combination therapy in myelofibrosis'," Best Practice & Research Clinical Haematology, vol. 27: 197-208 (2014).
Murray et al., "TGF-beta driven lung fibrosis is macrophage dependent and blocked by Serum amyloid P," The International Journal of Biochemistry & Cell Biology, vol. 43: 154-162 (2011).
Nybo et al., "Isoforms of Murine and Human Serum Amyloid p. Component," Scan. J. Immunol., vol. 48: 350-356 (1998).
Saeland, E., at al., "Human C-reactive Protein Does not Bind to FcγRIIa on Phagocytic Cells," The Journal of Clinical Investigation, 107(5):641-643.
Schrader et al., "Animal models of dry eye," Developments in ophthalmology, vol. 41: 298-312 (2008). (Abstract).
Tanaka and Sakaguchi, "Regulatory T cell and autoimmune diseases," Japanese Journal of Clinical Immunology, vol. 28(5): 291-299 (2005).
Tennent et al., "Macrophage dependent elimination of amyloid following treatment with anti-SAP antibody," Amyloid: The International Journal of Experimental and Clinical Investigation, vol. 17(1); p. 51 (2010).
Ying et al., "Human Serum Amyloid P Component Oligomers Bind and Activate the Classical Complement Pathway via Residues 14-26 and 76-92 of the A Chain collagen-Like Region of C1q," J. Immunol. vol. 150(1): 169-176 (1993).
Zheng, J., et al., "Piceatannol,a Stilbene Phytochemical, Inhibits Mitochondrial FOF1-ATPase Activity by Targeting the FI Complex," Biochemical and Biophysical Research Communications, 261(2):499-503 (1999).

\* cited by examiner

Figure 1

```
Homo sapiens     H T D L S G K V F V F P R E S V T D H V N L I T P L E K P L
Gallus gallus    Q E D L Y R K V F V F R E D P S D A Y V L L Q V Q L E R P L
Bos taurus       Q T D L R G K V F V F P R E S S T D H V T L I T K L E K P L
C. migratorius   Q T D L T G K V F V F P R E S E S D Y V K L I P R L E K P L Homo sapiens     Q N F T L C F R A Y S D L S R A Y S L F S Y N T Q G R D N E
Gallus gallus    L N F T V C L R S Y T D L T R P H S L F S Y A T K A Q D N E
Bos taurus       K N L T L C L R A Y S D L S R G Y S L F S Y N I H S K D N E
C. migratorius   E N F T L C F R T Y T D L S R P H S L F S Y N T K N K D N E Homo sapiens     L L V Y K E R V G E Y S L Y I G R H K V T S K V I E K F P A
Gallus gallus    I L L F K P K P G E Y R F Y V G G K Y V T F R V P E N R G E
Bos taurus       L L V F K N G I G E Y S L Y I G K T K V T V R A T E K F P S
C. migratorius   L L I Y K E R M G E Y G L Y I E N V A I V R G V E E F A S Homo sapiens     P V H I C V S W E S S S G I A E F W I N G T P L V K K G L R
Gallus gallus    W E H V C A S W E S G S G I A E F W L N G R P W P R K G L Q
Bos taurus       P V H I C T S W E S S T G I A E F W I N G K P L V K R G L K
C. migratorius   P V H F C T S W E S S S G I A D F W V N G I P W V K K G L K Homo sapiens     Q G Y F V E A Q P K I V L G Q E Q D S Y G G K F D R S Q S F
Gallus gallus    K G Y E V G N E A V V M L G Q E Q D A Y G G G F D V Y N S F
Bos taurus       Q G Y A V G A H P K I V L G Q E Q D S Y G G G F D K N Q S F
C. migratorius   K G Y T V K T Q P S I I L G Q E Q D N Y G G G F D K S Q S F Homo sapiens     V G E I G D L Y M W D S V L P P E N I L S A Y Q G T P L P A
Gallus gallus    T G E M A D V H L W D A G L S P D K M R S A Y L A L R L P P
Bos taurus       M G E I G D L Y M W D S V L S P E E I L L V Y Q G S S S I S
C. migratorius   V G E M G D L N M W D S V L T P E E I K S V Y E G S W L E P Homo sapiens     N I L D W Q A L N Y E I R G Y V I I K P L V W V
Gallus gallus    A P L A W G R L R Y E A K G D V V V K P R L R E A L G A
Bos taurus       P T I L D W Q A L K Y E I K G Y V I V K P M V W G
C. migratorius   N I L D W R A L N Y E M S G Y A V I R P R V W H
```

Figure 3
A
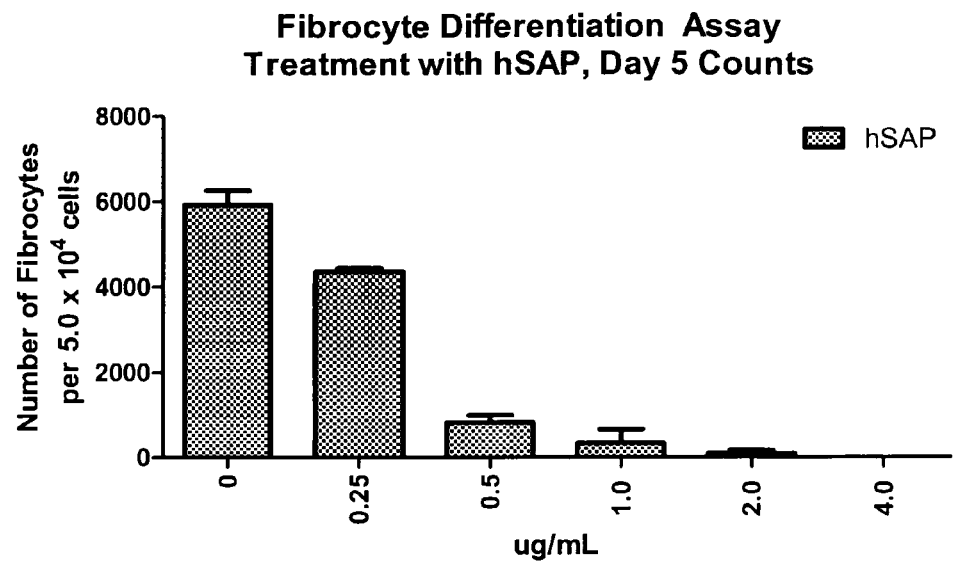
B
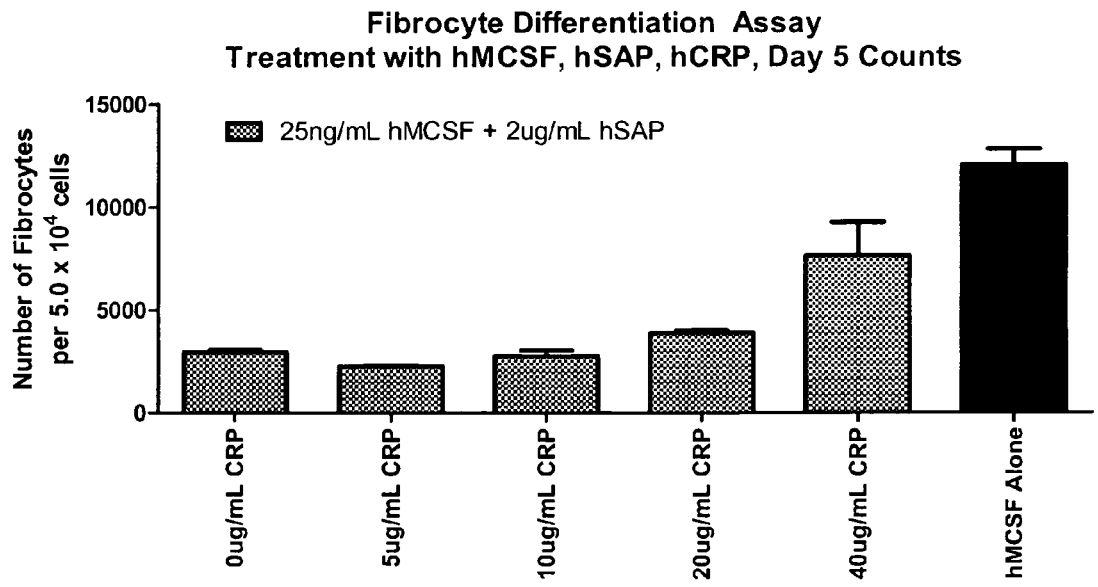

Figure 5
A
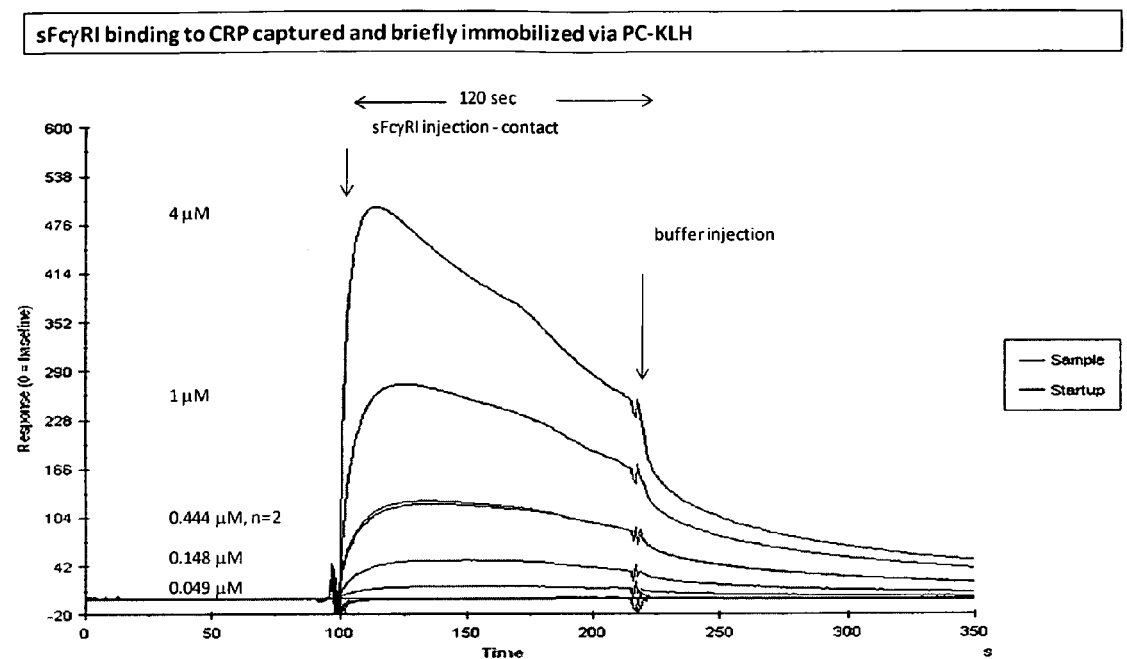
B
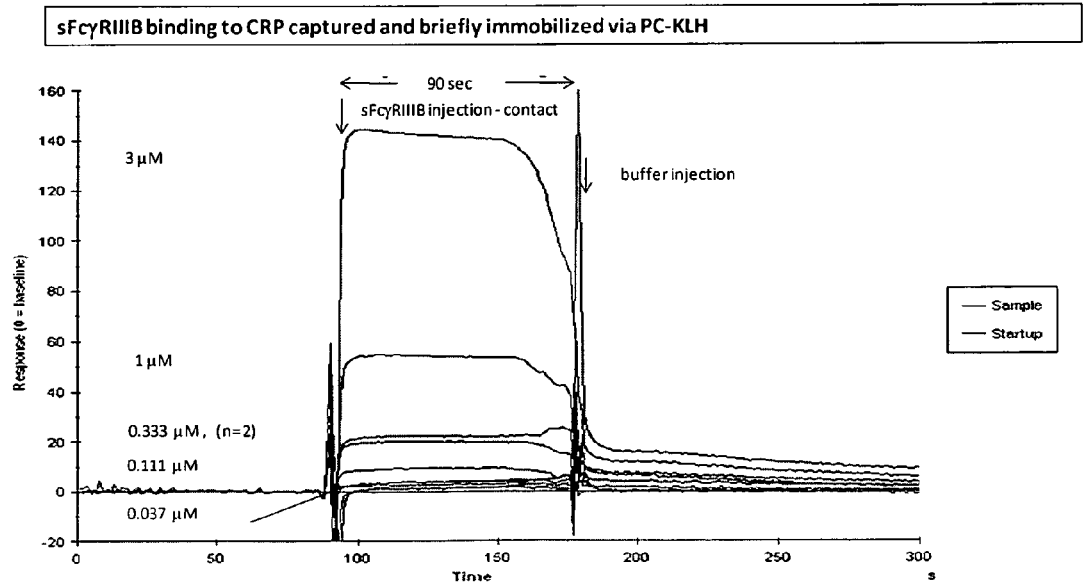

Figure 6
A    Plot of $R_{eq}$ (response at equilibrium) against FcγRI concentration
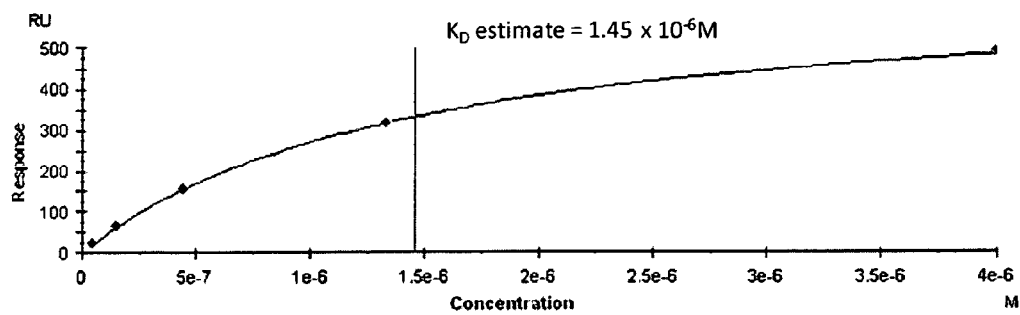
B    Plot of $R_{eq}$ (response at equilibrium) against FcγRIIIB concentration
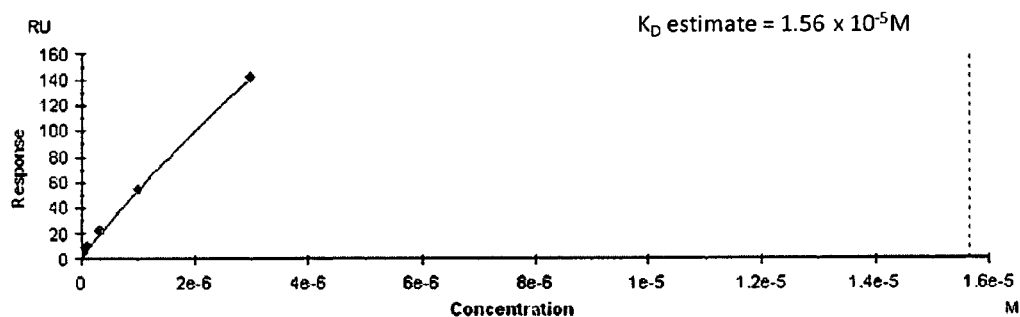

Figure 8
A
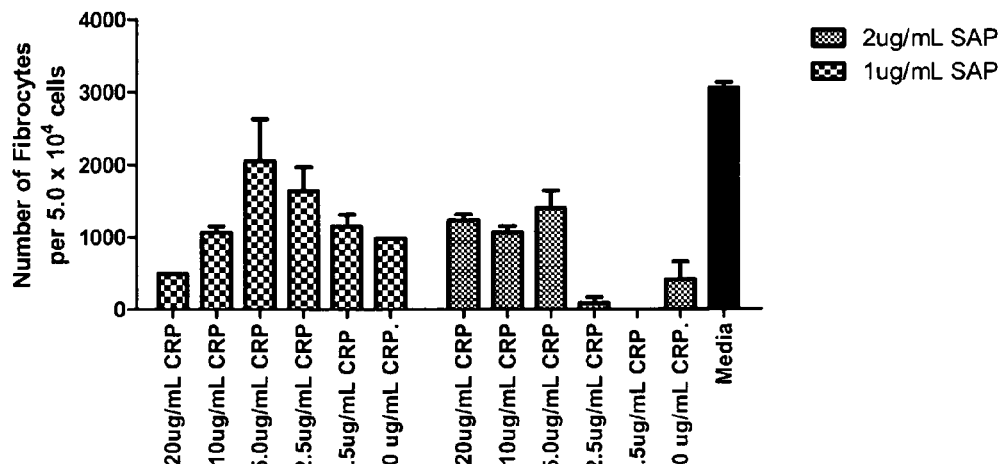
B
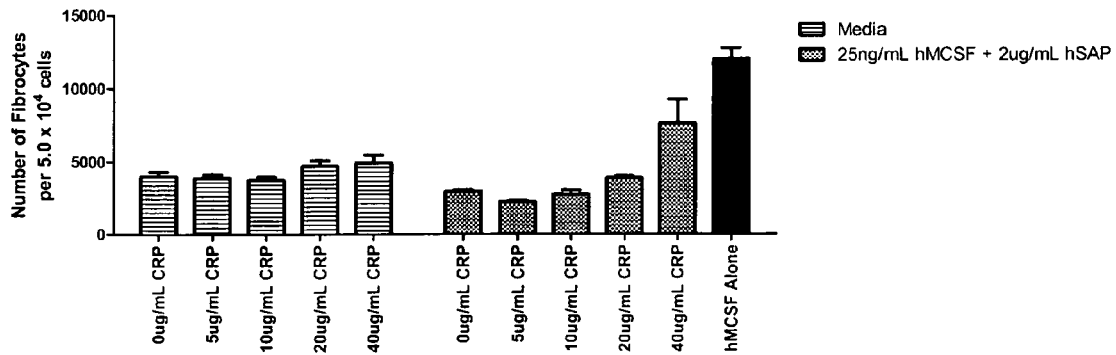

C

METHODS FOR TREATING FIBROSIS USING CRP ANTAGONISTS

CROSS-REFERENCE TO RELATED APPLICATION

This application claims the benefit of U.S. Provisional Application No. 60/958,634, filed on Jul. 6, 2007, the contents of which are incorporated herein by reference in their entirety.

BACKGROUND OF THE INVENTION

The process of tissue repair as a part of wound healing involves two phases. The first phase is the regenerative phase, in which injured cells are replaced by cells of the same type. The second phase is the formation of fibrous tissues, also called fibroplasia or fibrosis, in which connective tissue replaces normal parenchymal tissues. The tissue repair process can become pathogenic if the fibrosis phase continues unchecked, leading to extensive tissue remodeling and the formation of permanent scar tissue.

It has been estimated that up to 45% of deaths in the United States can be attributed to fibroproliferative diseases, which can affect many tissues and organ systems. Major organ fibrotic diseases include interstitial lung disease (ILD), characterized by pulmonary inflammation and fibrosis. ILD is known to have a number of causes such as sarcoidosis, silicosis, collagen vascular diseases, and systemic scleroderma. However, idiopathic pulmonary fibrosis, a common type of ILD, has no known cause. Other organ fibrotic disorders include liver cirrhosis, liver fibrosis resulting from chronic hepatitis B or C infection, kidney disease, heart disease, and eye diseases including macular degeneration and retinal and vitreal retinopathy. Fibroproliferative disorders also include systemic and local scleroderma, keloids and hypertrophic scars, atherosclerosis, and restenosis. Additional fibroproliferative diseases include excessive scarring resulting from surgery, chemotherapeutic drug-induced fibrosis, radiation-induced fibrosis, and injuries and burns.

Currently, treatments are available for fibrotic disorders including general immunosuppressive drugs such as corticosteroids, and other anti-inflammatory treatments. However, the mechanisms involved in regulation of fibrosis appear to be distinctive from those of inflammation, and anti-inflammatory therapies are seldom effective in reducing or preventing fibrosis. Therefore, a need remains for developing treatments to reduce and prevent fibrosis and control fibrotic disorders.

SUMMARY OF THE INVENTION

The application provides methods for determining a patient's risk for developing a fibrosis related disorder. Concentrations of C reactive protein (CRP) and serum amyloid P (SAP) are measured from a biological sample to determine the SAP-to-CRP ratio. The ratio is compared with one or more SAP-to-CRP reference ratios. A SAP-to-CRP ratio that is at least 10% lower than one or more reference ratios is an indication that the patient is at risk for developing a fibrosis related disorder. In some embodiments, a second biological sample from a patient is assayed to determine the sequence of the polymorphic FcγRIIA allele. Patients having one or both alleles of the R131 polymorphism and an SAP-to-CRP ratio that is at least 5% lower than a reference ratio are indicated as being at risk for developing a fibrosis related disorder.

The application further provides methods for diagnosing a fibrosis related disorder in a patient. Concentrations of CRP and SAP are measured from a biological sample to determine the SAP-to-CRP ratio. The ratio is compared with one or more SAP-to-CRP reference ratios. A SAP-to-CRP ratio that is at least 20% lower than one or more reference ratios is an indication that the patient is at risk for developing a fibrosis related disorder.

The application further provides methods for treating, preventing or reducing the severity of a fibrosis related disorder in a patient. Concentrations of CRP and SAP are measured from a biological sample to determine the SAP-to-CRP ratio. The ratio is compared with one or more SAP-to-CRP reference ratios. Patients having an SAP-to-CRP ratio that is at least 10% lower than a reference ratio are administered an anti-fibrotic therapy. In some embodiments, a second biological sample from a patient is assayed to determine the sequence of the polymorphic FcγRIIA allele. Patients having one or both alleles of the R131 polymorphism and an SAP-to-CRP ratio that is at least 5% lower than the reference ratios are administered an anti-fibrotic therapy.

The application further provides a method for adjusting the treatment of a fibrosis related disorder in a patient. Concentrations of CRP and SAP from a patient are measured to determine an SAP-to-CRP ratio. The ratio is compared with one or more reference SAP-to-CRP ratios. Patients having an SAP-to-CRP ratio that is lower that the reference ratios are administered an anti-fibrotic therapy. Concentrations of CRP and SAP from a patient are measured again to determine a subsequent ratio. The dosage or frequency of dosing of the anti-fibrotic therapy is adjusted in order to achieve a target SAP-to-CRP ratio.

The concentration of CRP and SAP may be measured from serum, plasma, healthy tissue, or fibrotic tissue and can be measured as total concentration or as free concentration, or unbound, of CRP or SAP protein. The measurements may be made repeatedly in the process of adjusting the treatment of a fibrosis related disorder. The reference ratio may be healthy tissue of a patient when compared to fibrotic tissue. The reference ratio may also be obtained from a cohort of subjects with the same age and gender as the patient. The SAP-to-CRP ratio may be 60, 50, 40, 30, 20, 10, or 5. The anti-fibrotic therapy may include CRP antagonists and/or SAP agonists, and the SAP agonists and CRP antagonists may be administered individually or conjointly.

The application further provides methods for treating, preventing or reducing the severity of a fibrosis related disorder in a patient by conjointly administering a therapeutically effective amount of one or more CRP antagonists and one or more SAP agonists.

The SAP agonist may be selected from a small molecule, nucleic acid, or polypeptide. The SAP agonist may increase SAP signaling, mimic SAP signaling, increase SAP activity, increase SAP expression, or increase serum SAP levels. In some embodiments, the SAP agonist may be a SAP polypeptide, an FcγR antibody (anti-FcγRI, anti-FcγRIIA, or anti-FcγRIII), a cross-linked anti-FcγR antibody (anti-FcγRI, anti-FcγRIIA, or anti-FcγRIII), an aggregated IgG antibody, or a cross-linked IgG antibody.

The application further provides methods for treating, preventing or reducing the severity of a fibrosis related disorder in a patient by determining the concentration of CRP in a biological sample. The concentration of CRP in the biological sample is compared with one or more CRP reference values. A CRP concentration that is at least 10% higher than one or more reference values is administered one or more CRP antagonists. In some embodiments, a second biological sample from a patient is assayed to determine the sequence of the polymorphic FcγRIIA allele. Patients having one or both alleles of the R131 polymorphism and a CRP concentration that is at least 5% higher than the reference ratios are administered an anti-fibrotic therapy. In some embodiments, the fibrosis related disorder is not atherosclerosis.

The concentration of CRP may be measured from serum, plasma, healthy tissue, or fibrotic tissue and can be measured as total concentration or as free concentration, or unbound, of CRP protein. The measurements may be made repeatedly in the process of adjusting the treatment of a fibrosis related disorder. The reference ratio may be healthy tissue of a patient when compared to fibrotic tissue. The reference ratio may also be obtained from a cohort of subjects with the same age and gender as the patient. The CRP reference value may be 0.1 µg/ml, 0.5 µg/ml, 1 µg/ml, 3 µg/ml, 10 µg/ml, or 20 µg/ml. The anti-fibrotic therapy may include CRP antagonists and/or SAP agonists, and the SAP agonists CRP antagonists may be administered individually or conjointly.

The CRP antagonist may be selected from a small molecule, nucleic acid, or polypeptide. The CRP antagonist may decrease CRP signaling, decrease CRP activity, decrease CRP expression, decrease serum CRP levels, decrease production of IL-10, decrease production of TGF-β, or decrease CRP binding to FcγRI or FcγRIIA or FcγRIII. In some embodiments, the CRP antagonist may be an anti-CRP antibody, anti-FcγRI antibody, anti-FcγRII antibody, or anti-FcγRIII antibody. In some embodiments, the CRP antagonist may be selected from cyclooxygenase-2 inhibitors, anti-platelet agents, statins, inhibitors of cholesterol absorption, hypolipidemic agents, niacin, antidiabetic agents, β-adrenoreceptor antagonists, antioxidants, ACE inhibitors, IL-6 inhibitors, 11-beta hydroxylase inhibitors and angiotensin receptor blockers.

The application further provides a kit for the treatment of a fibrosis related disorder in a patient. The kit comprises one or more CRP antagonists and one or more SAP agonists that may be formulated to be conjointly administered. The SAP agonist in the kit may be selected from a small molecule, nucleic acid, or polypeptide. The SAP agonist in the kit may increase SAP signaling, mimic SAP signaling, increase SAP activity, increase SAP expression, increase serum SAP levels. In some embodiments, the SAP agonist in the kit may be a SAP polypeptide, an FcγR antibody (anti-FcγRI, anti-FcγRIIA, or anti-FcγRIII), a cross-linked anti-FcγR antibody (anti-FcγRI, anti-FcγRIIA, or anti-FcγRIII), an aggregated IgG antibody, or a cross-linked IgG antibody. The CRP antagonist in the kit may be selected from a small molecule, nucleic acid, or polypeptide. The CRP antagonist in the kit may decrease CRP signaling, decrease CRP activity, decrease CRP expression, decrease serum CRP levels, decrease production of IL-10, decrease production of TGF-β, or decrease CRP binding to FcγRI or FcγRIIA or FcγRIII. In some embodiments, the CRP antagonist in the kit may be an anti-CRP antibody, anti-FcγRI antibody, anti-FcγRIIA antibody, or anti-FcγRIII antibody. In some embodiments, the CRP antagonist in the kit may be selected from cyclooxygenase-2 inhibitors, anti-platelet agents, statins, inhibitors of cholesterol absorption, hypolipidemic agents, niacin, antidiabetic agents, β-adrenoreceptor antagonists, antioxidants, ACE inhibitors, IL-6 inhibitors, 11-beta hydroxylase inhibitors and angiotensin receptor blockers.

The application further provides methods for treating, preventing or reducing the severity of a fibrosis related disorder in a patient by determining the sequence of the polymorphic FcγRIIA allele and using said data to select a treatment plan that is most effective for the patient. The treatment plan may comprise the administration of an SAP agonist or CRP antagonist or combination thereof. Patients having a histidine at position 131 of one or both FcγRIIA alleles may be administered one or more SAP agonists, one or more CRP antagonist, or a combination thereof. A patient having arginine at position 131 of one or both FcγRIIA alleles may require a higher dose of a SAP agonist than a patient homozygous for the H131 allele.

The application further provides methods for conducting a diagnostic business. The methods comprise receiving a biological sample, measuring the concentration of CRP and SAP in the biological sample, and producing a report of the concentration of CRP and SAP. The concentration of CRP and SAP may be measured from plasma, healthy tissue, or fibrotic tissue and can be measured as total concentration or as free concentration, i.e., unbound, of CRP or SAP protein. In some embodiments, the methods further comprise determining the ratio of SAP-to-CRP and reporting said ratio.

The application further provides methods for determining data useful in the assessment of a patient's risk of developing a fibrosis related disorder. Assessment of risk is based on measuring the concentration of CRP in the biological sample. A second biological sample from a patient is assayed to determine the sequence of the polymorphic FcγRIIA allele. In some embodiments, the biological sample is measured for the concentration of SAP. The concentration of CRP and SAP may be measured from serum, plasma, healthy tissue, or fibrotic tissue and can be measured as total concentration or as free concentration, i.e., unbound, of CRP or SAP protein. In some embodiments, the ratio of SAP-to-CRP is determined.

The application further provides methods for determining the responsiveness to CRP in a PBMC or monocyte cell. The methods comprise culturing PBMC or monocytes with one or more concentrations of CRP and determining the degree of CRP induction of fibrocyte differentiation. In some embodiments, the CRP concentration is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. The degree of fibrocyte differentiation is indicative of the cell's responsiveness to CRP.

The application further provides methods for determining the responsiveness of a patient to the anti-fibrotic effects of CRP antagonists. The method comprises obtaining PBMC or monocyte cells from a patient, incubating these cells with one or more concentrations of CRP, and determining the degree of CRP induction of fibrocyte differentiation. In some embodiments, the CRP concentration is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. The degree of fibrocyte differentiation is indicative of the patient's responsiveness to CRP antagonists.

The application further provides methods for determining the minimum SAP-to-CRP ratio that prevents fibrocyte differentiation in a patient. The method comprises obtaining PBMC or monocyte cells from a patient and culturing these cells with one or more concentrations of CRP to determine the minimum CRP concentration that provides maximum stimulation of fibrocyte differentiation. In some embodiments, the CRP concentration is 0.001 µg/mL, 1.0 µg/mL, 5

µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. The method further comprises determining the minimum concentration of SAP that reduces fibrocyte differentiation by at least 90% in the presence of the minimum CRP concentration that provides maximum stimulation of fibrocyte differentiation. In some embodiments, the concentration of SAP is 0.001 µg/mL, 0.01 µg/mL, 0.1 µg/mL, 0.5 µg/mL, 1 µg/mL, 2 µg/mL, 3 µg/mL, 4 µg/mL, 5 µg/mL, 10 µg/mL, 15 µg/mL, 20 µg/mL, 25 µg/mL, 50 µg/mL, or 100 µg/mL. The indicated SAP concentration is then divided by the indicated CRP concentration to determine the minimum SAP-to-CRP ratio that prevents fibrocyte differentiation in vivo.

In some embodiments of the methods described herein, the fibrosis related disorder is not atherosclerosis.

In some embodiments of the methods described herein, the first and second biological samples are the same.

BRIEF DESCRIPTION OF THE DRAWINGS

FIG. 1. Amino acid sequence alignment of human (SEQ ID NO: 1, amino acids 20-223 of Genbank Accession No. NP_001630), *Gallus gallus* (SEQ ID NO: 2, amino acids 20-227 of Genbank Accession No. NP_001034653), *Bos taurus* (SEQ ID NO: 3, amino acids 20-224 of Genbank Accession No. AA102624), and *Cricetulus migratorius* (SEQ ID NO: 4, amino acids 20-223 of Genbank Accession No. AAB28726), serum amyloid P polypeptides (signal sequence not depicted). Amino acids identical to the human SAP are shaded.

FIGS. 3A-B. Fibrocyte Differentiation Assay for determining the effective SAP/CRP ratio to prevent fibrocyte differentiation in vivo. (A) The X-axis indicates the concentration of hSAP incubated with donor monocytes. The Y-axis indicates the amount of fibrocyte proliferation at day five as measured by the enumeration of fibrocytes per $5.0 \times 10^4$ cells. (B) The X-axis indicates the concentration of CRP incubated with donor monocytes, which were previously suspended in media containing 25 ng/mL hMCSF and 2 µg/mL hSAP. The Y-axis indicates the amount of fibrocyte proliferation as measured by the enumeration of fibrocytes per $5.0 \times 10^4$ cells.

FIGS. 5A-B. (A) CRP binding to sFcγRI. The data is a representative sensorgram of CRP binding to sFcγRI and indicates the on- and off-rates for binding of CRP. The Y-axis of the chart represents the surface plasma resonance units (RUs), and the X-axis represents time. The data is graphed as the change in mass at the cell surface with respect to time. Information on graph indicates time of sFcγRI and buffer injection and indicates the different concentrations of receptor assayed. (B) CRP binding to sFcγRIIIB. The data is a representative sensorgram of CRP binding to sFcγRIIIB and indicates the on- and off-rates for binding of CRP. The Y-axis of the chart represents the surface plasma resonance units (RUs), and the X-axis represents time. The data is graphed as the change in mass at the cell surface with respect to time. Information on graph indicates time of sFcγRI and buffer injection and indicates the different concentrations of receptor assayed.

FIGS. 6A-B. (A) Affinity of CRP binding to FcγRI. The Y-axis of the chart represents the response at equilibrium for binding of FcγRI to CRP as measured by surface plasma resonance units, and the X-axis represents the concentration of FcγRI. (B) Affinity of CRP binding to FcγRIIIB. The Y-axis of the chart represents the response at equilibrium for binding of CRP to FcγRIIIB as measured by surface plasma resonance units, and the X-axis represents the concentration of FcγRIIIB.

DETAILED DESCRIPTION OF THE INVENTION

Overview

Figure 2:
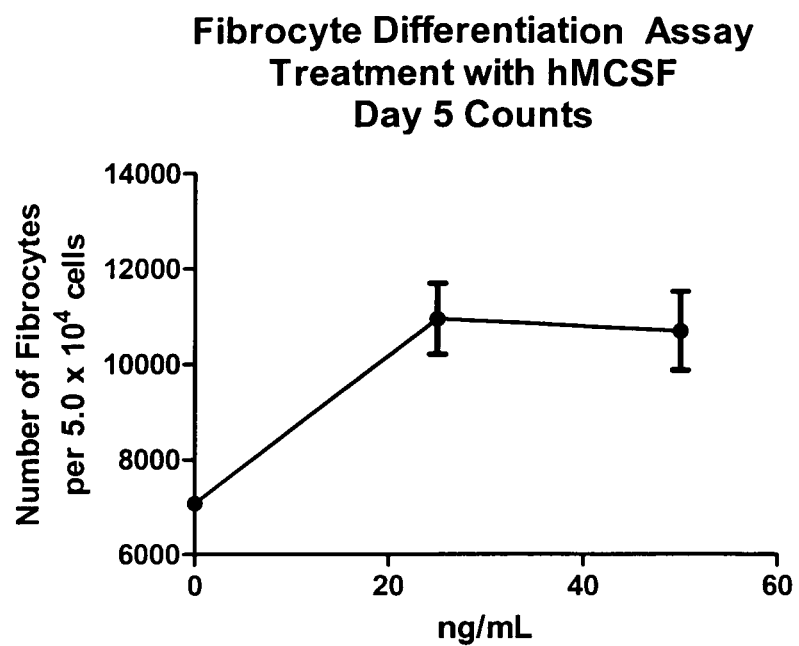
FIG. 2. Fibrocyte Differentiation Assay Treatment with hMCSF. The X-axis represents the concentration of hMCSF incubated with donor monocytes. The Y-axis indicates the amount of fibrocyte proliferation at day five as measured by the enumeration of fibrocytes per $5.0 \times 10^4$ cells.

Wound healing and the disregulated events leading to fibrosis both involve the proliferation and differentiation of fibroblasts and the deposition of extracellular matrix. Fibrocytes, fibrocyte precursors, myofibroblast precursors, and hematopoetic monocyte precursors make up a distinct population of fibroblast-like cells derived from peripheral blood monocytes that enter sites of tissue injury to promote angiogenesis and wound healing. Recently, it has been reported that CD14+ peripheral blood monocytes cultured in the absence of serum or plasma differentiate into fibrocytes within 72 hours, but that serum amyloid P (SAP) was able to inhibit fibrocyte, fibrocyte precursor, myofibroblast precursor, and/or hematopoetic monocyte precursor differentiation at levels similar to those found in plasma. In contrast, depleting SAP reduces the ability of plasma to inhibit fibrocyte, fibrocyte precursor, myofibroblast precursor, and/or hematopoetic monocyte precursor differentiation. Compared with sera from healthy individuals and subjects with rheumatoid arthritis, sera from subjects with scleroderma and mixed connective tissue disease, two systemic fibrotic diseases, were less able to inhibit fibrocyte, fibrocyte precursor, myofibroblast precursor, and/or hematopoetic monocyte precursor differentiation in vitro and had correspondingly lower serum levels of SAP. These results suggest that abnormally low levels of SAP may thus augment pathological processes leading to fibrosis. These data also suggest mechanisms to inhibit fibrosis in chronic inflammatory conditions, or conversely to promote wound healing.

As SAP binds to Fc receptors for immunoglobulin G (IgG; FcγRs), FcγR activation was subsequently demonstrated to be an inhibitory signal for fibrocyte, fibrocyte precursor, myofibroblast precursor, and/or hematopoetic monocyte precursor differentiation. FcγR are activated by aggregated IgG, and it has been shown that aggregated, but not monomeric, human IgG inhibits human fibrocyte, fibrocyte precursor, myofibroblast precursor, and/or hematopoetic monocyte precursor differentiation. Monoclonal antibodies that bind to FcγRI (CD64) or FcγRII (CD32) also inhibit fibrocyte, fibrocyte precursor, myofibroblast precursor, and/or hematopoetic monocyte precursor differentiation. Aggregated IgG lacking Fc domains or aggregated IgA, IgE, or IgM do not inhibit fibrocyte, fibrocyte precursor, myofibroblast precursor, and/or hematopoetic monocyte precursor differentiation. Incubation of monocytes with aggregated IgG, like SAP, inhibited fibrocyte, fibrocyte precursor, myofibroblast precursor, and/or hematopoetic monocyte precursor differentiation. Using inhibitors of protein kinase enzymes, it has also been shown that Syk- and Src-related tyrosine kinases participate in the inhibition of fibrocyte, fibrocyte precursor, myofibroblast precursor, and/or hematopoetic monocyte precursor differentiation. These observations suggest that fibrocyte, fibrocyte precursor, myofibroblast precursor, and/or hematopoetic monocyte precursor differentiation can occur in situations where SAP and aggregated IgG levels are low, such as after the restoration of hemostasis.

Serum amyloid P ("SAP") is a naturally-occurring serum protein in mammals composed of five identical subunits or protomers which are non-covalently associated in a disc-like molecule. SAP is a 125,000 Dalton pentameric glycoprotein composed of five, non-covalently linked, 25,000 Dalton protomers. SAP belongs to the pentraxin superfamily of proteins, characterized by this cyclic pentameric structure. The classical short pentraxins include SAP as well as C-reactive protein. (Osmand, A. P., et al., Proc. Nat. Acad. Sci., 74:739-743 (1977)) It is synthesized in the liver and the physiological half-life of human SAP is 24 hours. The sequence of the human SAP subunit is depicted in SEQ ID NO: 1 (amino acids 20-223 of Genbank Accession No. NP_001630, signal sequence not depicted).

C-reactive protein (also known as CRP and PTX1) is an essential human acute-phase reactant produced in the liver in response to a variety of inflammatory cytokines. Plasma CRP levels increase 1,000-fold in response to infection, ischemia, trauma, burns, and inflammatory conditions. The CRP protein binds to a broad range of cellular substances such as phosphocholine, fibronectin, chromatin, histones, and ribonucleoprotein in a calcium-dependent manner (Szalai et al., Immuno. Res., 1997, 16, 127-136). It is a ligand for specific receptors on phagocytic leukocytes, mediates activation reactions on monocytes and macrophages, and activates complement (Szalai et al., Immunol. Res., 1997, 16, 127-136).

The function of CRP is related to its role in the innate immune system. Similar to IgG, it activates complement, binds to Fc receptors and acts as an opsonin for various pathogens. Interaction of CRP with Fc receptors leads to the generation of anti-inflammatory cytokines that suppress the inflammatory response.

Current practitioners within the art have focused on the absolute levels of CRP or SAP in plasma or tissue and their individual roles in affecting inflammatory or fibrotic disease processes. In contrast, the current application discloses that CRP and SAP function to counterbalance each other's effects on inflammation and fibrosis. Low ratios of SAP-to-CRP in the plasma or tissues will result in lower ratios of SAP-to-CRP bound to FcγR and thereby increased production of TGFβ and other pro-fibrogenic cytokines and chemokines at sites of injury promoting fibrosis. Agents that increase this ratio by decreasing CRP levels or increasing SAP levels or decreasing CRP binding to FcγR or increasing SAP binding to FcγR will be effective therapeutics in slowing progression of or reversing fibrotic disease. Likewise, monitoring the ratio of SAP-to-CRP within individual populations should identify those at risk of developing a fibrosis related disorder and therefore of greater need for preventative therapy.

One aspect of the application relates, in part, on the surprising discovery that the polymorphisms of FcγRIIA that affect binding of CRP to FcγRIIA also affect the progression of fibrotic disease. A genetic polymorphism at the human FcγRIIA locus has been identified (NCBI refSNP rs 1801274) which affects binding of IgG2 and CRP to the FcγRIIA receptor on cells and the subsequent signaling. The polymorphism, known herein as the R131/H131 allele, is at amino acid 166, in the second Ig-like domain of FcγRIIA, as defined by Genebank Accession No. NP_067674 (SEQ ID NO: 6). For IgG2 binding, when an arginine is at this position (due to a G at the second position in the codon at position 535 of the mRNA sequence as defined by Genebank Accession No. NM_021642 (SEQ ID NO: 5)), the receptor binds IgG2 only very weakly, whereas when a histidine is at this position (due to an A at the second position in the codon at position 535 of the mRNA sequence), the receptor binds IgG efficiently.

CRP shares several functional activities with IgG, including opsonization, complement activation by binding C1q and binding to FcγRs. CRP is involved in host defense, regulation of inflammation and modulation of autoimmune disease. However, CRP binding to FcγRIIA appears efficient only for the R131 allele, with very little binding to the H131 allele, which is the exact opposite of IgG2 binding. Individuals heterozygous for this phenotype show an intermediate phenotype. CRP binding to the R131 allele results in the initiation of $Ca^{2+}$ signaling events.

Activation of PMNs and monocytes at inflammatory sites does not affect the selectivity of CRP for the R131 allele of human FcγRIIA. Individuals homozygous for the R131 allele of FcγRIIA are more efficient at responding to CRP-opsonized bacteria than individuals that are H131 homozygous, and this appears to enhance the early protective cytokine response to infection in these instances. It has been reported that CRP-mediated phagocytosis can occur when FcγRIIA is co-expressed with FcγRI and that this is more efficient with FcγRIIA R131 than with FcγRIIA H131 (Bodman-Smith et al, 2002, Immunology 107:252-260).

Within the context of lupus nephritis, there is an increased representation of FcγRIIA R131 in individuals with more advanced nephritis and with intense IgG2 deposition. CRP was found in renal immune deposits of these patients. FcγRIIA R131 may contribute to impaired removal of circulating immune complexes as well as effectively trigger phagocyte activation and the release of inflammatory mediators within glomeruli in these patients. Thus the genetic polymorphism at amino acid position 131 (residue 166 of SEQ ID NO: 6) in FcγRIIA affects how individuals signal CRP effects through FcγRs and these differences can lead to different responses that have potential to impact host defense, regulation of inflammation and modulation of autoimmune disease.

FcγRs are also receptors for the related pentraxin SAP, and SAP levels affect the biology of fibrosis. SAP binding to PBM cells blocks their ability to differentiate into pro-fibrotic fibrocytes. CRP binding to PBM cells has not been previously described to affect fibrocyte differentiation. The current application provides that CRP activates fibrocyte differentiation from PBM cells in a concentration-dependent manner, and that the ability of CRP to mediate this effect is dependent upon the R131 allele of FcγRIIA. The haplotype of FcγRIIA at amino acid position 131 (residue 166 of SEQ ID NO: 6) would therefore be expected to affect the contribution of CRP and SAP to FcγR signaling and consequently exert differential effects on fibrosis. Information in the NCBI SNP database (refSNP) regarding rs1801274 shows that the R131 allele of FcγRIIA is significantly represented in the human population. The R131 and H131 are essentially co-dominant. The genotype distribution documented in the NCBI database (which provides data on the genotype of several hundred individuals from a broad range of ethnic groups) is approximately 21% for R/R homozygotes, 47% for R/H heterozygotes and 32% for H/H homozygotes. As a population, Asian ethnics from Japan/China have a greater representation of the H/H genotype than other ethnic groups. Therefore, the haplotype of FcγRIIA at this locus would be expected to impact fibrosis and response to anti-fibrotic therapy within the human population in a significant manner.

Definitions

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a fibrotic or fibroproliferative disorder and/or adverse affect attributable to the disorder. "Treatment", as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "prevents" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals including humans. The term "mammal" includes primates, domesticated animals including dogs, cats, sheep, cattle, goats, pigs, mice, rats, rabbits, guinea pigs, captive animals such as zoo animals, and wild animals. As used herein the term "tissue" refers to an organ or set of specialized cells such as skin tissue, lung tissue, kidney tissue, and other types of cells.

The term "therapeutically effective amount" means an amount of therapeutic agents, or a rate of delivery of such therapeutic agents, effective to facilitate a desired therapeutic effect. The precise desired therapeutic effect will vary according to the fibrotic or fibroproliferative condition to be treated, the formulation to be administered, and a variety of other factors that are appreciated by those of ordinary skill in the art.

As used herein the term fibrosis related disorder refers to conditions involving fibrosis in one or more tissues. As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. As used herein the term "fibrosis" is used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called α-chains, which are wound around each other in a ropelike helix. Collagen exists in several forms or types; of these, type I, the most common, is found in skin, tendon, and bone; and type III is found in skin, blood vessels, and internal organs.

"Scleroderma" is a fibrosis related disorder characterized by a thickening and induration of the skin caused by the overproduction of new collagen by fibroblasts in skin and other organs. Scleroderma may occur as a local or systemic disease. Systemic scleroderma may affect a number of organs. Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. Pulmonary fibrosis affects 30 to 70% of scleroderma patients, often resulting in restrictive lung disease.

"Idiopathic pulmonary fibrosis" is a chronic, progressive and usually lethal lung disorder, thought to be a consequence of a chronic inflammatory process.

Treatment Methods

One aspect of the application provide methods for treating, preventing, or reducing the severity of fibrosis related disorders, the methods comprising measuring the concentration of CRP and SAP in a biological sample from a patient in order to determine an SAP-to-CRP ratio. The determined ratio is compared to one or more SAP-to-CRP reference ratios and an anti-fibrotic therapy is administered to a patient having an SAP-to-CRP ratio that is lower that one or more reference ratios.

In some embodiments, a biological sample from a patient is compared to an SAP-to-CRP reference ratio determined from a biological sample from a healthy subject or a reference ratio determined from the mean ratio of a population of healthy subjects. In some embodiments, the reference ratio is determined from the mean ratio of a population of subjects with similar patient characteristics such as age and gender. In some embodiments, anti-fibrotic therapy is administered to a patient having an SAP-to-CRP ratio that is at least 10, 20, 30, 40, 50, 70, or 100% lower than a reference ratio. In some embodiments, anti-fibrotic therapy is administered to a patient having an SAP-to-CRP ratio that is less than 25, 20, 15, 10, or 5. In some embodiments, the SAP-to-CRP reference ratio is 60, 50, 40, 30, 20, 15, 10, or 5. Physicians having knowledge of a patient's SAP-to-CRP ratio would be able to more accurately adjust dosage of SAP or other anti-fibrotic therapy to an appropriate level for an individual patient.

In some embodiments, the SAP and CRP concentrations are determined from biological samples from the same type of tissue or cellular material. In certain embodiments, the SAP-to-CRP ratio determined from a biological sample obtained from fibrotic tissue from a patient is compared to a non-fibrotic biological sample from the same patient. In some embodiments, the non-fibrotic biological sample is from the same tissue as the fibrotic biological sample. In some embodiments, the biological sample is blood serum or plasma.

The plasma concentration of SAP can be determined by, for example, performing ELISA assays on sera using commercially available SAP antibodies (e.g., Alpha Diagnostic International Cat #SAP12-S) as described in Pilling, D. J of Immunology, 171: 5537-5546 (2003). The plasma concentration of CRP can be determined using commercially available kits including Human C-Reactive Protein (CRP) ELISA Kits from Alpha Diagnostic International Cat #1000 and Chemicon Cat #CYT298. Additionally, Luminex™ based cytometric bead array assays have been developed for SAP and CRP and are offered by Rules Based Medicine™. The average plasma concentration of SAP in a healthy subject is between 20-40 µg/ml. The average plasma concentration of CRP in a healthy subject is between 0-2 µg/ml. In some embodiments, the SAP and CRP concentrations measured are "free concentration", or rather the concentration of unbound SAP and CRP. Determination of free concentration of SAP and CRP can be performed, e.g., using sandwich ELISA assays. For example, a first antibody that recognizes the FcγR binding site of SAP is used to capture SAP from a biological sample. A second antibody that recognizes the ligand binding site of SAP is then used to detect the free concentration of SAP in the sample.

In some embodiments, methods may further comprise a step of assaying a second biological sample to determine the amino acid at the 131 allele of FcγIIA. In some embodiments, anti-fibrotic therapy is administered to an R131 homozygous patient having an SAP-to-CRP ratio that is at least 5, 10, 20, 30, 40, 50, 70, or 100% lower than a reference ratio. In some embodiments, the SAP-to-CRP reference ratio is 60, 50, 40, 30, 20, 15, 10, or 5. In some embodiments, anti-fibrotic therapy is administered to an R131 homozygous patient having an SAP-to-CRP ratio that is less than 25, 20, 15, 10, or 5. In some embodiments, anti-fibrotic therapy is administered to an H131 homozygous patient having an SAP-to-CRP ratio that is at least 5, 10, 20, 30, 40, 50, 70, or 100% lower than a reference ratio. In some embodiments, the SAP-to-CRP reference ratio is 60, 50, 40, 30, 20, 15, 10, or 5. In some embodiments, anti-fibrotic therapy is administered to an H131 homozygous patient having an SAP-to-CRP ratio that is less than 25, 20, 15, 10, or 5. In some embodiments, anti-fibrotic therapy is administered to an H131/R131 heterozygous patient having an SAP-to-CRP ratio that is at least 5, 10, 20, 30, 40, 50, 70, or 100% lower than a reference ratio. In some embodiments, the SAP-to-CRP reference ratio is 60, 50, 40, 30, 20, 15, 10, or 5. In some embodiments, anti-fibrotic therapy is administered to an H131/R131 heterozygous patient having an SAP-to-CRP ratio that is less than 25, 20, 15, 10, or 5.

While not wishing to be bound by theory, the underlying genetic polymorphism of the FcγRIIA allele will affect the ability of the SAP/CRP ratio to accurately predict the anti-fibrotic therapy response. Individuals homozygous for the H131 allele of FcγRIIA would be predicted to be less responsive to CRP and therefore CRP would be less likely to buffer the anti-fibrotic effects of SAP. H131 homozygous individuals may therefore be more sensitive to the anti-fibrotic effects of SAP, or SAP agonists, and less sensitive to the anti-fibrotic effects of other agents that function through a CRP inhibitory mechanism, or CRP antagonists. R131 homozygous individuals are also sensitive to SAP, but an effective treatment dosage of SAP, or SAP agonists, will be dependent on CRP levels. The dosage of SAP, or SAP agonists, will need to be increased for effective treatment in patients that are R131 homozygous and have high CRP levels.

In some embodiments, methods for determining the FcγRIIA allelic pattern in an individual patient may include, e.g., 1) immunological detection of one or more allelic forms of FcγRIIA polypeptides present on the surface of appropriate immune cells, i.e., "phenotypic characterization"; or 2) molecular detection of the DNA or RNA encoding one or more FcγRIIA allelic forms using, e.g., nucleic acid probes, with or without nucleic acid amplification or sequencing, i.e., "genotypic characterization".

In some embodiments, determination of SAP-to-CRP ratio or measurement of CRP levels in combination with identification of the FcγRIIA polymorphism will be used as a diagnostic tool for selecting an anti-fibrotic therapy and dosing. Physicians having knowledge of a patient's SAP-to-CRP ratio and both 131 alleles of the FcγRIIA will be able to more accurately adjust dosage of SAP or other anti-fibrotic therapy to an appropriate level for the individual patient.

In some embodiments, the second biological sample used to determine the polymorphic allele of FcγRIIA is the same or different than the first biological sample used to assay for SAP and/or CRP concentration. The biological sample may be from serum, plasma, healthy tissue, or fibrotic tissue from which cells, FcγRIIA protein, and/or nucleic acid (mRNA or genomic DNA) can be extracted.

Another aspect of the application provides methods for adjusting the treatment of a fibrosis related disorder in a patient, the methods comprising measuring the concentration of CRP and SAP in a patient in order to determine an SAP-to-CRP ratio, comparing the ratio to one or more SAP-to-CRP reference ratios, administering an anti-fibrotic therapy to a patient having an SAP-to-CRP ratio that is lower that one or more reference ratios, and further measuring the concentration of CRP and SAP in a patient in order to determine a second SAP-to-CRP ratio. The anti-fibrotic therapy is adjusted based on the second SAP-to-CRP ratio.

The subsequent measurement of CRP and SAP concentrations in the patient may occur at any time after the initiation of the anti-fibrotic therapy. The measurement may be performed during the course of the anti-fibrotic therapy or after its completion. CRP and SAP concentrations may be determined multiple times and the ratios calculated throughout the treatment schedule as well as subsequent to treatment as part of follow-up care.

The target ratio of SAP-to-CRP will depend on a variety of factors including the sex and disease state of a patient. It is within the purview of one skilled in the art in view of the present disclosure, to determine the target ratio for an individual patient. In some embodiments the SAP-to-CRP target ratio is at least 2, 5, 7, 10, 12, 14, 16, 18, 20, 30, 40, 50, 60 or greater.

The anti-fibrotic therapy may be adjusted, for example, by dosage, frequency of dosage, or by changing the anti-fibrotic agent administered. For example, one skilled in the art may reduce the dosage in a patient who has reached the SAP-to-CRP target ratio, while increasing the dosage for a patient whose SAP-to-CRP ratio has not significantly increased. The SAP-to-CRP ratio therefore provides a medical practitioner with an objective indication of a patient's response to treatment. In some embodiments, one skilled in the art may continue administering the anti-fibrotic therapy to a patient who no longer presents gross fibrotic symptoms, based on the patient's SAP-to-CRP ratio.

Another aspect of the application provides a method to determine whether a patient is at risk for developing a fibrosis related disorder, the method comprising measuring the concentration of CRP and SAP in a patient to determine an SAP-to-CRP ratio, comparing the determined SAP-to-CRP ratio with one or more reference ratios, and interpreting an SAP-to-CRP that is lower than one or more reference ratios as an indication that the patient is at risk for a fibrosis related disorder. In some embodiments, methods may further comprise a step of assaying a second biological sample to determine the amino acid at the 131 allele of FcγIIA.

Typically, the greater the deviation of the ratio in the individual patient from that of the reference ratio, the greater the risk for development of a fibrosis related disorder. In some embodiments, an SAP-to-CRP ratio that is at least 5, 10, 20, 40, 60, 80, or 100% lower than a reference ratio is an indication that the patient is at risk. In some embodiments, an SAP-to-CRP ratio that is less than 25, 20, 15, 10, or 5 is an indication that the patient is at risk. In some embodiments, the SAP-to-CRP reference ratio is 60, 50, 40, 30, 20, 15, 10, or 5.

Once a patient has been identified as at risk, suitable preventive and precautionary measures may be taken, such as commencing treatment with an anti-fibrotic therapy.

In some embodiments, the patient may present additional risks for a fibrosis related disorder including chemotherapy, radiation therapy, as well as suffering from various injuries or burns. In these cases, only a small deviation of an individual's SAP-to-CRP ratio from that of a reference ratio, in combination with the presence of additional risk factors, may indicate that the patient is at high risk of developing a fibrosis related disorder. In some embodiments, an SAP-to-CRP ratio that is at least 2, 5, 10, 20, 40, 60, 80, or 100% lower than a reference ratio is an indication that the patient with one or more additional risk factors is at risk.

One such additional risk factor is the presence of a arginine at amino acid position 131 at one or both alleles of the FcγRIIA polymorphism (position 166 of SEQ ID NO: 6). In some embodiments, the presence of the R131 allele increases the patient's risk for developing a fibrosis related disorder. In some embodiments, the identification of the FcγRIIA polymorphism will determine the most appropriate anti-fibrotic therapy for a patient.

Another aspect of the application provides for a method of diagnosing fibrosis related disorder, the method comprising measuring the concentration of CRP and SAP in a patient to determine an SAP-to-CRP ratio, comparing the determined SAP-to-CRP ratio with one or more reference ratios, and diagnosing fibrosis related disorder in a patient having an SAP-to-CRP ratio that is lower than a reference ratio. In some embodiments, an SAP-to-CRP ratio that is at least 5, 10, 20, 40, 60, 80, 100, or 150% lower than a reference ratio is interpreted as a positive diagnosis for a fibrosis related disorder. In some embodiments, the SAP-to-CRP reference ratio is 60, 50, 40, 30, 20, 15, 10, or 5.

Another aspect of the application provides methods for treating fibrosis related disorders by the conjoint administration of one or more CRP antagonists and one or more SAP agonists. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can benefit from a combined effect of different therapeutic compounds.

Another aspect of the application provides kits for treating fibrosis related disorders that comprise one or more CRP antagonists and one or more SAP agonists. The antagonists and agonists are formulated to be administered conjointly. The compounds may be administered separately or in a combined formulation. The compounds may also be administered simultaneously or at different dosing schedules.

In some embodiments, the SAP agonist in the kit is selected from a small molecule, nucleic acid, or polypeptide. The SAP agonist in the kit may increase SAP signaling, mimic SAP signaling, increase SAP activity, increase SAP expression, or increase serum SAP levels. In certain embodiments, the SAP agonist in the kit is a SAP polypeptide, an FcγR antibody (anti-FcγRI, anti-FcγRIIA, or anti-FcγRIII), a cross-linked anti-FcγR antibody (anti-FcγRI, anti-FcγRIIA, or anti-FcγRIII), an aggregated IgG antibody, or a cross-linked IgG antibody. In some embodiments, the CRP antagonist in the kit is selected from a small molecule, nucleic acid, or polypeptide.

In some embodiments, the CRP antagonist in the kit may decrease CRP signaling, decrease CRP activity, decrease CRP expression, decrease serum CRP levels, decrease production of IL-10, decrease production of TGF-β, or decrease CRP binding to FcγRI or FcγRIIA or FcγRIII. In certain embodiments, the CRP antagonist in the kit is an anti-CRP antibody, anti-FcγRI antibody, anti-FcγRIIA antibody, or anti-FcγRIII antibody. In certain embodiments, the CRP antagonist in the kit is selected from cyclooxygenase-2 inhibitors, anti-platelet agents, statins, inhibitors of cholesterol absorption, hypolipidemic agents, niacin, antidiabetic agents, β-adrenoreceptor antagonists, antioxidants, ACE inhibitors, IL-6 inhibitors, 11-beta hydroxylase inhibitors and angiotensis receptor blockers.

Another aspect of the application provides methods for treating a fibrosis related disorder comprising identifying a patient afflicted with a fibrosis related disorder, measuring the CRP concentration in a biological sample from the patient, determining if the concentration is higher than one or more reference values and administering a CRP antagonist to a patient having a CRP concentration higher than a reference value.

In some embodiments, the CRP concentrations measured is "free concentration", or rather the concentration of unbound CRP. In certain embodiments, a biological sample from a patient is compared to a CRP reference value determined from a biological sample from a healthy subject or a reference value derived from a population of healthy subjects. In certain embodiments, the reference value is derived from a population of subjects with similar patient characteristics such as age and gender. In some embodiments, the CRP reference value is 0.1 µg/ml, 0.5 µg/ml, 1 µg/ml, 3 µg/ml, 10 µg/ml or 20 µg/ml.

Another aspect of the application provides methods for conducting a diagnostic business. The method comprises receiving a biological sample, measuring the concentration of CRP and/or SAP from the biological sample, and producing a report of the concentration of CRP and/or SAP. The concentration of CRP and SAP may be measured from serum, plasma, healthy tissue, or fibrotic tissue and can be measured as total concentration or as free concentration, or unbound, of CRP or SAP protein. The report produced may be sent to the patient or a healthcare provider. The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's. In some embodiments, the method further comprises determining and reporting the ratio of SAP-to-CRP in the biological sample.

Another aspect of the application provides methods for determining data useful in the assessment of a patient's risk of developing a fibrosis related disorder, the method comprising obtaining a biological sample from a patient, measuring the concentration of CRP in the biological sample, and determining the amino acid at position 131 for both alleles of the FcγRIIA polymorphism (position 166 of SEQ ID NO: 6). The biological sample may be from serum, plasma, healthy tissue, or fibrotic tissue from which cells, FcγRIIA protein, and/or nucleic acid (RNA or genomic DNA) can be extracted. In some embodiments, the method further comprises determining the concentration of SAP in a biological sample. The concentration of CRP and SAP may be measured from plasma, healthy tissue, or fibrotic tissue and can be measured as total concentration or as free concentration, or unbound, of CRP or SAP protein. In some embodiments, the concentration of SAP and CRP will be used to determine the SAP-to-CRP ratio. This data provides a medical practitioner with an objective indication of a patient's risk for developing a fibrotic disorder and is an indication of a patient's response to anti-fibrotic treatment. In some embodiments, one skilled in the art may determine the most appropriate anti-fibrotic therapy to administer a patient based on this risk assessment.

Another aspect of the application provides methods for treating, preventing or reducing the severity of a fibrosis related disorder comprising analyzing a biological sample from a patient for a polymorphism of the FcγRIIA allele. The methods comprise determining the amino acid residue at position 131 polymorphism (position 166 of SEQ ID NO: 6) in both FcγRIIA alleles of a patient and selecting a treatment plan that is most effective for the patient. Patients having a histidine at position 131 of one or both FcγRIIA alleles may be administered one or more SAP agonists. Patients having an arginine at position 131 of one or both FcγRIIA alleles may be administered one or more SAP agonists, one or more CRP antagonist, or combination thereof. A patient having arginine at position 131 for one or both FcγRIIA alleles may require the administration of a higher dose of a SAP agonist than a patient homozygous for the H131 allele. The dosage of a SAP agonist will be dependent on the CRP concentration in a patient. Patients homozygous for R131 with a high level of plasma CRP are administered higher doses of a SAP agonist for effective treatment.

The FcγRIIA polymorphisms described herein are also useful for improving many different aspects of the drug development process for anti-fibrotic treatments. For instance, an aspect of the present invention includes selecting individuals for clinical trials based on FcγRIIA 131 polymorphism. For example, individuals with at least one H131 allele indicate that they are likely to positively respond to a SAP polypeptide or SAP agonist and can be included in trials evaluating the effect of SAP treatment. Alternatively, individuals with at least one R131 allele may also be included in SAP based clinical trials; however, the individuals may require a higher dosage of SAP.

Another aspect of the application provides methods for determining the responsiveness of PBMC or monocyte cells to CRP for fibrocyte differentiation. In some embodiments, the cells may be obtained from various tissue culture lines. In some embodiments, the method comprises obtaining a biological sample from a patient that contains PBMC or monocyte cells. The biological sample may be from serum, plasma, healthy tissue, or fibrotic tissue. The cells are cultured in media with various concentrations of CRP to determine the degree of fibrocyte differentiation. The concentration of CRP can range from 0.0001 µg/mL to 1 mg/ml, and in some embodiments is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. In some embodiments of this assay, the media may be supplemented with between 1-100 ng/ml hMCSF; the preferred concentration of hMCSF being 25 ng/mL. The indication that PBMC and monocytes have differentiated into fibrocytes can be determined by one skilled in the art. In general, fibrocytes are morphologically defined as adherent cells with an elongated spindle-shape and the presence of an oval nucleus. In some embodiments of this assay, cells are fixed and stained with Hema 3 stain before enumerating fibrocytes by direct counting using an inverted microscope. The amount of fibrocyte differentiation is interpreted by one skilled in the art as an indication of a cell's responsiveness to CRP. The greater the amount of fibrocyte differentiation indicates a greater degree of CRP responsiveness.

Another aspect of the application provides methods for determining the responsiveness of patient to the anti-fibrotic effects of CRP antagonist. The method comprises obtaining a biological sample from a patient that contains PBMC or monocyte cells. The biological sample may be from serum, plasma, healthy tissue, or fibrotic tissue. The cells are cultured in media with various concentrations of CRP to determine the degree of fibrocyte differentiation The concentration of CRP can range from 0.0001 µg/mL to 1 mg/ml, and in some embodiments is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. In some embodiments of this assay, the media may be supplemented with between 1-100 ng/ml hMCSF; the preferred concentration of hMCSF being 25 ng/mL. The indication that PBMC and monocytes have differentiated into fibrocytes is determined by one skilled in the art. In general, fibrocytes are morphologically defined as adherent cells with an elongated spindle-shape and the presence of an oval nucleus. In some embodiments of this assay, cells are fixed and stained with Hema 3 stain before enumerating fibrocytes by direct counting using an inverted microscope. The amount of fibrocyte differentiation is interpreted by one skilled in the art as an indication of a patient's responsiveness to CRP. The greater the amount of fibrocyte differentiation indicates a greater degree of CRP responsiveness in the patient.

Another aspect of the application provides methods for determining the minimum SAP-to-CRP ratio that prevents fibrocyte differentiation in a patient. The method comprises obtaining a biological sample from a patient that contains PBMC or monocyte cells. The biological sample may be from serum, plasma, healthy tissue, or fibrotic tissue. The cells are cultured in media with various concentrations of CRP to determine the minimum concentration of CRP that provides the maximum induction of fibrocyte differentiation. The concentration of CRP can range from 0.0001 µg/mL to 1 mg/ml, and in some embodiments is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. Additional PBMC or monocyte cells obtained from a patient are then cultured in media supplemented with this minimum concentration of CRP and various concentrations of SAP. The concentration of CRP can range from 0.0001 µg/mL to 1 mg/ml, and in some embodiments is 0.001 µg/mL, 1.0 µg/mL, 2 µg/mL, 3 µg/mL, 4 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. In this assay, the cells are monitored to determine the minimum concentration of SAP necessary to reduce fibrocyte differentiation by at least 90% in the presence of CRP. The indicated SAP concentration is then divided by the indicated CRP concentration to determine the minimum SAP-to-CRP ratio that prevents fibrocyte differentiation in vivo. In some embodiments of this assay, the media is supplemented with between 1-100 ng/ml hMCSF; the preferred concentration of hMCSF being 25 ng/mL. The indication that PBMC and monocytes have differentiated into fibrocytes can be determined by one skilled in the art. In general, fibrocytes are morphologically defined as adherent cells with an elongated spindle-shape and the presence of an oval nucleus. In some embodiments of this assay, cells are fixed and stained with Hema 3 stain before enumerating fibrocytes by direct counting using an inverted microscope.

Fc-Receptors

Receptors for immunoglobulins (Fc-receptors or FcRs) are widely expressed throughout the immune system. By binding to the antibody Fc-portion, they provide a link between the specificity of the adaptive immune system and the effector functions triggered by innate immune effector cells. Co-expression of activating and inhibitory FcRs on the same cell establishes a threshold for immune cell activation by immune complexes (combination of an epitope with an antibody directed against that epitope). Besides their involvement in the efferent phase of an immune response, they are also important for modulating adaptive immune responses by regulating B cell and dendritic cell (DC) activation. Uptake of immune complexes by FcRs on DCs and the concomitant triggering of activating and inhibitory signaling pathways will determine the strength of the initiated T-cell response. Loss of this balanced signaling results in uncontrolled responses that can lead to the damage of healthy tissues and ultimately to the initiation of autoimmune processes.

FcRs are widely expressed on cells of the immune system and select other cell types, such as endothelial cells, mesangial cells, and osteoclasts; one of the few hematopoietic cell types that do not show notable FcR expression are T cells. Four different classes of FcRs have been identified in rodents: FcγRI, FcγRIIB, FcγRIII, and FcγRIV. FcγRs are well conserved between different mammals and orthologous proteins to these rodent receptors were found in most species. The corresponding human proteins are called FcγRIA, FcγRIIB (CD32B), FcγRIIA (CD32A), FcγRIIC, FcγRIIIA (CD16), and FcγRIIIB. Although the extracellular portion of FcγRIIA is highly homologous to mouse FcγRIII, the intracellular portion differs significantly. Other human FcR genes such as FcγRIB and FcγRIC do not code for functional proteins due to disrupted open reading frames. In addition, FcγRIIIB, a GPI-anchored FcR selectively expressed on neutrophils, is not found in mice.

On a functional level, FcRs can be classified in two ways: first, based on the affinity for their ligand and second, based on the type of signaling pathway that is initiated on FcR cross-linking. The majority of FcRs including FcγRIIB, FcγRIII, and FcγRIV as well as their corresponding human counterparts FcγRIIA/B/C and FcγRIIIA/B have a low affinity for the IgG Fc-portion in the micromolar range ($10^{-5}$ to $10^{-7}$). Only FcγRI displays a higher affinity ($10^8$-$10^9$ M$^{-1}$) enabling significant binding to monomeric antibodies. All other FcRs selectively interact with antibodies in the form of immune complexes, which usually consist of multiple antibodies bound to their target antigen. FcRs differ in regard to the signaling pathways they initiate. The activating receptors (FcγRI, FcγRIIA and FcγRIIIA) contain an Immunoreceptor Tyrosine-based Activation Motif (ITAM) in their cytoplasmic region or in their associated signal transduction region. They stimulate immune effector cell activation/proliferation, release of inflammatory mediators, oxidative burst, phagocytosis and antigen presentation. The inhibitory receptors (FcγRIIB1 and FcγRIIB2) contain an Immunoreceptor Tyrosine-based inhibitory Motif (ITIM) in their cytoplasmic tail. In cells expressing both receptor classes, the immune response depends on the ratio between activating and inhibiting receptors, and hence on the cytokine environment. Th1 and Th2 cytokines up-regulate the expression of activating and inhibitory receptors respectively.

All of these "activating" FcRs contain ITAM in their cytosolic portion that become tyrosine-phosphorylated by members of the Src family of kinases. Phosphorylation of the ITAM sequences creates SH2 sites for docking and activation of Syk kinases. Depending on the cell type and individual FcR, the involved Src kinase family members might vary. For example, Lyn is associated with the FcγRI pathway in mast cells, whereas Lck is associated with FcγRIIIA in NK cells. In macrophages both of these kinases, as well as Hck, are associated with FcγRI and FcγRIIA (Takai, 2002). Following the phosphorylation of the ITAM motif, the recruitment and activation of Syk kinases ensues that leads to the recruitment of a variety of intracellular substrates, including PI3K, Btk and other Tec family kinases, phospholipase C-γ (PLCγ), and adaptor proteins such as SLP-76 and BLNK. Moreover, the Ras/Raf/MAP kinase pathway is activated through Sos bound to Grb2 that is recruited on phosphorylation of Shc. Another crucial step is the activation of PI3K by Syk, which results in the generation of phosphatidyl-inositol-3-phosphates. This leads to the recruitment of Btk and PLCγ that recognize PIP3 with their pleckstrin homology (PH) domains leading to the production of inositol triphosphate (IP3) and diacylglycerol (DAG), which are crucial for the mobilization of intracellular calcium and activation of protein kinase C (PKC). This signaling cascade initiates inflammatory, cytolytic and phagocytic activities of immune effector cells.

The role of the inhibitory receptor signaling is to dampen these activating pathways by interfering with the generation of key intermediates such as PIP3. This is initiated by phosphorylation of the ITIM motif in the cytosolic portion of FcγRIIB by Lyn that leads to the recruitment and activation of the SH2-domain containing inositol phosphatase (SHIP). The key function of activated SHIP is to hydrolyze phosphatidyl inositol intermediates, such as PIP3, and thereby to interfere with the membrane recruitment of Btk and PLCγ, thus dampening ITAM signaling mediated calcium release and downstream effector functions such as ADCC, phagocytosis, cytokine secretion, and release of inflammatory mediators. The Ras pathway is also inhibited by recruitment of Shc and DOK to tyrosine-phosphorylated SHIP, which inhibits cell proliferation.

Polymorphism R131/H131 of FcγRIIA

An allelic polymorphism in the human FcγRII (FcγRIIA) gene that consists of a single base substitution, guanine (G) to adenine (A), at nucleotide 494 of the coding region in exon 4 (Stuart et al., 1887; Brooks et al., 1989; Seki, 1989) that results in an amino acid change from arginine (R) to histidine (H) at position 131 of the second extracellular domain has been previously described (Clark et al., 1989; Warmerdam et al., 1990; Tate et al. 1992). As used herein, the polymorphism at position "131" of human FcγRIIA refers to position 166 in the immature protein (SEQ ID NO: 6) and position 133 in the mature protein. Historically, there has been conflicting nomenclature regarding the amino acid position of this FcγRIIA polymorphism that requires further clarification. The protein sequence listed in the NCBI database under NP_067674 represents the immature form of FcγRIIA, which is synthesized with a signal peptide sequence that is then cleaved off during transport of the receptor protein to the cell surface (SEQ ID NO:6). The final protein receptor at the cell surface is known as the mature protein. The signal sequence for human FcγRIIA is described as the first 33 amino acids of the immature protein in the NCBI database sequence with accession number P12318. Removal of the signal sequence changes the amino acid position of the Arg/His at 166 in the immature protein (see SEQ ID NO: 6) to Arg/His at 133 in the mature, functional protein. The mature FcγRIIA was initially identified as amino acid 1 of the mature protein sequence and as amino acid 34 of the immature protein sequence (correction is established in Powell et al, 1999). The identification and naming of the R131/H131 polymorphism occurred during the time period before this correction in the exact N-terminus of human FcγRII was made (Warmerdam et al., 1990). Verification that the R131/H131 polymorphism occurs at mRNA position 535 as in defined NM_021642 (SEQ ID 5) can also be obtained by reference to Flesch et al. 1998. This journal article defines a method for rapid typing of the R131/H131 human FcγRIIA polymorphism using PCR with allele-specific primers. This polymorphism can also be defined by a SNP described in Genebank Accession No. SNP re1801274 (SEQ ID NO: 7), wherein the nucleotide at position 301 of the antisense strand can be a C or an T. It is known to one skilled in the art that the antisense strand can be used to interpret the coding strand in which the polymorphism would be an A or G in the FcγRIIA reading frame. Applicants will use the nomenclature position 131 when referring to the arginine/histidine polymorphism.

The 131 polymorphism alters the affinity of the receptor for at least three IgG subclasses, namely, murine (m) IgG1, human (h) IgG2 and hIgG3. The polymorphism was originally defined by differences in the binding of mIgG1 anti-CD3 mAb to FcγRII of human monocytes in a T cell mitogenesis assay. The allelic form with R at amino acid 131 expressed high affinity for mIgG1 whereas the form with H131 showed low affinity, conferring high and low functional responses, respectively. Heterozygous cells were reported to be fully or variably responsive. Subsequent studies of receptors expressed in transfectants found that the H131 form manifested high affinity for hIgG2, whereas the R131 genotypic form bound little or no hIgG2. Binding assays using monocytes confirmed this result and showed furthermore that the H131 form bound hIgG3 significantly better than the R131 form of FcγRIIA.

Recent data suggest that this polymorphism may be relevant to FcγRII function in health and disease, especially in situations where hIgG2 is the predominant antibody subclass produced, such as in anti-carbohydrate immune response (Insel and Anderson, 1988). Polymorphonuclear neutrophils (PMN) homozygous for H131 show greater capacity to phagocytose bacteria or erythrocytes opsonized with hIgG2 than do PMN homozygous for R131 (Salmon et al, 1992; Sanders et al 1994). This polymorphism may also be implicated in the susceptibility to heparin-induced thrombocytopenia (HIT), a disorder associated with anti-platelet heparin-dependent antibodies that cluster and trigger the platelet FcγRII (Cines et al. 1980; Chong et al, 1982, Isenhart et al, 1994; Kelton et al 1988; Chong et al, 1989). Moreover, the frequency of individuals homozygous for H131 appears underrepresented in a group of patients with recurrent bacterial infections and in a group susceptible to meningococcal disease (Sanders et al 1994; Fijen et al 1993). Additionally, the level of circulating hIgG2 is significantly lower in H/H131 individuals as compared to those with the R/R131 genotype (Parren et al, 1992).

A "polymorphism" as used herein denotes a variation in the nucleotide sequence of a gene in an individual. Genes that have different nucleotide sequences as a result of a polymorphism are "alleles". A "polymorphic position" is a predetermined nucleotide position within the sequence. In some cases, genetic polymorphisms are reflected by an amino acid sequence variation, and thus a polymorphic position can result in location of a polymorphism in the amino acid sequence at a predetermined position in the sequence of a polypeptide. An individual "homozygous" for a particular polymorphism is one in which both copies of the gene contain the same sequence at the polymorphic position. An individual "heterozygous" for a particular polymorphism is one in which the two copies of the gene contain different sequences at the polymorphic position.

Identification of the R131/H131 FcγRIIA Polymorphism in a Biological Sample.

The present application is based, in part, on the finding that the 131 polymorphism in the gene encoding the human FcγRIIA receptor isoform has an effect on fibrotic disease risk, progression, and/or treatment. In some embodiments, the present application provides methods for determining the allelic pattern of FcγRIIA genes in human patients. The methods encompass the use of allele-specific oligonucleotides as hybridization probes and/or as primers for DNA amplification, as well as the use of direct DNA sequencing. Identification of receptor alleles may also be achieved immunologically, by contacting blood cells that express FcγRIIA receptors on their cell surface with antibodies that distinguish between different polymorphic forms of the receptor.

In some embodiments, white blood cells or subsets thereof are isolated from a patient to be tested using methods that are well known in the art, such as, for example, gradient centrifugation and/or immunoadsorption. Antibodies that are capable of distinguishing between different allelic forms of FcγRIIA are then applied to the isolated cells to determine the presence and relative amount of each allelic form. The antibodies may be polyclonal or monoclonal, preferably monoclonal. Measurement of specific antibody binding to cells may be accomplished by any known method, including without limitation quantitative flow cytometry, or enzyme-linked or fluorescence-linked immunoassay. The presence or absence of a particular allele, as well as the allelic pattern (i.e. homozygosity vs. heterozygosity) is determined by comparing the values obtained from the patient with norms established from populations of patients of known genotypes.

In some embodiments, DNA is obtained from a patient, and the presence of DNA sequences corresponding to particular FcγRIIA alleles is determined. The DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection, inflammation or fibrosis. DNA is extracted from the cell source or body fluid using any of the numerous methods that are standard in the art. It will be understood that the particular method used to extract DNA will depend on the nature of the source.

Once extracted, the DNA may be employed without further manipulation. Alternatively, the DNA region corresponding to all or part of the FcγRIIA may be amplified by PCR or other amplification methods known in the art. In this case, the amplified regions are specified by the choice of particular flanking sequences for use as primers. Amplification at this step provides the advantage of increasing the concentration of FcγRIIA DNA sequences. The length of DNA sequence that can be amplified ranges from 80 bp to up to 30 kbp. Preferably, primers are used that define a relatively short segment containing sequences that differ between different allelic forms of the receptor.

The presence of FcγRIIA allele-specific DNA sequences may be determined by any known method, including without limitation direct DNA sequencing, hybridization with allele-specific oligonucleotides, and single-stranded conformational polymorphism (SSCP). Direct sequencing may be accomplished by chemical sequencing, using the Maxam-Gilbert method, or by enzymatic sequencing, using the Sanger method. In the latter case, specific oligonucleotides are synthesized using standard methods and used as primers for the dideoxynucleotide sequencing reaction. An alternate method of determining the FcγRIIA allele in a patient uses PCR primers that differentially recognize the 131 polymorphism. This method is described in detail in example 5 and can be used to distinguish between the H131/R131 alleles without sequencing the DNA.

In some embodiments, cells expressing FcγRIIA are isolated by immunoadsorption, and RNA is isolated from the immunopurified cells using well-known methods such as guanidium thiocyanate-phenol-chloroform extraction (Chomocyznski et al., 1987, Anal. Biochem., 162:156.) The isolated RNA is then subjected to coupled reverse transcription and amplification by polymerase chain reaction (RT-PCR), using allele-specific oligonucleotide primers. Conditions for primer annealing are chosen to ensure specific reverse transcription and amplification; thus, the appearance of an amplification product is diagnostic of the presence of the allele specified by the particular primer employed. In another embodiment, RNA encoding FcγRIIA is reverse-transcribed and amplified in an allele-independent manner, after which the amplified FcγR-encoding cDNA is identified by hybridization to allele-specific oligonucleotides or by direct DNA sequencing.

In some embodiments, the present application provides kits for the determination of the sequence at position 131 within the FcγRIIA gene in an individual. The kits comprise reagents useful for determining the sequence at the polymorphic position, and may optionally include data for analysis of polymorphic patterns. The reagents for sequence determination may comprise suitable nucleic acid-based and immunological reagents. Preferably, the kits also comprise suitable buffers, control reagents where appropriate, and directions for determining the sequence at a polymorphic position.

In some embodiments, the present application provides kits which additionally comprise reagents for determining the SAP and CRP concentration levels in a patient. The plasma concentration of SAP can be determined by, for example, performing ELISA assays on sera using commercially available SAP antibodies (e.g., Alpha Diagnostic International Cat #SAP12-S) as described in Pilling, D. J of Immunology, 171: 5537-5546 (2003). The plasma concentration of CRP can be determined using commercially available kits including Human C-Reactive Protein (CRP) ELISA Kits from Alpha Diagnostic International Cat #1000 and Chemicon Cat #CYT298. Additionally, Luminex™ based cytometric bead array assays have been developed for SAP and CRP and are offered by Rules Based Medicine™. The average plasma concentration of SAP in a healthy subject is between 20-40 µg/ml. The average plasma concentration of CRP in a healthy subject is between 0-2 µg/ml. In some embodiments, the SAP and CRP concentrations measured are "free concentration", or rather the concentration of unbound SAP and CRP. Determination of free concentration of SAP and CRP can be performed, e.g., using sandwich ELISA assays. For example, a first antibody that recognizes the FcγR binding site of SAP is used to capture SAP from a biological sample. A second antibody that recognizes the ligand binding site of SAP is then used to detect the free concentration of SAP in the sample. In some embodiments the determining concentrations of SAP and CRP from a biological sample can be used to determine the SAP-to-CRP ratio. A person skilled in the art would be able to use the SAP-to-CRP ratio to more accurately adjust dosage of SAP or other antifibrotic therapy to an appropriate level for the individual patient.

Anti-Fibrotic Therapy

Various treatments for fibrosis related disorders are known to those skilled in the art. Treatments include anti-inflammatory agents, corticosteroids, penicillamine, and colchicine. See e.g., Beers, M H, and Berkow, R, eds. *The Merck Manual*. 7th ed. Merck Research Laboratories, 1999. In some embodiments, anti-fibrotic therapy includes administration of profibrotic factor antagonists and/or anti-fibrotic agents.

Profibrotic Factor Antagonists

Anti-fibrotic therapy encompasses agents that inhibit or antagonize profibrotic factors, such as agents that antagonize one or more growth factors or cytokines involved in the formation and maintenance of fibrotic tissue. In this manner, anti-fibrotic therapy targets fibrocyte, fibrocyte precursor, myofibroblast precursor, and/or hematopoetic monocyte precursor differentiation and fibrotic tissue formation and maintenance.

Profibrotic factors that may be targeted with antagonists as part of the therapies of the present invention include, without limitation, a transforming growth factor type β

(TGF-β, including TGF-β1-5), VEGF, EGF, RANTES, members of the interleukin family (e.g., IL-1, IL-4, IL-5, IL-6, IL-8 and IL-13), tumor necrosis factor type alpha (TNF-α), platelet-derived growth factor (PDGF), basic fibroblast growth factor (bFGF), monocyte chemoattractant protein type 1 (MCP-1), macrophage inflammatory protein (e.g., MIP-1α, MIP-2), connective tissue growth factor (CTGF), endothelin-1, angiotensin-II, rennin, leptin, chemokines (e.g., CCL2, CCL12, CXCL12, CXCR4, CCR3, CCR5, CCR7), SLC/CCL21 and other factors known to promote or be related to the formation, growth, or maintenance of fibrotic tissue. The present invention may include compositions or methods that target one or more of the foregoing factors and cytokines.

In certain embodiments, anti-fibrotic therapy may include antibodies directed to one or more of the profibrotic factors. Such antibodies may be purified, unpurified, or partially purified. The antibodies may be polyclonal or monoclonal antibodies, derived from any suitable animal source, such as mouse, rabbit, rat, human, horse, goat, bovine, and the like. Such antibodies may include antibody fragments, single chain antibodies, polymerized antibodies and/or antibody fragments, and the like.

In certain embodiments, anti-fibrotic therapy may include antagonists of the corresponding receptor of one or more of the profibrotic factors. Such antagonists may include inactive forms of one or more of the profibrotic factors and/or cytokines, such as fragments thereof. Such forms in suitable concentrations may compete with its corresponding profibrotic factors and/or cytokines for binding to its receptor. Similarly, certain antibodies to the receptor may be used to interfere with or prevent binding thereto of the corresponding profibrotic factors and/or cytokines.

In other selected embodiments, anti-fibrotic therapy may include soluble forms of the receptor of one or more of the profibrotic factors and/or cytokines, such that the soluble receptor competes with its corresponding native cellular receptor for the target ligand.

In other selected embodiments, suitable components of the composition may include compounds that compete with or otherwise interfere with binding of one or more of the profibrotic factors and/or cytokines with its receptor. For example, the proteoglycan decorin is known to bind to TGF-β, thereby reducing its availability for binding to its receptor. Mannose-6-phosphate is also known to compete with TGF-β for binding to its corresponding receptor. Other known binding inhibitors of TGF-β include latent transforming growth factor-β binding protein (LTBP) and latency associated peptide (LAP), both of which natively bind to the intracellular precursor of TGF-β.

In certain embodiments, anti-fibrotic therapy may include one or more oligoribonucleotides that contain at least one sequence that is antisense with respect to one or more of the profibrotic factors and/or cytokines. Such components may also include one or more expression plasmids having suitable transcriptional control sequences that yield antisense sequences. In other selected embodiments, anti-fibrotic therapy may include one or more double-stranded oligoribonucleotides, or expression plasmids encoding thereof, that are suitable for degrading transcripts of one or more of the profibrotic factors and/or cytokines via RNA-mediated interference. In other selected embodiments, anti-fibrotic therapy may include one or more single-stranded oligonucleotide aptamers, or expression plasmids encoding thereof, that are suitable for inhibiting or interfering with the binding of profibrotic factors to their cognate receptors.

A suitable profibrotic factor antagonist may include components known to inhibit, attenuate, or interfere with one or more components of the intracellular signaling pathways activated by one or more of the profibrotic factors upon binding to its corresponding receptor.

For example, anti-fibrotic therapy may include components that inhibit or attenuate downstream signal pathway molecules such as SMAD family members and SARA.

A suitable anti-fibrotic therapy may include one or more molecules that are suitable for inhibiting or interfering with the cellular adhesions require for fibrosis. For example, a suitable component may include interfering antibodies to the ICAM-1 and/or CD11, CD49 or CD18 molecules, thereby interfering with the adhesion interaction there between.

In other selected embodiments, a suitable profibrotic factor antagonist may include inhibitors of collagen synthesis, such as proline analogs that interfere with post-translation processing of collagen precursors. Pirfenidone, for example, is an orally active small molecule drug that may inhibit collagen synthesis, downregulate production of multiple cytokines and block fibroblast proliferation.

TGF-β Antagonists

Cytokines of the transforming growth factor (TGF) beta family play a central role in wound healing and in tissue repair, and are found in all tissues. TGF-β is produced by many parenchymal cell types, as well as infiltrating cells such as lymphocytes, monocytes/macrophages, and platelets. Following wounding or inflammation, such cells such are potential sources of TGF-β. In general, TGF-β stimulates the production of various extracellular matrix proteins, inhibits the degradation of these matrix proteins, and promotes tissue fibrosis, all of which contribute to the repair and restoration of the affected tissue. In many diseases, excessive TGF-β contributes to a pathologic excess of tissue fibrosis that can compromise normal organ function.

The term "TGF-β" as used herein includes TGF-β1, TGFβ2, TGF-β3, TGF-β4 and TGF-β5. Also included are other related proteins with similar properties.

As used herein, a "TGF-β antagonist" is any molecule that is able to decrease the amount or activity of TGF-β, either within a cell or within a physiological system. Preferably, the TGF-β antagonist acts to decrease the amount or activity of a TGF-β1, 2, or 3. For example, a TGF-β antagonist may be a molecule that inhibits expression of TGF-β at the level of transcription, translation, processing, or transport; it may affect the stability of TGF-β or conversion of the precursor molecule to the active, mature form; it may affect the ability of TGF-β to bind to one or more cellular receptors (e.g., Type I, II or III); or it may interfere with TGF-β signaling.

A variety of TGF-β antagonists and methods for their production are known in the art and many more are currently under development. The specific TGF-β antagonist employed is not a limiting feature; any effective TGF-β antagonist as defined herein may be useful in the methods and compositions of this invention. Preferably, the TGF-β antagonist is a TGF-β1, TGF-β2, or TGF-β3 antagonist. Most preferably the antagonist is a TGF-β1 antagonist.

Examples of TGF-β antagonists include, but are not limited to: monoclonal and polyclonal antibodies directed against one or more isoforms of TGF-β (Dasch et al., U.S. Pat. No. 5,571,714; see, also, WO 97/13844 and WO 00/66631); TGF-β receptors, soluble forms of such receptors (preferably soluble TGF-β type III receptor), or antibodies directed against TGF-β receptors (Segarini et al., U.S. Pat. No. 5,693,607; Lin et al., U.S. Pat. No. 6,001,969, U.S. Pat. No. 6,010,872, U.S. Pat. No. 6,086,867, U.S. Pat. No. 6,201,108; WO 98/48024; WO 95/10610; WO 93/09228;

WO 92/00330); latency associated peptide (WO 91/08291); large latent TGF-β (WO 94/09812); fetuin (U.S. Pat. No. 5,821,227); decorin and other proteoglycans such as biglycan, fibromodulin, lumican and endoglin (WO 91/10727; Ruoslahti et al., U.S. Pat. No. 5,654,270, U.S. Pat. No. 5,705,609, U.S. Pat. No. 5,726,149; Border, U.S. Pat. No. 5,824,655; WO 91/04748; Letarte et al., U.S. Pat. No. 5,830,847, U.S. Pat. No. 6,015,693; WO 91/10727; WO 93/09800; and WO 94/10187); somatostatin (WO 98/08529); mannose-6-phosphate or mannose-1-phosphate (Ferguson, U.S. Pat. No. 5,520,926); prolactin (WO 97/40848); insulin-like growth factor II (WO 98/17304); IP-10 (WO 97/00691); arg-gly-asp containing peptides (Pfeffer, U.S. Pat. No. 5,958,411; WO 93/10808); extracts of plants, fungi and bacteria (EP-A-813 875; JP 8119984; and Matsunaga et al., U.S. Pat. No. 5,693,610); antisense oligonucleotides (Chung, U.S. Pat. No. 5,683,988; Fakhrai et al., U.S. Pat. No. 5,772,995; Dzau, U.S. Pat. No. 5,821,234, U.S. Pat. No. 5,869,462; and WO 94/25588); proteins involved in TGF-β signaling, including SMADs and MADs (EP-A-874 046; WO 97/31020; WO 97/38729; WO 98/03663; WO 98/07735; WO 98/07849; WO 98/45467; WO 98/53068; WO 98/55512; WO 98/56913; WO 98/53830; WO 99/50296; Falb, U.S. Pat. No. 5,834,248; Falb et al., U.S. Pat. No. 5,807,708; and Gimeno et al., U.S. Pat. No. 5,948,639), Ski and Sno (Vogel, 1999, Science, 286:665; and Stroschein et al., 1999, Science, 286:771-774); one or more single-stranded oligonucleotide aptamers, or expression plasmids encoding thereof, that are suitable for inhibiting or interfering with the binding of TGFβ to its cognate receptors; and any mutants, fragments or derivatives of the above-identified molecules that retain the ability to inhibit the activity of TGF-β.

In certain preferred embodiments, the TGF-β antagonist is a human or humanized monoclonal antibody that blocks TGF-β binding to its receptor (or fragments thereof such as F(ab)$_2$ fragments, Fv fragments, single chain antibodies and other forms or fragments of antibodies that retain the ability to bind to TGF-β. A preferred monoclonal antibody is a human or humanized form of the murine monoclonal antibody obtained from hybridoma 1D11.16 (ATCC Accession No. HB 9849 described in Dasch et al., U.S. Pat. No. 5,783,185).

TGF-β receptors and TGF-β-binding fragments of TGF-β receptors, especially soluble fragments are useful TGF-β antagonists in the methods of the present invention. In certain embodiments, the preferred inhibitor of TGF-β function is a soluble TGF-β receptor, especially TGF-β type II receptor (TGFBIIR) or TGF-β type III receptor (TGFBIIIR, or betaglycan) comprising, e.g., the extracellular domain of TGFBIIR or TGFBIIIR, most preferably a recombinant soluble TGF-β receptor (rsTGFBIIR or rsTGFBIIIR). TGF-β receptors and TGF-β-binding fragments of TGF-β receptors, especially soluble fragments are useful TGF-β antagonists in the methods of the present invention. TGF-β receptors and the nucleic acids encoding them are well known in the art. The nucleic acid sequence encoding TGF-β type 1 receptor is disclosed in GENBank accession number L15436 and in U.S. Pat. No. 5,538,892 of Donahoe et al. The nucleic acid sequence of TGF-β type 2 receptor is publicly available under GENBank accession numbers AW236001; AI35790; AI279872; AI074706; and AA808255. The nucleic acid sequence of TGF-β type 3 receptor is also publicly available under GENBank accession numbers NM 003243; AI887852; AI817295; and AI681599.

Suitable TGF-β antagonists for use in the present invention will also include functional mutants, variants, derivatives and analogues of the aforementioned TGF-β antagonists, so long as their ability to inhibit TGF-β amount or activity is retained. As used herein, "mutants, variants, derivatives and analogues" refer to molecules with similar shape or structure to the parent compound and that retain the ability to act as TGF-β antagonists. For example, any of the TGF-β antagonists disclosed herein may be crystallized, and useful analogues may be rationally designed based on the coordinates responsible for the shape of the active site(s). Alternatively, the skilled artisan may, without undue experimentation, modify the functional groups of a known antagonist and screen such modified molecules for increased activity, half-life, bioavailability or other desirable characteristics. Where the TGF-β antagonist is a polypeptide, fragments and modifications of the polypeptide may be produced to increase the ease of delivery, activity, half-life, etc (for example, humanized antibodies or functional antibody fragments, as discussed above). Given the level of skill in the art of synthetic and recombinant polypeptide production, such modifications may be achieved without undue experimentation. Persons skilled in the art may also design novel inhibitors based on the crystal structure and/or knowledge of the active sites of the TGF-β inhibitors described herein.

Polypeptide inhibitors such as the soluble TGF-β receptors may also be effectively introduced via gene transfer. Accordingly, certain embodiments of the present method involve the use of a vector suitable for expression of a TGF-β receptor or binding partner, preferably a soluble receptor or binding partner. In certain preferred embodiments, administration of a soluble TGF-β antagonist can be effected by gene transfer using a vector comprising cDNA encoding the soluble antagonist, most preferably cDNA encoding the extracellular domain of TGF-β type II (rsTGFBIIR) or type III receptor (rsTGFBIIIR), which vector is administered, preferably topically, to a donor organ to cause in situ expression of the soluble TGF-β antagonist in cells of the organ transfected with the vector. Such in situ expression inhibits the activity of TGF-β and curbs TGF-β-mediated fibrogenesis. Any suitable vector may be used. Preferred vectors include adenovirus, lentivirus, Epstein Barr virus (EBV), adeno-associated virus (AAV), and retroviral vectors that have been developed for the purpose of gene transfer. Other, non-vector methods of gene transfer may also be used, for example, lipid/DNA complexes, protein/DNA conjugates, naked DNA transfer methods, and the like.

Additional suitable TGF-β antagonists developed for delivery via adenoviral gene transfer include, but are not limited to: a chimeric cDNA encoding an extracellular domain of the TGF-β type II Receptor fused to the Ig Fc domain (Isaka et al., 1999, *Kidney Int.*, 55:465-475), adenovirus gene transfer vector of a dominant-negative mutant of TGF-β type II Receptor (Zhao et al, 1998, *Mech. Dev.*, 72:89-100.), and an adenovirus gene transfer vector for decorin, a TGF-β binding proteoglycan (Zhao et al., 1999, *Am. J. Physiol.*, 277:L412-L422). Adenoviral-mediated gene transfer is very high efficiency compared to other gene delivering modalities.

Anti-Fibrotic Agents

In certain embodiments, the profibrotic factor antagonists can be replaced with, or augmented with, a cytokine known to have anti-fibrotic effects, such as IL-12, IL-10, IFN-γ or BMP-7 (OP-1).

The nucleic acid sequences encoding IFN-γ polypeptides may be accessed from public databases, e.g. Genbank, journal publications, etc. While various mammalian IFN-γ polypeptides are of interest, for the treatment of human disease, generally the human protein will be used. Human IFN-γ coding sequence may be found in Genbank, accession numbers P01579 and CAA00375. The corresponding genomic sequence may be found in Genbank, accession numbers J00219; M37265; and V00536. See, for example. Gray et al. (1982) Nature 295:501 (Genbank X13274); and Rinderknecht et al. (1984) J. Biol. Chem. 259:6790.

IFN-γ1b (Actimmune®; human interferon) is a single-chain polypeptide of 140 amino acids. It is made recombinantly in *E. coli* and is unglycosylated. Rinderknecht et al. (1984) J. Biol. Chem. 259:6790-6797.

The IFN-γ to be used in anti-fibrotic therapy may be any of natural IFN-γs, recombinant IFN-γs and the derivatives thereof so far as they have a IFN-γ activity, particularly human IFN-γ activity. Although IFN-γ is based on the sequences as provided above, the production of the protein and proteolytic processing can result in processing variants thereof. The unprocessed sequence provided by Gray et al., supra, consists of 166 amino acids (aa). Although the recombinant IFN-γ produced in *E. coli* was originally believed to be 146 amino acids, (commencing at amino acid 20) it was subsequently found that native human IFN-γ is cleaved after residue 23, to produce a 143 aa protein, or 144 aa if the terminal methionine is present, as required for expression in bacteria During purification, the mature protein can additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG which, in the particular case of *E. coli* expression is not processed away. In other microbial systems or eukaryotic expression systems, methionine may be removed.

For use in the subject methods, any of the native IFN-γ peptides, modifications and variants thereof, or a combination of one or more peptides may be used which may have anti-fibrotic activity. IFN-γ peptides of interest include fragments, and can be variously truncated at the carboxy terminal end relative to the full sequence. Such fragments continue to exhibit the characteristic properties of human gamma interferon, so long as amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925, herein incorporated by reference. Native IFN-γ moieties include molecules variously extending from amino acid residues 24-150; 24-151, 24-152; 24-153, 24-155; and 24-157. Any of these variants, and other variants known in the art and having IFN-γ activity, may be used in the present methods.

The sequence of the IFN-γ polypeptide may be altered in various ways known in the art to generate targeted changes in sequence. A variant polypeptide will usually be substantially similar to the sequences provided herein, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. In certain embodiments, the invention contemplates the use of IFN-γ variants with one or more non-naturally occurring glycosylation and/or pegylation sites that are engineered to provide glycosyl- and/or PEG-derivatized polypeptides with reduced serum clearance, such as the IFN-γ polypeptide variants described in International Patent Publication No. WO 01/36001. Also included are modifications of glycosylation, e.g., those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

In still other embodiments, the antifibrotic agent can be a calcium channel blocker, such as verapamil. Such agents can have an antifibrotic effect due not only to their ability to diminish the synthesis of collagen type I, but also as a consequence to stimulating the degradation of collagen type I fibers. In vitro studies of fibroblasts show that the extracellular transport of collagen depends on the presence of calcium. Verapamil, a calcium-channel blocker, reduces intracellular calcium concentration and increases collagenase activity. It also inhibits the proliferation of fibroblasts.

In some embodiments of the application, the anti-fibrotic therapy comprises one or more SAP agonists, one or more CRP antagonists, or a combination thereof.

SAP Agonists

One aspect of the application provides SAP agonists useful in the treatment of various disorders. SAP agonists encompass all compounds and compositions that increase or otherwise mimic endogenous SAP signaling, including compounds that increase SAP activity.

(i) Human Serum Amyloid P

In certain embodiments, an SAP signaling agonist is an SAP polypeptide or variant thereof. In certain embodiments, an SAP polypeptide is SAP comprising five human SAP protomers (SEQ ID NO: 1). The term "SAP protomer" is intended to refer to a polypeptide that is at least 60%, at least 70%, at least 80%, at least 85%, at least 90%, at least 95%, at least 97%, at least 99% or 100% identical to human SAP protomer, as determined using the FASTDB computer program based on the algorithm of Brutlag et al. (*Comp. App. Biosci.*, 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05. The term "SAP protomer" encompasses functional fragments and fusion proteins comprising any of the preceding. Generally, an SAP protomer will be designed to be soluble in aqueous solutions at biologically relevant temperatures, pH levels and osmolarity. The protomers that non-covalently associate together to form SAP may have identical amino acid sequences and/or post-translational modifications or, alternatively, individual protomers may have different sequences and/or modifications.

Some aspects of the invention provide polypeptides, or provide therapeutic methods for employing those polypeptides, wherein said polypeptides are defined, at least in part, to a reference sequence. Accordingly, such polypeptides may have a certain percentage of amino acid residues which are not identical to a reference sequence. In some embodiments, the non-identical residues have similar chemical properties to the residues to which they are not identical. Groups that have similar properties include the following amino acids: E, D, N, Q; H, K, R; Y, F and W; I, L, V, M, C, A; and S, T, C, P, A.

In some embodiments, the residues that are not identical are those which are not evolutionarily conserved between the reference sequence and an orthologous sequence in at least one evolutionarily related species, such as in species within the same order. In the case of a vertebrate reference sequence, the amino acids that may be mutated in a preferred embodiment are those that are not conserved between the reference sequence and the orthologous sequence in another vertebrate species. For example, if a polypeptide used in a method of the present invention is said to comprise an amino acid sequence that is at least 95% identical to human SAP (SEQ ID NO:1), then said polypeptide may have non-identical residues to those positions in which the human SAP and that of another vertebrate differ. FIG. 1 depicts human SAP aligned against two mammalian and one avian SAP sequence. Unshaded residues indicate residues that differ from the human SAP sequence.

Polypeptides sharing at least 95% identity with SEQ ID NO:1 include polypeptides having conservative substitutions in these areas of divergence. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent can be found in Bowie et al., Science 247:1306-1310 (1990).

SAP polypeptides comprising polymers that are at least 60%, at least 70%, at least 80%, at least 85%, at least 90%, at least 95%, at least 97%, or at least 99% identical to SEQ ID NO. 1 preferably inhibit fibrosis.

In certain embodiments, an SAP signaling agonist is an SAP variant. The term "SAP variant" is intended to refer to a protein comprising from two to five SAP protomers that demonstrates one or more of the following features as compared to the human SAP pentamer: increased plasma half-life, increased in vitro stability, or increased in vivo stability relative to human SAP.

In specific embodiments of the present invention, compositions containing SAP, SAP variants, or SAP functional fragments may be operable to raise SAP concentration in target locations to approximately at least 0.5 µg/ml. In humans, 1125 radiolabelled SAP has been previously administered to study patients with amyloidosis. In the treatments, approximately 600 µg of SAP was administered to an adult human. Accordingly, administration of approximately 600 µg of SAP systemically to an adult human is safe. Higher dosages may also be safe under appropriate conditions.

(ii) Anti-FcγR Antibodies as SAP Agonists

In one aspect of the invention, one or more compounds are provided that mimic SAP signaling. In some embodiments, the SAP signaling agonist are anti-FcγR antibodies, wherein the antibodies are selected from a class of anti-FcγRI, anti-FcγRIIA, and anti-FcγRIII antibodies that are able to bind to either FcγRI, FcγRIIA, or FcγRIII, respectively. Anti-FcγR antibodies are IgG antibodies that bind to receptors for the Fc portion of IgG antibodies (FcγR). The anti-FcγR antibodies bind through their variable region, and not through their constant (Fc) region. Anti-FcγR antibodies may include any isotype of antibody. The anti-FcγR antibodies may be further cross-linked or aggregated with or without additional antibodies or other means. This process initiates intracellular signaling events consistent with FcγR activation.

Compositions containing anti-FcγRI antibodies, anti-FcγRII antibodies, and/or anti-FcγRIII antibodies may be used to suppress the differentiation of fibrocytes in inappropriate locations, in fibrosing disorders, and chronic inflammatory conditions.

In specific embodiments, compositions containing approximately 1.0 µg/mL anti-FcγR antibodies may be effective to inhibit fibrocyte differentiation by approximately 50%. In other embodiments, compositions may contain an amount sufficient to deliver 1.0 µg/mL anti-FcγR antibodies to the target tissue.

Anti-FcγR antibodies may be administered in a dose of approximately 1.0 µg/mL, in an amount sufficient to deliver 1.0 µg/mL anti-FcγR antibodies to the target tissue, or in another dose sufficient to inhibit fibrocyte differentiation without causing an undesirable amount of cell death in the patient.

(iii) Aggregated Fc Domains and Fc-Containing Antibodies

In some embodiments, the SAP signaling agonists are cross-linked or aggregated IgG. IgG from the appropriate source (e.g. human IgG for human receptors) may normally bind to FcγR through its Fc region. Cross-linked or aggregated IgG may include any IgG able to bind the target FcγR through its Fc region, provided that at least two such IgG antibodies are physically connected to one another.

Antibodies of both types may include whole antibodies or a portion thereof, preferably the portion functional in suppression of fibrocyte differentiation. For example, they may include any antibody portion able to cross-link FcγR. This may include aggregated or cross-linked antibodies or fragments thereof, such as aggregated or cross-linked whole antibodies, F(ab')$_2$ fragments, and possible even Fc fragments.

Aggregation or cross-linking of antibodies may be accomplished by any known method, such as heat or chemical aggregation. Any level of aggregation or cross-linking may be sufficient, although increased aggregation may result in increased fibrocyte suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

Compositions containing cross-linked or aggregated IgG may be used to suppress the differentiation of fibrocytes in inappropriate locations and in fibrosing disorders and chronic inflammatory conditions, inter alia.

In other specific embodiments, compositions may contain as little as 0.1 µg ml cross-linked or aggregated IgG. Aggregated or cross-linked IgG may be administered in an amount sufficient to deliver at least 0.1 µg/ml IgG to the target tissue, or in another dose sufficient to inhibit fibrocyte differentiation without causing an undesirable amount of cell death in the patient.

(iv) SAP Peptidomimetic

In certain embodiments, the SAP agonists include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of SAP polypeptides.

(v) Increase SAP Activity

In some embodiments, an SAP agonist increases SAP activity. SAP activity can be increased by increasing the concentration of SAP by, for example, increasing SAP transcription, increasing translation, increasing SAP secretion, increasing SAP RNA stability, increasing SAP protein stability, or decreasing SAP protein degradation. SAP activity can also be increased by increasing specifically the "free concentration" of SAP or rather the unbound form by, for example, decreasing SAP endogenous binding partners.

(iv) FcγR Crosslinkers

In some embodiments, fibronectin based scaffold domain proteins may be used as SAP agonists to crosslink FcγRs. Fibronectin based scaffold domain proteins may comprise a fibronectin type III domain (Fn3), in particular a fibronectin type III tenth domain ($^{10}$Fn3).

In order to crosslink FcγRs, multimers of FcγR binding Fn3 domains may be generated as described in U.S. Pat. No. 7,115,396.

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. The BC, DE, and FG loops are both structurally and functionally analogous to the complementarity determining regions (CDRs) from immunoglobulins. Fn3 domains can be designed to bind almost any compound by altering the sequence of one or more of the BC, DE, and FG loops. Methods for generating specific binders have been described in U.S. Pat. No. 7,115,396, disclosing high affinity TNFα binders, and U.S. Publication No. 2007/0148126, disclosing high affinity VEGFR2 binders. An example of fibronectin-based scaffold proteins are Adnectins™ (Adnexus, a Bristol-Myers Squibb R&D Company).

In some embodiments, the SAP agonist is an aptamer. In order to crosslink FcγRs, multimers of FcγR binding aptamers may be generated.

Aptamers, are oligonucleotides, which can be synthetic or natural, that bind to a particular target molecule, such as a protein or metabolite. Typically, the binding is through interactions other than classic Watson-Crick base pairing. Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In Vitro Cell. Dev. Biol. Anim. 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. Systematic Evolution of Ligands by Exponential Enrichment, "SELEX™," is a method for making a nucleic acid ligand for any desired target, as described, e.g., in U.S. Pat. Nos. 5,475,096 and 5,270,163, and PCT/US91/04078, each of which is specifically incorporated herein by reference.

CRP Antagonists

One aspect of the application provides CRP antagonists useful in the treatment of various disorders. CRP antagonists encompass all compounds and compositions that decrease, block, or inhibit CRP signaling. In some embodiments, CRP signaling antagonists useful for the methods include small molecules, polypeptides (including antibodies), or nucleic acids (including antisense nucleic acids, aptamers, ribozymes, and small interfering RNAs or siRNAs). CRP signaling antagonists encompasses any composition that modulates, affects, alters, inhibits or reduces the activity of CRP by at least 5, 10, 20, 30, 40, 50, 60, 70, 80, 90, 95, 97, 98, 99 or 100%.

(i) Decrease CRP Expression Level

In some embodiments, a CRP signaling antagonist inhibits CRP expression levels. CRP expression level may be decreased at the level of RNA or protein.

In certain embodiments, one or more of the CRP signaling antagonists is an antisense nucleic acid that targets the expression of CRP. By "antisense nucleic acid," it is meant a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In other embodiments, the CRP signaling antagonist may be an siRNA. The term "short interfering RNA," "siRNA," or "short interfering nucleic acid," refers to any nucleic acid compound capable of mediating RNAi or gene silencing when processed appropriately by a cell. For example, the siRNA can be a double-stranded polynucleotide molecule comprising self-complementary sense and antisense regions, wherein the antisense region comprises complementarity to a target nucleic acid compound (e.g., CRP). The siRNA can be a single-stranded hairpin polynucleotide having self-complementary sense and antisense regions, wherein the antisense region comprises complementarity to a target nucleic acid compound. The siRNA can be a circular single-stranded polynucleotide having two or more loop structures and a stem comprising self-complementary sense and antisense regions, wherein the antisense region comprises complementarity to a target nucleic acid compound, and wherein the circular polynucleotide can be processed either in vivo or in vitro to generate an active siRNA capable of mediating RNAi. The siRNA can also comprise a single stranded polynucleotide having complementarity to a target nucleic acid compound, wherein the single stranded polynucleotide can further comprise a terminal phosphate group, such as a 5'-phosphate (see for example Martinez et al., 2002, Cell., 110, 563-574), or 5',3'-diphosphate.

As described herein, the subject siRNAs are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In certain embodiments, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject siRNAs can be carried out by chemical synthetic methods or by recombinant nucleic acid techniques. Endogenous RNA polymerase of the treated cell may mediate transcription in vivo, or cloned RNA polymerase can be used for transcription in vitro. As used herein, siRNA molecules of the disclosure need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an dsRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the disclosure lack 2'-hydroxy(2'-OH) containing nucleotides.

In a specific embodiment, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In certain embodiments, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA is in the form of a hairpin structure (named as hairpin RNA or short hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In certain embodiments, antisense oligonucleotides comprise modification with Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638.)

The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

In certain embodiments, an siRNA molecule of the invention comprises one or more (e.g., about 1, 2, 3, 4, 5, 6, 7, 8, 9, 10, or more) locked nucleic acid (LNA) nucleotides, for example, at the 5'-end, the 3'-end, both of the 5' and 3'-ends, or any combination thereof, of the siRNA molecule PCT application WO 01/77350 describes an exemplary vector for bi-directional transcription of a transgene to yield both sense and antisense RNA transcripts of the same transgene in a eukaryotic cell. Accordingly, in certain embodiments, the present disclosure provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

In another embodiment, one or more CRP signaling antagonists may be an enzymatic nucleic acid. By "enzymatic nucleic acid," it is meant a nucleic acid which has complementarity in a substrate binding region to a specified target gene, and also has an enzymatic activity which is active to specifically cleave a target nucleic acid. It is understood that the enzymatic nucleic acid is able to intermolecularly cleave a nucleic acid and thereby inactivate a target nucleic acid. These complementary regions allow sufficient hybridization of the enzymatic nucleic acid to the target nucleic acid and thus permit cleavage. One hundred percent complementarity (identity) is preferred, but complementarity as low as 50-75% can also be useful (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acids with enzymatic activity. The specific enzymatic nucleic acids described herein are not meant to be limiting and those skilled in the art will recognize that all that is important in an enzymatic nucleic acid is that it has a specific substrate binding site which is complementary to one or more of the target nucleic acid regions, and that it have nucleotide sequences within or surrounding that substrate binding site which imparts a nucleic acid cleaving and/or ligation activity to the molecule (Cech et al., U.S. Pat. No. 4,987,071; Cech et al., 1988, 260 JAMA 3030). In certain embodiments, an enzymatic nucleic acid is a ribozyme designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). In another embodiment, an enzymatic nucleic acid is a DNA enzyme. Methods of making and administering DNA enzymes can be found, for example, in U.S. Pat. No. 6,110,462.

In some embodiments, the CRP antagonist is an antisense compound as described in U.S. Pat. No. 6,964,950.

(ii) Decrease CRP Plasma Levels

In some embodiments, one or more CRP signaling antagonists decreases serum levels of CRP (Prasad, K. Cardiovascular Drug Review 21:33-50 (2006)). CRP lowering agents include anti-inflammatory drugs such as aspirin and cyclooxygenase-2 inhibitors such as rofecoxib and celecoxib; antiplatelet agents such as clopidogrel; lipid lower agents such as statins, including atorvastatin, pravastatin, simvastatin and cerivastatin, ezetimibe, fenofibrate, and niacin (vitamin $B_3$); anti-diabetic agents such as thiazolidinedione and rosiglitazone; 11-beta hydroxylase inhibitors such as DIO-902 (DiObex); β-adrenoreceptor antagonists such as carvedilol; anti-oxidants such as α-tocopherol, vitamin E and vitamin C; angiotensin converting enzyme (ACE) inhibitors such as ramipril, fosinopril, and captopril; angiotensin receptor blockers such as valsartan, losartan, telmisartan, irbesartan and olmesartan.

(iii) Decrease CRP Signaling

In certain embodiments, one or more of the CRP signaling antagonists are scaffold-based binding proteins such as Nanobody, Evibody, Ankyrin repeat protein, Trans-body, Anticalin, Microbody, AdNectin, Domain antibody, Affibody, Maxibody, Tetranectin, Affilin molecule, iMabs, and Monobody (Hey et al., Trends Biotechnol, 2005, 23: 514-522; Binz et al., Nat Biotechnol, 2005, 23: 1257-1268; Hosse, R. J., et al., Protein Science, 15:14-27 (2006)). In certain embodiments, the protein display scaffold is a fibronectin based "addressable" therapeutic binding molecule. The fibronectin domain III (FnIII) loops comprise regions that may be subjected to random mutation and directed evolutionary schemes of iterative rounds of target binding, selection, and further mutation in order to develop useful therapeutic tools. An exemplary embodiment of fibronectin based protein therapeutics are Adnectins™ as described in PCT publications WO00/34784, WO01/64942, and WO02/032925.

In some embodiments, one or more of the CRP signaling antagonists comprises an antibody or antigen binding fragment that binds to CRP or to CRP ligand protein. It is understood that antibodies may be Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques.

In some embodiments of the application, the antibody fragments provided are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments This application also provides fragments of anti-CRP antibodies, which may comprise a portion of an intact antibody, such as for example, the antigen-binding or variable region of the intact antibody. Examples of antibody fragments include Fab, Fab', F(ab')$_2$, and Fv fragments; diabodies; linear antibodies (Zapata et al., Protein Eng. 1995; 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen. "Fv" usually refers to the minimum antibody fragment that contains a complete antigen-recognition and -binding site. This region consists of a dimer of one heavy- and one light-chain variable region in tight, non-covalent association. It is in this configuration that the three CDRs of each variable region interact to define an antigen-binding site on the surface of the $V_H$-$V_L$ dimer. Collectively, the CDRs confer antigen-binding specificity to the antibody. However, even a single variable region (or half of an Fv comprising three CDRs specific for an antigen) has the ability to recognize and bind antigen, although likely at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., an anti-EphB4 antibody of the application. Alternatively, the target binding region is derived from a protein that binds EphB4.

The term "diabodies" refers to small antibody fragments with two antigen-binding sites, which fragments comprise a heavy-chain variable region ($V_H$) connected to a light-chain variable region ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (Janeway et al., *Immunobiology* 5th edition, page 147, Garland Publishing (New York, 2001)).

The anti-CRP antibodies of the present application include antibodies having all types of constant regions, including IgM, IgG, IgD, IgA and IgE, and any isotype, including IgG1, IgG2a, IgG2b, IgG3 and IgG4. The light chains of the antibodies can either be kappa light chains or lambda light chains.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In some embodiments, the CRP signaling antagonist is an aptamer. The aptamer may be suitable for inhibiting or interfering with the binding of profibrotic factors to their cognate receptors. In some embodiments the aptamer may inhibit binding of TGFβ to its cognate receptors.

In some embodiments, the CRP signaling antagonist is a small molecule. In some embodiments the small molecule is a bis(phosphocholine) hexane compound as described in Pepys, M B., Nature, 440:1217-1221 (2006). In certain embodiments, the small molecule is selected from 1,4-bis(phosphocholine)-hexane, 1,5-bis(phosphocholine)-hexane, 1,6-bis(phosphocholine)-hexane, or 1,7-bis(phosphocholine)-hexane. In some embodiments, the small molecule is a CRP inhibitor disclosed in U.S. Patent Application 2006/0019930. In some embodiments, the small molecule is phosphocholine-hexane-phosphocholine (PCHPC) or a derivative thereof.

In one aspect of the invention, one or more compounds are provided that antagonize CRP signaling. In some embodiments, the CRP signaling antagonist are anti-FcγR antibodies, wherein the antibodies are selected from a class of anti-FcγRI, anti-FcγRIIA, and anti-FcγRIII antibodies that are able to bind to either FcγRI, FcγRIIA, or FcγRIII, respectively. Anti-FcγR antibodies are IgG antibodies that bind to receptors for the Fc portion of IgG antibodies (FcγR). The anti-FcγR antibodies bind through their variable region, and not through their constant (Fc) region. Anti-FcγR antibodies may include any isotype of antibody. The anti-FcγR antibodies may be further cross-linked or aggregated with or without additional antibodies or other means. This process initiates intracellular signaling events consistent with FcγR activation.

Compositions containing anti-FcγRI antibodies, anti-FcγRII antibodies, and/or anti-FcγRIII antibodies may be used to suppress the differentiation of fibrocytes in inappropriate locations, in fibrosing disorders, and chronic inflammatory conditions.

In specific embodiments, compositions containing approximately 1.0 μg/mL anti-FcγR antibodies may be effective to inhibit fibrocyte differentiation by approximately 50%. In other embodiments, compositions may contain an amount sufficient to deliver 1.0 μg/mL anti-FcγR antibodies to the target tissue.

Anti-FcγR antibodies may be administered in a dose of approximately 1.0 μg/mL, in an amount sufficient to deliver 1.0 μg/mL anti-FcγR antibodies to the target tissue, or in another dose sufficient to inhibit fibrocyte differentiation without causing an undesirable amount of cell death in the patient.

Fibrosis Related Disorders

Fibrosis is generally characterized by the pathologic or excessive accumulation of collagenous connective tissue. Fibrosis related disorders that may be amenable to treatment with the subject method include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, moderate to severe asthma and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport syndrome, HIV-associated nephropathy, polycystic kidney disease, Fabry's disease, diabetic nephropathy, chronic glomerulonephritis, nephritis associated with systemic lupus, and the like), progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's ophthalmopathy, diabetic retinopathy, glaucoma, Peyronie's disease, penis fibrosis, urethrostenosis after cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), stromal cell tumors, mucositis, fibrosis induced by chemical or environmental insult (e.g., cancer chemotherapy, pesticides, radiation (e.g., cancer radiotherapy), and the like), and the like.

In some embodiments, the fibrosis related disorder is selected from systemic or local scleroderma, keloids, hypertrophic scars, atherosclerosis, restenosis, pulmonary inflammation and fibrosis, idiopathic pulmonary fibrosis, liver cirrhosis, fibrosis as a result of chronic hepatitis B or C infection, kidney disease, heart disease resulting from scar tissue, macular degeneration, and retinal and vitreal retinopathy. In some embodiments, the fibrosis related disorder results from chemotherapeutic drugs, radiation-induced fibrosis, and injuries and burns.

Anti-fibrotic therapy compositions may be applied locally or systemically. The compositions may also be supplied in combinations or with cofactors. Compositions may be administered in an amount sufficient to restore normal levels, if the composition is normally present in the target location, or they may be administered in an amount to raise levels above normal levels in the target location.

Anti-fibrotic therapy compositions may be supplied to a target location from an exogenous source, or they may be made in vivo by cells in the target location or cells in the same organism as the target location.

Anti-fibrotic therapy compositions may be in any physiologically appropriate formulation. They may be administered to an organism by injection, topically, by inhalation, orally or by any other effective means.

The same compositions and methodologies described above to suppress or inhibit excessive fibrosis formation and maintenance may also be used to suppress or inhibit inappropriate fibrosis formation. For example, they may treat or prevent a condition occurring in the liver, kidney, lung, heart and pericardium, eye, skin, mouth, pancreas, gastrointestinal tract, brain, breast, bone marrow, bone, genitourinary, a tumor, or a wound.

Generally, they may treat or prevent fibrosis related disorders resulting from conditions including but not limited to rheumatoid arthritis, lupus, pathogenic fibrosis, fibrosing disease, fibrotic lesions such as those formed after *Schistosoma japonicum* infection, radiation damage, autoimmune diseases, Lyme disease, chemotherapy-induced fibrosis, HIV- or infection-induced focal sclerosis, failed back syndrome due to spinal surgery scarring, abdominal adhesion post surgery scarring, and fibrocystic formations.

Specifically, in the liver, they may treat or prevent fibrosis resulting from conditions including but not limited to alcohol, drug, and/or chemically induced cirrhosis, ischemia-reperfusion, injury after hepatic transplant, necrotizing hepatitis, hepatitis B, hepatitis C, primary biliary cirrhosis, and primary sclerosing cholangitis.

Relating to the kidney, they may treat or prevent fibrosis resulting from conditions including but not limited to proliferative and sclerosing glomerulonephritis, nephrogenic fibrosing dermopathy, diabetic nephropathy, renal tubulointerstitial fibrosis, and focal segmental glomerulosclerosis.

Relating to the lung, they may treat or prevent fibrosis resulting from conditions including but not limited to pulmonary interstitial fibrosis, drug-induced sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, and emphysema.

Relating to the heart and/or pericardium, they may treat or prevent fibrosis resulting from conditions including but not limited to myocardial fibrosis, atherosclerosis, coronary artery restenosis, congestive cardiomyopathy, heart failure, and other post-ischemic conditions.

Relating to the eye, they may treat or prevent fibrosis resulting from conditions including but not limited to exopthalmos of Grave's disease, proliferative vitreoretinopathy, anterior capsule cataract, corneal fibrosis, corneal scarring due to surgery, trabeculectomy-induced fibrosis, and other eye fibrosis.

Relating to the skin, they may treat or prevent fibrosis resulting from conditions including but not limited to Depuytren's contracture, scleroderma, keloid scarring, psoriasis, hypertrophic scarring due to burns, and psuedoscleroderma caused by spinal cord injury.

Relating to the mouth, they may treat or prevent fibrosis resulting from conditions including but not limited to periodontal disease scarring and gingival hypertrophy secondary to drugs.

Relating to the pancreas, they may treat or prevent fibrosis resulting from conditions including but not limited to pancreatic fibrosis, stromal remodeling pancreatitis, and stromal fibrosis.

Relating to the gastrointestinal tract, they may treat or prevent fibrosis resulting from conditions including but not limited to collagenous colitis, villous atrophy, cryp hyperplasia, polyp formation, fibrosis of Crohn's disease, and healing gastric ulcer.

Relating to the brain, they may treat or prevent fibrosis resulting from conditions including but not limited to glial scar tissue.

Relating to the breast, they may treat or prevent fibrosis resulting from conditions including but not limited to fibrocystic disease and desmoplastic reaction to breast cancer.

Relating to the bone marrow, they may treat or prevent fibrosis resulting from conditions including but not limited to fibrosis in myelodysplasia and neoplastic diseases.

Relating to the bone, they may treat or prevent fibrosis resulting from conditions including but not limited to rheumatoid pannus formation.

Relating to the genitourinary system, they may treat or prevent fibrosis resulting from conditions including but not limited to endometriosis, uterine fibroids, and ovarian fibroids.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Pharmaceutical Preparations and Formulations

In certain embodiments, the methods described herein involve administration of an anti-fibrotic therapy to a subject. The therapeutic agents may be formulated in a conventional manner using one or more physiologically acceptable carriers or excipients. For example, therapeutic agents and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), Therapeutic agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

Therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, therapeutic agents may also be formulated as a depot preparation. Such long acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, therapeutic agents are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more Therapeutic agents described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. Therapeutic agents may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen free environment according to methods in the art.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

Antisense nucleotides, such as siRNA, may be delivered to cancer cells using a variety of methods. Cell-penetrating peptides (CPPs) having the ability to convey linked "cargo" molecules into the cytosol may be used (see Juliano, Ann N Y Acad Sci. 2006 October; 1082:18-26). In certain embodiments, an atelocollagen-mediated oligonucleotide delivery system is used (Hanai et al. Ann N Y Acad Sci. 2006 October; 1082:9-17). An LPD formulation (liposome-polycation-DNA complex) may be used to deliver siRNA to tumor cells. (Li et al. Ann N Y Acad Sci. 2006 October; 1082:1-8). Complexation of siRNAs with the polyethylenimine (PEI) may also be sued to deliver siRNA into cells (Aigner, J Biomed Biotechnol. 2006; 2006(4):71659). siRNA may also be complexed with chitosan-coated polyisohexylcyanoacrylate (PIHCA) nanoparticles for in vivo delivery. (Pille et al., Hum Gene Ther. 2006 October; 17(10):1019-26)

EXEMPLIFICATION

Example 1. In Vitro Models to Determine Target SAP-to-CRP Ratio for Inhibiting Monocyte Differentiation Fibrocyte Differentiation Assay Monocytes were purified from whole blood-derived PBMC using negative magnetic bead selection standard in the art (e.g. CAT#113-41D, Invitrogen, Carlsbad, Calif.) and cultured in a 96-Well tissue culture plate containing FibroLife Media supplemented with 25 or 50 ng/ml of M-CSF in triplicate. The plate was incubated for 96 hours at 37° C. in a 5% CO2 incubator. The cells were then fixed with paraformaldehyde and stained with Hema 3 stain (Cat #122-911, Hema 3 Stain, Fisher Scientific, Hampton, N.H.). The number of fibrocytes per well were determined by summing the count of five different fields per well using an inverted microscope. Fibrocytes were defined morphologically as adherent cells with an elongated spindle-shape and the presence of an oval nucleus. The data indicated that either 25 or 50 ng/ml of M-CSF was sufficient to increase the number of fibrocytes differentiating from monocytes by ~50% in this donor (FIG. 2). Subsequent experiments used FibroLife Media supplemented with 25 ng/ml of M-CSF as needed and defined below.

Fibrolife Media: (Cat #LM-0001, Lifeline Cell Technology, Walkersville, Md.) supplemented with 10 mM HEPES (Cat #H0887, Sigma-Aldrich), 1× non-essential amino acids (Cat #M7145, Sigma-Aldrich,), 1 mM sodium pyruvate (Cat #S8636, Sigma-Aldrich), 2 mM glutamine (Cat #25030-149, Invitrogen), 100 U/ml penicillin and 100 ug/ml streptomycin (Cat #P0781, Sigma-Aldrich), and ITS-3 (Cat #12771, 500 ug/ml bovine serum albumin, 10 ug/ml insulin, 5 ug/ml transferrin, 5 ng/ml sodium selenite, 5 ug/ml linoleic acid, and 5 ug/ml oleic acid; Sigma-Aldrich).

In an alternative version of this assay, PBMC or monocytes are purified from whole blood and cultured in FibroLife Media supplemented with various amounts of SAP and CRP in triplicate. The number of fibrocytes increases with increasing CRP concentration in certain donors and decrease with increasing SAP concentration in all donors.

Calculating the Minimum SAP/CRP Ratio In Vitro

Method 1: Monocytes were purified from whole blood-derived PBMC using negative magnetic bead selection standard in the art (e.g. CAT#113-41D, Invitrogen, Carlsbad, Calif.) and cultured in a 96-Well tissue culture plate containing FibroLife Media and various concentrations of SAP in triplicate. The plate was incubated for 96 hours at 37° C. in a 5% $CO_2$ incubator. The cells were then fixed with paraformaldehyde and stained with Hema 3 stain (Cat #122-911, Hema 3 Stain, Fisher Scientific, Hampton, N.H.). The number of fibrocytes per well were determined by summing the count of five different fields per well using an inverted microscope. Fibrocytes were defined morphologically as adherent cells with an elongated spindle-shape and the presence of an oval nucleus. The minimum concentration of SAP necessary to provide maximum inhibition of fibrocyte differentiation in this system was determined to be 2 ug/ml (FIG. 3A).

Monocytes were purified from whole blood-derived PBMC using negative magnetic bead selection standard in the art (e.g. CAT#113-41D, Invitrogen, Carlsbad, Calif.) and cultured in a 96-Well tissue culture plate containing FibroLife Media supplemented with a range of hCRP, 2 ug/ml hSAP, and 25 ng/ml hMCSF in triplicate. The plate was incubated for 96 hours at 37° C. in a 5% CO2 incubator. The cells were then fixed with paraformaldehyde and stained with Hema 3 stain (Cat #122-911, Hema 3 Stain, Fisher Scientific, Hampton, N.H.). The number of fibrocytes per well was determined by summing the count of five different fields per well using an inverted microscope. Fibrocytes were defined morphologically as adherent cells with an elongated spindle-shape and the presence of an oval nucleus. CRP concentrations ≥40 ug/ml were sufficient to block the effects of 2 ug/ml of hSAP (FIG. 3B). The indicated SAP concentration was divided by the indicated CRP concentration to determine the minimum SAP/CRP ratio which should prevent fibrocyte differentiation in vivo. These data indicate that a SAP/CRP ratio ≥0.05 would be sufficient under serum free conditions, as may occur in a local tissue site.

Method 2. In an alternative version of this assay, the effective SAP/CRP ratio can be calculated, from donors responsive to CRP stimulation of fibrocyte differentiation, by determining the minimum concentration of CRP necessary to provide maximum stimulation of fibrocyte differentiation, then determining the concentration of SAP necessary at that concentration of CRP to reduce the amount of fibrocyte differentiation by >90%. The indicated SAP concentration is then divided by the indicated CRP concentration to determine the minimum SAP/CRP ratio which should prevent fibrocyte differentiation in vivo. The target SAP-to-CRP ratio is tested in various in vivo fibrosis models to confirm in vivo target ratio.

Transwell Migration Assay

In an alternative assay, a porous membrane is coated with collagen IV on one side and HUVEC cells are cultured in a monolayer on the same side. The transwell is then suspended in media in a welled plate and PBMC are added to the top of the transwell. The PBMC are induced to migrate across the HUVEC layer by adding chemokines such as MCP-1 to the bottom of the well. As the cells transmigrate, they differentiate into fibrocytes.

Various amounts of SAP and CRP are added to the top of the transwell to determine the SAP-to-CRP ratio that inhibits differentiation into fibrocytes. The following final concentrations are tested. The target SAP-to CRP ratio is tested in various in vivo fibrosis models to confirm in vivo target ratio (Table 1).

TABLE 1

| SAP μg/ml | CRP μg/ml | SAP-to-CRP ratio |
|---|---|---|
| 10 | 10 | 1 |
| 5 | 10 | 0.5 |
| 2 | 10 | 0.2 |
| 1 | 10 | 0.1 |
| 0.5 | 10 | 0.05 |
| 0.25 | 10 | 0.025 |
| 0.1 | 10 | 0.01 |
| 10 | 2.5 | 5 |
| 10 | 1 | 10 |
| 10 | 0.5 | 20 |
| 10 | 0.1 | 100 |
| 10 | 0.01 | 1000 |
| 10 | 0.001 | 10,000 |

Example 2. Exemplary In Vivo Model Systems (i) Bleomycin-Induced Lung Fibrosis

Pulmonary fibrosis is produced in male Sprague-Dawley rats weighing 200-250 grams. An endotracheal dose (via transoral route) of 2.5-6.67 U/kg of bleomycin dissolved in 0.9% sodium chloride at a volume of 0.67 mL/kg is administered on Day 0.

Study Group 1

On study Day 1 serum concentration for both SAP and CRP are determined. The ratio determined on Day 1 is used to calculate the dose of SAP needed to reach the target ratio defined in example 1. The calculated dose is administered on Days 2, 4, 6, 8, and 10. Rats in the treated group are dosed intravenously via tail vein with SAP at a dose volume of 2-10 mL/kg. Untreated rats are dosed with 2-10 mL/kg of saline.

On Day 14 lung function is assessed by measuring blood oxygen saturation (pulse oximetry) and/or $PO_2$ (blood gas analyzer); breath rate and heart rate are also measured. The animals are then sacrificed, and the left lung is processed for total collagen content (Sircol assay) and the right lung is fixed in 10% formalin, sectioned and stained with Sirius Red and hematoxylin and eosin to assess collagen deposition.

Study Group 2: Adjustment of Dosage

On study Day 1 serum concentration for both SAP and CRP are determined. The ratio determined on Day 1 is used to calculate the dose of SAP needed to reach the target ratio defined in example 1. The calculated dose is administered on Day 2. On Day 3, serum concentration for both SAP and CRP are determined. The dosage is adjusted based on the concentrations determined on Day 2. On Day 4, the adjusted dosage is administered. These steps are repeated (measuring serum concentration on Days 5, 7, and 9; administering adjusted dosage on Days 6, 8, and 10). Rats in the treated group are dosed intravenously via tail vein with SAP at a dose volume of 1.3 mL/kg. Untreated rats are dosed with 1.3 mL/kg of saline. On Day 14 lung function is assessed by measuring blood oxygen saturation (pulse oximetry) and/or $PO_2$ (blood gas analyzer); breath rate and heart rate are also measured. The animals are then sacrificed, and the left lung is processed for total collagen content (Sircol assay) and the right lung is fixed in 10% formalin, sectioned and stained with Sirius Red and hematoxylin and eosin to assess collagen deposition.

Reference:

Cortijo, et al. Attenuation by oral N-acetylcysteine of bleomycin-induced lung injury in rats. *Eur Respir J* 17:1228-1235, 2001.

(ii) Liver Fibrosis, Carbon Tetrachloride Administration

Hepatic fibrosis is produced in male Wistar rats weighing 200-225 grams. On Day 0, rats receive an intragastric dose of $CCl_4$ in olive oil (0.08 mL $CCl_4$/mL of olive oil; initial dose of 412 mg $CCl_4$/kg) or olive oil alone (controls). Rats are dosed with $CCl_4$ twice a week for the duration of the study, with weekly doses adjusted based on body weight changes to reduce mortality.

Study Group 1

On study Day 1 serum concentrations for both SAP and CRP are determined. The ratio determined on Day 1 is used to calculate the dose of SAP needed to reach the target ratio defined in example 1. The calculated dose is administered every other day beginning on Day 2. Rats in the treated group are dosed intravenously via tail vein with SAP at a dose volume of 2-10 mL/kg. Untreated rats are dosed with 2-10 mL/kg of saline.

On Day 24, rats are sacrificed, body and liver weights are assessed, and liver tissue is harvested for analysis. Total collagen content is measured with the Sircol assay, and collagen deposition is measured with Masson trichrome, hematoxylin and eosin and Sirius red staining. Myofibroblast activation is determined by immunostaining for α-SMA.

Study Group 2: Adjustment of Dosage

On study Day 1 serum concentration for both SAP and CRP are determined. The ratio determined on Day 1 is used to calculate the dose of SAP needed to reach the target ratio defined in example 1. The calculated dose is administered on Day 2. On Day 3, serum concentration for both SAP and CRP are determined. The dosage is adjusted based on the concentrations determined on Day 2. On Day 4, the adjusted dosage is administered. These steps are repeated (measuring serum concentration on odd numbered days; administering adjusted dosage on even-numbered days). Rats in the treated group are dosed intravenously via tail vein with SAP at a dose volume of 2-10 mL/kg. Untreated rats are dosed with 2-10 mL/kg of saline.

On Day 24, rats are sacrificed, body and liver weights are assessed, and liver tissue is harvested for analysis. Total collagen content is measured with the Sircol assay, and collagen deposition is measured with Masson trichrome, hematoxylin and eosin and Sirius red staining. Myofibroblast activation is determined by immunostaining for α-SMA.

References:

Parsons C J, et al. Antifibrotic effects of a tissue inhibitor of metalloproteinase-1 antibody on established liver fibrosis in rats. *Hepatology* 40:1106-1115, 2004.

Rivera C A, et al. Attenuation of $CCl_4$-induced hepatic fibrosis by $GdCl_3$ treatment or dietary glycine. *Am J Physiol Gastrointest Liver Physiol* 281:G200-G207, 2001.

(iii) Liver Fibrosis, Bile Duct Ligation

Liver injury is induced in adult male rats by ligation of the common bile duct on Day 0.

Study Group 1

On study Day 1, serum concentrations for both SAP and CRP are determined. The ratio determined on Day 1 is used to calculate the dose of SAP needed to reach the target ratio defined in example 1. The calculated dose is administered every other day beginning on Day 2. Rats in the treated group are dosed intravenously via tail vein with SAP at a dose volume of 2-10 mL/kg. Untreated rats are dosed with 2-10 mL/kg of saline.

On Day 14, rats are sacrificed, body and liver weights are assessed, and liver tissue is harvested for analysis. Total collagen content is measured with the Sircol assay, and collagen deposition is measured with Masson trichrome, hematoxylin and eosin and Sirius red staining. Myofibroblast activation is determined by immunostaining for α-SMA.

Study Group 2: Adjustment of Dosage

On study Day 1 serum concentration for both SAP and CRP are determined. The ratio determined on Day 1 is used to calculate the dose of SAP needed to reach the target ratio defined in example 1. The calculated dose is administered on Day 2. On Day 3, serum concentration for both SAP and CRP are determined. The dosage is adjusted based on the concentrations determined on Day 2. On Day 4, the adjusted dosage is administered. These steps are repeated (measuring serum concentration on odd numbered days; administering adjusted dosage on even-numbered days). Rats in the treated group are dosed intravenously via tail vein with SAP at a dose volume of 2-10 mL/kg. Untreated rats are dosed with 2-10 mL/kg of saline.

On Day 14, rats are sacrificed, body and liver weights are assessed, and liver tissue is harvested for analysis. Total collagen content is measured with the Sircol assay, and collagen deposition is measured with Masson trichrome, hematoxylin and eosin and Sirius red staining. Myofibroblast activation is determined by immunostaining for α-SMA.

References:

Kisseleva T, et al. Bone marrow-derived fibrocytes participate in pathogenesis of liver fibrosis. *J Hepatology* 45:429-438, 2006.

Hellerbrand C, et al. Expression of intracellular adhesion molecule 1 by activated hepatic stellate cells. *Hepatology* 24:670-676, 1996.

Tramas E G, Symeonidis A. Morphologic and functional changes in the livers of rats after ligation and excision of the common bile duct. *Am J Pathol* 33:13-27, 1957.

(i) Unilateral Ureter Obstruction

Renal fibrosis is induced in adult male Sprague Dawley rats (5-7 weeks; 200 grams) by unilateral ureter obstruction. A piece of 4-0 silk suture is securely tied around the left ureter as close to the kidney as possible; the right kidney is used as an unobstructed control.

Study Group 1

On study Day 1 serum concentration for both SAP and CRP are determined. The ratio determined on Day 1 is used to calculate the dose of SAP needed to reach the target ratio defined in example 1. The calculated dose is administered on Days 2, 4, 6, 8, and 10. Rats in the treated group are dosed intravenously via tail vein with SAP at a dose volume of 2-10 mL/kg. Untreated rats are dosed with 2-10 mL/kg of saline.

Rats are sacrificed on day 7 or 14 and both the left and right kidneys are excised, weighed and fixed in formalin for histological examination. Tissue damage and fibrosis is evaluated by hematoxylin and eosin and Sirius red staining (Collagen) and immunohistochemistry for α-smooth muscle actin (α-SMA). Tissue fibrocytes are quantified by immunostaining for CD34+/CD45+ cells.

Study Group 2: Adjustment of Dosage

On study Day 1 serum concentration for both SAP and CRP are determined. The ratio determined on Day 1 is used to calculate the dose of SAP needed to reach the target ratio defined in example 1. The calculated dose is administered on Day 2. On Day 3, serum concentration for both SAP and CRP are determined. The dosage is adjusted based on the concentrations determined on Day 2. On Day 4, the adjusted dosage is administered. These steps are repeated (measuring serum concentration on odd numbered days; administering adjusted dosage on even-numbered days). Rats in the treated group are dosed intravenously via tail vein with SAP at a dose volume of 2-10 mL/kg. Untreated rats are dosed with 2-10 mL/kg of saline.

Rats are sacrificed on day 7 or 14 and both the left and right kidneys are excised, weighed and fixed in formalin for histological examination. Tissue damage and fibrosis is evaluated by hematoxylin and eosin and Sirius red staining (Collagen) and immunohistochemistry for α-smooth muscle actin (α-SMA). Tissue fibrocytes are quantified by immunostaining for CD34+/CD45+ cells.

References:

El Chaar M, Chen J, Seshan S V, Jha S, Richardson I, Ledbetter S R, Vaughan E D, Jr., Poppas D P, and Felsen D. Effect of combination therapy with enalapril and the TGF-beta antagonist 1D11 in unilateral ureteral obstruction. *Am J Physiol Renal Physiol* 292: F1291-1301, 2007.

Wu M J, Wen M C, Chiu Y T, Chiou Y Y, Shu K H, and Tang M J. Rapamycin attenuates unilateral ureteral obstruction-induced renal fibrosis. *Kidney Int* 69: 2029-2036, 2006.

Example 3: SAP/CRP Ratios in Human Cardiovascular Disease

In a recently published clinical study, circulating SAP concentrations were measured in patients with subclinical and clinical cardiovascular disease (CVD) in older adults from the Cardiovascular Health Study (CHS) (Jenny et al. 2007. Arterioscler Thromb Vasc Biol. 27: 352-358). In Cox regression models adjusted for age, sex, and ethnicity, a standard deviation increase in SAP was associated with angina and MI, but not stroke or CVD death. However, in this study determination of a ratio of SAP to CRP was not conducted. We conducted a prospective analysis of the data to determine the SAP/CRP ratio in each patient included in this study and then determined the association of this ratio with disease incidence (Table 2). There was a statistically significant association of lower SAP/CRP ratio relative to controls in patients with Stroke, CVD Death and all deaths. Importantly, these associations were not recognized in the original published study when SAP was analyzed on its own.

TABLE 2

|  | Mean (SD) SAP/CRP | P-value (vs. controls) | N |
|---|---|---|---|
| Controls | 24.83 (23.85) | — | 786 |
| Angina | 23.38 (22.47) | 0.074 | 523 |
| MI | 22.58 (22.32) | 0.176 | 308 |

TABLE 2-continued

|  | Mean (SD) SAP/CRP | P-value (vs. controls) | N |
|---|---|---|---|
| Stroke | 21.25 (20.08) | 0.026 | 323 |
| CVD Death | 18.83 (16.18) | <0.001 | 288 |
| All Death | 21.29 (20.49) | 0.007 | 685 |

Example 4: Determination of the Relative Binding of SAP and CRP for FcγRs

We characterized and compared the binding of various subtypes of Fcγ receptors to both SAP and CRP, determined the preference of each for SAP or CRP and rank ordered the specific Fcγ receptor subtypes for binding across both SAP and CRP. Our data represent the first set of biochemical binding analyses which characterize SAP binding to Fcγ receptors, compare SAP and CRP binding and provide information on the differences in their affinities for various Fcγ receptors. The results provide useful information toward understanding possible effects of a change in SAP/CRP ratio in plasma or serum.

We established methods for identifying and quantifying binding of the pentraxins SAP and CRP to Fcγ receptors using surface plasmon resonance technology. Surface plasmon resonance technology detects and quantifies binding and dissociation events between two proteins through a change in mass at the surface of a chip that is detected as a change in surface plasmon resonance. For these studies we used a Biacore X100 instrument.

SAP was bound to the surface of the test flow cell of a chip and a soluble recombinant form of Fcγ receptor (sFcγR) was flowed across the surface of the chip, representing the contact or binding phase. Buffer was then flowed across the chip surface, representing the dissociation phase. Change in mass at the cell surface with respect to time, detected as a change in surface plasmon resonance units (RUs) with time, was represented by a graph called a sensorgram. Binding of SAP to the CM5 dextran surface of a Biacore CM5 chip was performed in the presence of 10 mM Hepes, 150 mM NaCl, 0.5 mM $CaCl_2$, pH 7.4 as running buffer. Binding of SAP was stabilized by a very short immobilization using amine coupling (Biacore reagents) which covalently linked a limited representation of amine-group-containing amino acids on SAP to groups on the chip surface activated with 1-ethyl-3-(3-dimethylaminopropyl) carbodiimide and N-hydroxysuccinimide. A negative control flow cell was prepared using the same amine coupling procedure to immobilize human serum albumin to the same level as SAP. Any binding to this flow cell was considered non-specific binding and was subtracted from the test flow cell binding results. Soluble FcγR protein represented the extracellular region of the full-length membrane-bound form of the receptor, and possessed a poly-histidine tail of 6-10 histidines (SEQ ID NO: 11) at the C-terminus. Soluble FcγR at up to 5 different concentrations was flowed across the surface of both test and negative control flow cells of the Biacore chip, using running buffer containing 10 mM Hepes, 150 mM NaCl, 0.5 mM $CaCl_2$, pH 7.4. Surface plasmon resonance changes at the surface were used to evaluate binding kinetics of sFcγR binding to and dissociation from SAP. As well as subtracting any non-specific binding using the negative control flow cell binding results, minor test flow cell-specific fluctuations in signal were subtracted using the signal obtained from the test flow cell in the last of several buffer blank runs performed immediately prior to the test run. Association and dissociation rate constants, $K_a$ and $K_d$, respectively, were determined through kinetic fitting methods based on binding models and were used to define the kinetics of binding of sFcγR to SAP. The ratio $K_d/K_a$ was calculated and used to define the affinity ($K_D$) of binding between Fcγ receptor and SAP. Since we found that dissociation of sFcγRs from SAP was extremely slow and that, as a consequence of this tight binding, it was not possible to regenerate the chip surface and retain SAP activity in order to evaluate another binding event, we used single cycle kinetics methodology as defined by Biacore and the associated kinetics evaluation for this method. Evaluation applies algorithms that accommodate incomplete chip surface regeneration between cycles of different receptor concentration and allowed us to use 5 different receptor concentrations to obtain $K_a$, $K_d$ and $K_D$ from a single run.

Similar methods were used to evaluate binding interactions between CRP and sFcγRs, and details were the same except where stated here. Binding of CRP to Biacore CM5 chips was achieved through capture via PC-KLH (phosphocholine-keyhole limpet hemocyanin conjugate). Briefly, PC-KLH was immobilized onto a CM5 chip through amine coupling onto the chip surface activated with 1-ethyl-3-(3-dimethylaminopropyl)carbodiimide and N-hydroxysuccinimide. A negative control flow cell was prepared using the same amine coupling to immobilize human serum albumin to the same level as the PC-KLH. Binding of CRP to the PC moiety of PC-KLH immobilized on the CM5 chip was achieved by contacting the surface of the CM5 chip with the CRP in 10 mM Hepes, 150 mM NaCl, 0.5 mM $CaCl_2$, pH 7.4, to achieve the desired amount of bound CRP. We established that binding was specific for the PC moiety in PC-KLH, since no binding to KLH immobilized to the same level was evident when this was attempted on a different flow cell using the same conditions and the same 10 mM Hepes, 150 mM NaCl, 0.5 mM $CaCl_2$, pH 7.4, as running buffer. Binding of CRP to PC-KLH was stabilized by a very short immobilization using amine coupling. Since we found that dissociation of sFcγRs from CRP was relatively fast, it was possible to regenerate the chip surface completely during the dissociation phase in running buffer; "regenerated" CRP retained full activity in re-binding sFcγRs. For this reason we used multi-cycle kinetics methodology as defined by Biacore and the associated kinetics evaluation for this method, which applies algorithms that require complete chip surface regeneration between cycles of different receptor concentration. We used 5 different receptor concentrations to obtain $K_D$s from a single multicycle-evaluation.

Figure 4:
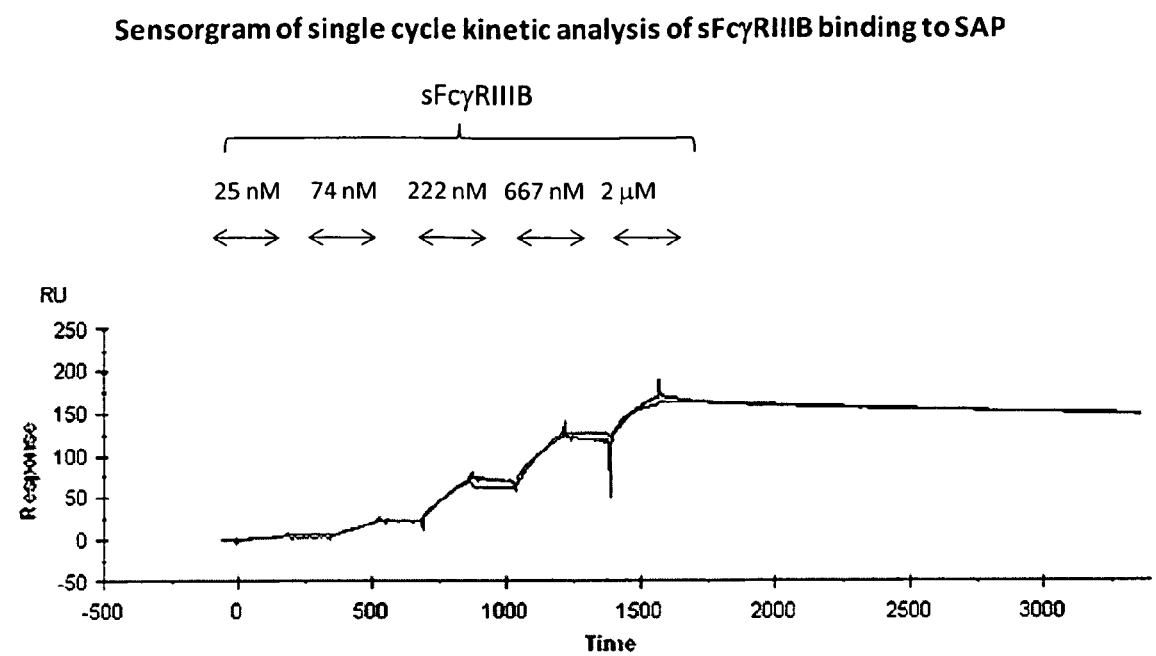
FIG. 4. SAP binding to sFcγRIIIB. The data is a representative sensorgram of SAP binding to sFcγRIIIB and indicates the association or contact phase and the dissociation phase at five different receptor concentrations. At the top of the graph are the indicated sFcγRIIIB concentrations with respect to time of delivery during the assay. The Y-axis of the chart represents the surface plasma resonance units (RUs), and the X-axis represents time. The data is graphed as the change in mass at the cell surface with respect to time.

We demonstrated that binding of SAP to the CM5 dextran on the chip surface was $Ca^{2+}$-dependent since no binding occurred in the absence of $Ca^{2+}$ and SAP bound in the presence of $Ca^{2+}$ could easily be removed with 10 mM EDTA. We found that SAP was able to bind FcγRI, FcγRIIA (H131 variant), and FcγRIIIB, but not FcγRIIB. Where binding occurred, on-rate (represented by $K_a$) was high, and off-rate (represented by $K_d$) was low. Table 3 shows the affinity ($K_D$) for each interaction, calculated as the ratio of $K_d/K_a$. The affinities of SAP for FcγRI, FcγRIIA (H131 variant), and FcγRIIIB are all high, relative to the normal range of affinities known in the art to represent affinities for protein/protein interactions, and are higher than those reported for IgG for FcγRIIA and FcγRIIIB, and in a similar range for IgG for FcγRI (Gessner J E, et al., Ann Hematol 76:231 (1998)). Therefore, although SAP can bind to most FcγRs with high affinity it will likely preferentially bind to the FcγR2A class of receptor. A representative sensorgram, of binding of SAP to FcγRIIIB, is shown in FIG. 4 and shows data for the association or contact phase and the dissociation phase at 5 different and sequentially delivered receptor concentrations.

TABLE 3

Affinities for sFcγR binding to SAP

| FcγR | KD(M) |
|---|---|
| FcγR1 | $5 \times 10^{-9}$ |
| FcγRIIA(H131) | $1.7 \times 10^{-10}$ |
| FcγRIIB | no binding |
| FcγRIIIB | $4 \times 10^{-10}$ |

We demonstrated that binding of CRP to the PC moiety of PC-KLH on the chip surface was $Ca^{2+}$-dependent since no binding occurred in the absence of $Ca^{2+}$ and CRP bound in the presence of $Ca^{2+}$ could easily be removed with 10 mM EDTA. We found that CRP was also able to bind FcγRI, FcγRIIA (H131 variant), and FcγRIIIB, but not FcγRIIB, and in this sense specificity for these different FcγRs was the same as for SAP. Where binding occurred, on-rate was high, and off-rate, in contrast to SAP, was also high and returned to baseline quickly. Qualitatively, we found a much lower affinity of CRP than SAP for any of these FcγR receptors, driven by the off-rate, predominantly. These data imply that SAP will effectively compete off CRP for binding to FcγRs unless the ratio of SAP/CRP is significantly reduced.

An additional feature of binding of FcγRs by CRP was also observed and considered relevant to CRP biology and the biology around SAP/CRP ratios: during the contact or association phase of the interaction analysis, actual mass of bound receptor decreased with time, implying that once receptor had bound, a change in conformation resulted that decreased the affinity for re-binding or initial binding of a receptor molecule to CRP during this phase. This effect increased with increased receptor concentration when the potential exists for increased occupancy by receptor of the binding site on more than one and up to 5 CRP protomers within the pentameric molecule. Representative sensorgrams are shown in FIG. 5(A) for FcγRI binding to CRP (bound to PC-KLH on a CM5 chip), and FIG. 5(B) for FcγRIIIB binding to CRP (bound to PC-KLH on a CM5 chip).

The existence of this effect prevented the application of standard methods to accurately quantify CRP binding to the sFcγRs. The effect is completely reversible however, since receptor can be completely dissociated (returned to baseline) and rebinding of an equivalent amount of receptor to the same degree is not affected, as seen with the duplicate analysis using 0.444 μM sFcγRI, for example. The fast on-rate of binding of FcγRI and FcγRIIIB to CRP enabled achievement of an almost steady state early in the contact phase and allowed us, nevertheless, to obtain an approximate read on affinity using only early association phase data. A representative plot of $R_{eq}$ (response at equilibrium) against receptor concentration is shown in FIG. 6(A) for binding of CRP to FcγRI and FIG. 6(B) for binding of CRP to FcγRIIIB.

Qualitatively it is clear that the affinities of CRP for FcγRI and FcγRIIIB are less than that of SAP since the curves by no means approach saturation at the surface ($R_{max}$ (maximum response reached at saturation) is theoretically reached at approximately $100 \times K_D$ or greater) yet many of the concentrations of receptor used exceeded $100 \times$ the $K_D$ of SAP for FcγRI or FcγRIIIB. The vertical line on each graph in FIG. 6 shows the approximate affinity ($K_D$) obtained, but this should be taken as an approximate indication of affinity only. Less total FcγRIIIB was able to bind to CRP on the same chip (FIG. 5(A)) when evaluated across the same concentration range as FcγRI, indicating lower affinity of FcγRIIIB for CRP, compared with FcγRI (FIG. 5(B)), even though on-rate was also rapid; this is supported by comparison of the plots (A and B) of $R_{eq}$ (response at equilibrium) against receptor concentration (FIG. 6). Considerably less FcγRIIA(H131) was able to bind to CRP on the same chip when it too was tested across the same concentration range, and again similar on-rates were seen. On a different chip, less total FcγRIIA(R131) was able to bind CRP than observed using the same concentration of FcγRI (same conditions). On this same chip, binding levels achieved for FcγRIIA(R131) and FcγRIIIB under the same conditions and concentrations were similar. Binding of FcγRIIA(R131) was dose-dependent. This implies that of the four FcγR receptors tested here which bind CRP, FcγRIIA(H131) has the lowest affinity; this is fitting with data reported in cell-based studies in the literature, which demonstrate that binding of CRP to FcγRIIA(H131) is of very low affinity and lower than that of CRP to FcγRIIA(R131) (Stein M-P et al., J. Clin. Invest. 105:369 (2000)).

The rank order of affinities for SAP and CRP binding to the FcγRs tested herein: FcγRIIA(H131)/SAP>FcγRIIIB/SAP>FcγRI/SAP >>FcγRI/CRP>FcγRIIIB/CRP~FcγRIIA (R131)>>FcγRIIA(H131)/CRP, with no binding of SAP or CRP detectable for FcγRIIB.

In comparing affinities of SAP and CRP for FcγRIIA (H131) and FcγRIIIB, it is evident that affinities of SAP are at least 1000-fold greater than those for CRP binding to FcγRIIA (H131) and FcγRIIIB. In human serum, SAP levels remain fairly constant, in the range 20-40 μg/ml or $1.5-3 \times 10^{-7}$ M. Affinities we obtained for SAP binding to FcγRIIA (H131) and FcγRIIIB are in the low $10^{-10}$ M range. Thus, SAP is able to bind these receptors to saturation in the absence of competing binding, and, within the context of our current understanding of SAP and CRP, binding to FcγRs, CRP would not be competitive at the normal plasma range of CRP levels. For FcγRI, the affinity of SAP is higher than that of CRP, but when CRP increases in the plasma where it can approach 1 mg/ml, it is likely that competition will occur. The lack of binding of SAP or CRP to FcγRIIB is relevant to the biology of both SAP and CRP since this is the only receptor that in its full-length transmembrane form in cells signals through an inhibitory ITIM signaling pathway thought to regulate the activating ITAM signaling mediated through FcγRs (Nimmerjahn F and Ravetch J V. Immunity 24:19 (2006)). Thus, in contrast to IgG signaling through FcγRs, SAP and CRP signaling through FcγRs appear not to be regulated by a balance of activating and inhibitory signaling receptors, but rather through the competitive binding of SAP and CRP for overlapping receptor pools.

Figure 7:
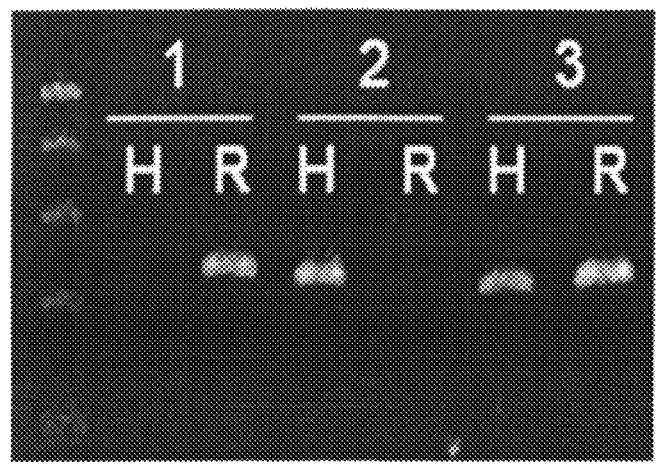
FIG. 7. PCR genotyping of the FcγRII allele. Genomic DNA was extracted from human PBMCs and genotyped using specific sense and antisense primers designed according to the different nucleotides in the second extracellular domain of FcγRII that produce a 253 bp product. Amplified PCR products were separated on 2% agrose gels. Group 1 represents the genotype of an R131 homozygous donor, group 2 represents the genotype of an H131 homozygous donor, and group 3 represents the genotype of an R131/H131 heterozygous donor.

Example 5: CRP-Mediated Enhancement of Fibrocyte Outgrowth is Dependent on the FcγRIIa-R131 Allele FcγRIIA Genotyping Genomic DNA was extracted from human PBMCs using Flexigene DNA extraction Kit (Qiagen, Valencia Calif.). For PCR genotyping, specific sense primers were designed according to the difference of the nucleotides in the second extracellular domain of FcγRII H131 and FcγRII H131, and the sense primers for genotyping are represented by SEQ ID NO: 8 and SEQ ID NO: 9, respectively. An antisense primer was designed according to the downstream intron sequence (SEQ ID NO: 10). This results in a 253 bp PCR fragment. Phusion High-fidelity PCR kit was purchased from New England Biolabs (Ipswich, A), and the PCR reaction solution contains 1× Phusion HF buffer, 10 mM dNTPs, 0.1 μg genomic DNA, 0.5 mM primer of each direction, and 0.5 μl DNA polymerase. The thermal cycles used were: 1 cycle 98° C. for 1 min., 30 cycles of 98° C. 10 for seconds, 60° C. for 20 seconds, and 72° C. for 15 seconds, 1 cycle of 72° C. for 5 min. The amplified PCR products were separated on 2% agrose gels FIG. 7. As showed in the figure, R/R (G/G) genotype only shows band in lane of R131 as sense primer, H/H (A/A) genotype only shows band in lane of H131 as sense primer, whereas H/R genotype shows bands in both lanes.

(1) Flesch B K, Bauer F, Neppert J. Rapid typing of the human Fc gamma receptor IIA polymorphism by polymerase chain reaction amplification with allele-specific primers. Transfusion. 1998, 38(2):174-6.

SAP and CRP activity in Fibrocyte Assay with Monocytes Expressing Different FcγR-IIa Polymorphisms.

Figure 8:
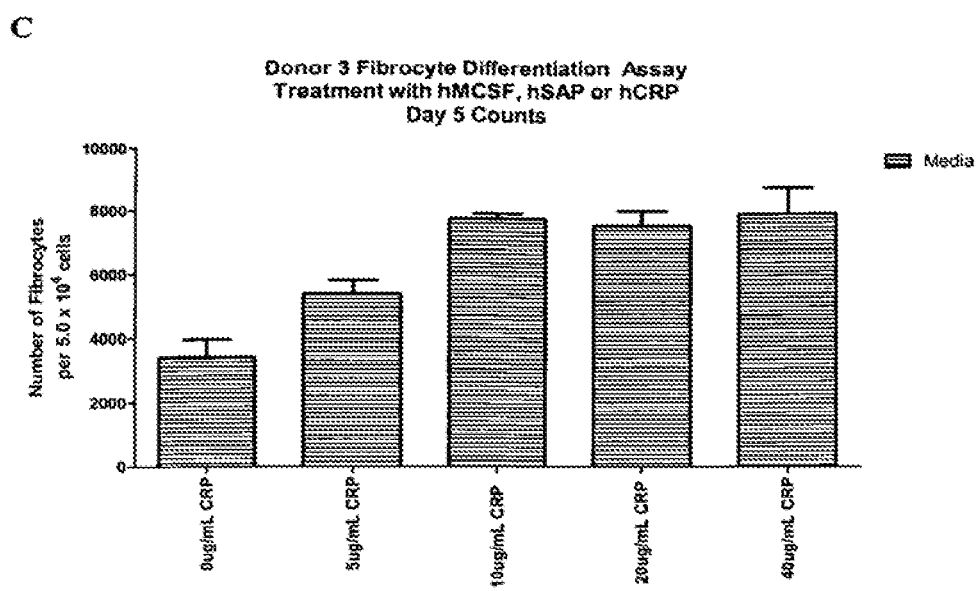
FIGS. 8A-C. (A) Fibrocyte differentiation assay with R131 homozygous donor monocytes. The X-axis indicates the concentration of CRP incubated with donor monocytes, which were suspended in media containing either 2 µg/mL or 1 µg/mL of SAP. The Y-axis indicates the amount of fibrocyte proliferation as measured by the enumeration of fibrocytes per $5.0 \times 10^4$ cells. (B) Fibrocyte differentiation assay with H131 homozygous donor monocytes. The X-axis indicates the concentration of CRP incubated with donor monocytes, which were suspended in media containing either 25 ng/mL hMCSF+2 µg/mL of hSAP or media-alone. The Y-axis indicates the amount of fibrocyte proliferation as measured by the enumeration of fibrocytes per $5.0 \times 10^4$ cells. (C) Fibrocyte differentiation assay with R131/H131 heterozygous donor monocytes. The X-axis indicates the concentration of CRP incubated with donor monocytes, which were suspended in media alone. The Y-axis indicates the amount of fibrocyte proliferation as measured by the enumeration of fibrocytes per $5.0 \times 10^4$ cells.

Fibrocyte assays were carried out as described in Example 1, using Donor 1 (R/R homozygous), Donor 2 (H/H homozygous), or Donor 3 (H/R heterozygous). Fibrocyte assays were carried out in the presence or absence of MCSF which increases the fibrocyte responsiveness of donor monocytes. As seen in FIG. 8A, Donor 1, R131/R131 homozygous, demonstrated the greatest CRP responsiveness at counteracting SAP's ability to inhibit fibrocyte differentiation. For Donor 1, only 5 ug/ml of CRP was necessary to counteract 1-2 ug/ml of SAP. Higher concentrations of CRP saturated the CRP receptors on this donor, leading to reduced crosslinking thereby negating its effects. These data correlate well with the reported higher binding activity of FcγRII-R131 for CRP. In contrast, Donor 2, H131/H131 homozygous, demonstrated the significantly reduced ability of CRP to counteract SAP's ability to inhibit fibrocyte differentiation FIG. 8B. For Donor 2, 40 ug/ml of CRP was necessary to counteract 2 ug/ml of SAP and had little impact on stimulating fibrocyte outgrowth in media without MCSF, consistent with the reduced ability of FcgRII-H131 to bind to CRP. Finally, Donor 3, R131/H131 heterozygous, demonstrated CRP-dependent and dose-responsive stimulation of fibrocyte differentiation in media without MCSF (FIG. 8C). These results are consistent with the polymorphism at FcgRII-131 playing a role in determining the relative impact SAP will have on CRP-driven fibrotic activity.

Sequence Listing

```
human serum amyloid protein P
                                                           SEQ ID NO: 1
HTDLSGKVFVFPRESVTDHVNLITPLEKPLQNFTLCFRAYSDLSRAYSLFSYNTQGRDNE
LLVYKERVGEYSLYIGRHKVTSKVIEKPPAPVHICVSWESSSGIAEFWINGTPLVKKGLR
QGYFVEAQPKIVLGQEQDSYGGKFDRSQSFVGEIGDLYMWDSVLPPENILSAYQGTPLP
ANILDWQALNYEIRGYVIIKPLVWV Gallus gallus serum amyloid protein P
                                                           SEQ ID NO: 2
QEDLYRKVFVFREDPSDAYVLLQVQLERPLLNFTVCLRSYTDLTRPHSLFSYATKAQDN
EILLFKPKPGEYRFYVGGKYVTFRVPENRGEWEHVCASWESGSGIAEFWLNGRPWPRK
GLQKGYEVGNEAVVMLGQEQDAYGGGFDVYNSFTGEMADVHLWDAGLSPDKMRSA
YLALRLPPAPLAWGRLRYEAKGDVVVKPRLREALGA Bos taurus serum amyloid protein P
                                                           SEQ ID NO: 3
QTDLRGKVFVFPRESSTDHVTLITKLEKPLKNLTLCLRAYSDLSRGYSLFSYNIHSKDNE
LLVFKNGIGEYSLYIGKTKVTVRATEKFPSPVHICTSWESSTGIAEFWINGKPLVKRGLKQ
GYAVGAHPKIVLGQEQDSYGGGFDKNQSFMGEIGDLYMWDSVLSPEEILLVYQGSSSIS
PTILDWQALKYEIKGYVIVKPMVWG Cricetulus migratorius serum amyloid protein P
                                                           SEQ ID NO: 4
QTDLTGKVFVFPRESESDYVKLIPRLEKPLENFTLCFRTYTDLSRPHSLFSYNTKNKDNEL
LIYKERMGEYGLYIENVGAIVRGVEEFASPVHFCTSWESSSGIADFWVNGIPWVKKGLK
KGYTVKTQPSIILGQEQDNYGGGFDKSQSFVGEMGDLNMWDSVLTPEEIKSVYEGSWL
EPNILDWRALNYEMSGYAVIRPRVWH Human FcγRIIA (NM_021642)
                                                           SEQ ID NO: 5
  1 gtctcttaaa acccactgga cgttggcaca gtgctgggat gactatggag acccaaatgt 61 ctcagaatgt atgtcccaga aacctgtggc tgcttcaacc attgacagtt ttgctgctgc 121 tggcttctgc agacagtcaa gctgctcccc caaaggctgt gctgaaactt gagccccgt 181 ggatcaacgt gctccaggag gactctgtga ctctgacatg ccaggggct cgcagccctg 241 agagcgactc cattcagtgg ttccacaatg ggaatctcat tcccacccac acgcagccca 301 gctacaggtt caaggccaac aacaatgaca gcggggagta cacgtgccag actggccaga 361 ccagcctcag cgaccctgtg catctgactg tgctttccga atggctggtg ctccagaccc 421 ctcacctgga gttccaggag ggagaaacca tcatgctgag gtgccacagc tggaaggaca 481 agcctctggt caaggtcaca ttcttccaga atggaaaatc ccagaaattc tcccatttgg 541 atcccacctt ctccatccca caagcaaacc acagtcacag tggtgattac cactgcacag
```

-continued
```
 601 gaaacatagg ctacacgctg ttctcatcca agcctgtgac catcactgtc caagtgccca
 661 gcatgggcag ctcttcacca atggggatca ttgtggctgt ggtcattgcg actgctgtag
 721 cagccattgt tgctgctgta gtggccttga tctactgcag gaaaaagcgg atttcagcca
 781 attccactga tcctgtgaag gctgcccaat ttgagccacc tggacgtcaa atgattgcca
 841 tcagaaagag acaacttgaa gaaccaaca atgactatga aacagctgac ggcggctaca
 901 tgactctgaa ccccagggca cctactgacg atgataaaaa catctacctg actcttcctc
 961 ccaacgacca tgtcaacagt aataactaaa gagtaacgtt atgccatgtg gtcatactct
1021 cagcttgctg agtggatgac aaaagaggg gaattgttaa aggaaaattt aaatggagac
1081 tggaaaaatc ctgagcaaac aaaaccacct ggcccttaga aatagcttta actttgctta
1141 aactacaaac acaagcaaaa cttcacgggg tcatactaca tacaagcata agcaaaactt
1201 aacttggatc atttctggta aatgcttatg ttagaaataa gacaacccca gccaatcaca
1261 agcagcctac taacatataa ttaggtgact agggactttc taagaagata cctaccccca
1321 aaaaacaatt atgtaattga aaaccaaccg attgccttta ttttgcttcc acatttcccc
1381 aataaatact tgcctgtgac attttgccac tggaacacta aacttcatga attgcgcctc
1441 agattttttcc tttaacatct tttttttttt tgacagagtc tcaatctgtt acccaggctg
1501 gagtgcagtg gtgctatctt ggctcactgc aaacccgcct cccaggttta gcgattctc
1561 atgcctcagc ctcccagtag ctgggattag aggcatgtgc catcatacc agctaatttt
1621 tgtatttttt atttttttt tttagtagag acagggtttc gcaatgttgg ccaggccgat
1681 ctcgaacttc tggcctctag cgatctgccc gcctcggcct cccaaagtgc tgggatgacc
1741 agcatcagcc ccaatgtcca gcctctttaa catcttcttt cctatgccct ctctgtggat
1801 ccctactgct ggtttctgcc ttctccatgc tgagaacaaa atcacctatt cactgcttat
1861 gcagtcggaa gctccagaag aacaaagagc ccaattacca gaaccacatt aagtctccat
1921 tgttttgcct tgggatttga gaagagaatt agagaggtga ggatctggta tttcctggac
1981 taaattcccc ttggggaaga cgaagggatg ctgcagttcc aaaagagaag gactcttcca
2041 gagtcatcta cctgagtccc aaagctccct gtcctgaaag ccacagacaa tatggtccca
2101 aatgactgac tgcaccttct gtgcctcagc cgttcttgac atcaagaatc ttctgttcca
2161 catccacaca gccaatacaa ttagtcaaac cactgttatt aacagatgta gcaacatgag
2221 aaacgcttat gttacaggtt acatgagagc aatcatgtaa gtctatatga cttcagaaat
2281 gttaaaatag actaacctct aacaacaaat taaaagtgat tgtttcaagg tgatgcaatt
2341 attgatgacc tatttattt ttctataatg atcatatatt acctttgtaa taaaacatta
2401 taaccaaaac a
```

H131/R131 allele is defined by the bold cat codon at positions 534-536 in the mRNA sequence, which encodes histidine at this position in the protein. When the second position (535) is not a, but is instead g, the codon becomes ctg and encodes the amino acid arginine.

Human FcγRIIA (NP_067674)

SEQ ID NO: 6

MTMETQMSQNVCPRNLWLLQPLTVLLLLASADSQAAPPKAVLKL
EPPWINVLQEDSVTLTCQGARSPESDSIQWFHNGNLIPTHTQPSYRFKAN
NNDSGEYTCQTGQTSLSDPVHLTVLSEWLVLQTPHLEFQEGETIMLRCHS
WKDKPLVKVTFFQNGKSQKFS<u>H</u>LDPTFSIPQANHSHSGDYHCTGNIGYTLF
SSKPVTITVQVPSMGSSSPMGIIVAVVIATAVAAIVAAVVALIYCRKKRI

SANSTDPVKAAQFEPPGRQMIAIRKRQLEETNNDYETADGGYMTLNPRAP
TDDDKNIYLTLPPNDHVNSNN
BOLD amino acids specify the signal sequence
<u>H</u> at position 166 is an R when the R131 polymorphism is present

SEQ ID NO: 7

Human FcγRIIA (SNP rs1801274)
gnl|dbSNP|rs1801274|allelePos = 301|totalLen = 601|taxid = 9606|snpclass = 1|alleles = 'C/T'|mol = Genomic|build = 129

```
TCCAAGCTCTGGCCCCTACTTGTTGGTCAATACTTAGCCAGGCTTCCACC
CCACTCCTCTTTGCTCCAGTGCCCAATTTTGCTGCTATGGGCTTTCTCAG
ACCTCCATGTAGGCCCATGTGACCTCAGCCCTTGTCCATCCCCTCTTCTC
CCCTCCCTACATCTTGGCAGACTCCCCATACCTTGGACAGTGATGGTCAC
```

-continued

```
AGGCTTGGATGAGAACAGCGTGTAGCCTATGTTTCCTGTGCAGTGGTAAT
CACCACTGTGACTGTGGTTTGCTTGTGGGATGGAGAAGGTGGGATCCAAA
Y
GGGAGAATTTCTGGGATTTTCCATTCTGGAAGAATGTGACCTTGACCAGA
GGCTTGTCCTTCCAGCTGTGGCACCTCAGCATGATGGTTTCTCCCTCCTG
GAACTCCAGGTGAGGGGTCTGGAGCACCAGCCATTCTGAAAGACACAAAT
ATGATAAGAAAAAGTTGTAAGGATAGATTCCAAGGGTTTTTCAGTCTCAG
AGGTACGTTACTCACAGAACTTGACATGATGTCTGGCAGACAGAAATGAA
GATGCTTCATGACAGATGTGAGCATTCTCTTATAGGCAATATATGGTATT
```

Y at position 301 indicates the C/T polymorphism

FCγRII H131
SEQ ID NO: 8
5'-ATCCCAGAAATTCTCCCA-3'

R131:
SEQ ID NO: 9
5'-ATCCCAGAAATTCTCCCG-3'

Antisense primer to downstream intron sequence
SEQ ID NO: 10
5'-CAATTTTGCTGCTATGGGC-3'

---

We claim:

1. A method for (i) reducing the severity of one or more symptoms of fibrosis or (ii) reducing the rate of progression or causing regression of fibrosis in a patient, the method comprising:
   (i) measuring the concentration of C reactive protein (CRP) and serum amyloid P (SAP) in a biological sample from said patient to determine an SAP-to-CRP ratio, wherein the biological sample is a fibrotic tissue, and wherein the concentration of CRP and SAP is measured as total concentration or free concentration of CRP or SAP protein;
   (ii) comparing the SAP-to-CRP ratio determined from step (i) with one or more reference SAP-to-CRP ratios determined from a biological sample from a healthy subject or determined from the mean ratio of a population of healthy subjects; and (iii) administering a CRP antagonist to said patient having an SAP-to-CRP ratio that is at least 10% lower than said one or more reference ratios, wherein the CRP antagonist is a full-length anti-CRP antibody or antigen-binding fragment thereof that binds to CRP and inhibits CRP interaction with an Fcγ receptor (FcγR), wherein the antigen-binding fragment comprises an Fab, Fv, scFV, Fab', or F(ab')$_2$ domain.

2. The method of claim 1, further comprising assaying a biological sample from said patient for the R131/H131 polymorphism of the FcγRIIA allele, comprising determining the amino acid residue at position 131 in both FcγRIIA alleles of said patient, wherein an SAP-to-CRP ratio that is at least 5% lower than one or more reference ratios is interpreted as an indication said patient is at risk for fibrosis when either or both said alleles of the patient are R131.

3. A method for adjusting the treatment plan to reduce the severity of one or more symptoms of fibrosis in a patient, the method comprising:

(i) measuring the concentration of C-reactive protein (CRP) and serum amyloid P (SAP) in a biological sample from said patient to determine the SAP-to-CRP ratio, wherein the biological sample is a fibrotic tissue, and wherein the concentration of CRP and SAP is measured as total concentration or free concentration of CRP or SAP protein;

(ii) comparing the determined SAP-to-CRP ratio with one or more reference CRP-to-SAP ratios determined from a biological sample from a healthy subject or determined from the mean ratio of a population of healthy subjects;

(iii) administering a CRP antagonist to said patient having an SAP-to-CRP ratio that is lower that said one or more reference ratios;

(iv) measuring the concentration of CRP and SAP in a biological sample from the patient to determine a second SAP-to-CRP ratio; and (v) adjusting the dosage or frequency of dosing of said CRP antagonists in order to achieve an SAP-to-CRP ratio greater than or equal to a target ratio for treating said fibrosis, and wherein the CRP antagonist is a full-length anti-CRP antibody or antigen-binding fragment thereof that binds to CRP and inhibits CRP interaction with an Fcγ receptor (FcγR), wherein the antigen-binding fragment comprises an Fab, Fv, scFV, Fab', or F(ab')2 domain.

4. The method of claim 3, wherein steps (iv) and (v) are repeated at least once, twice, or three or more times.

5. The method of claim 1, wherein the reference ratio is between about 5 to about 60.

6. The method of claim 1, wherein the concentrations of CRP and SAP measured are the free concentrations of CRP and SAP.

7. The method of claim 3, wherein the reference ratio is between about 5 to about 60.

8. The method of claim 3, wherein the concentrations of CRP and SAP measured are the free concentrations of CRP and SAP.

9. The method of claim 1, further comprising administering an SAP agonist, wherein the SAP agonist is a polypeptide comprising an amino acid sequence at least 95% identical to SEQ ID NO: 1.

10. The method of claim 3, further comprising administering an SAP agonist, wherein the SAP agonist is a polypeptide comprising an amino acid sequence at least 95% identical to SEQ ID NO: 1.

* * * * *

SEQUENCE LISTING

<160> NUMBER OF SEQ ID NOS: 11

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
<211> LENGTH: 208
<212> TYPE: PRT
<213> ORGANISM: Gallus gallus

<400> SEQUENCE: 2

Gln Glu Asp Leu Tyr Arg Lys Val Phe Val Phe Arg Glu Asp Pro Ser
1               5                   10                  15

Asp Ala Tyr Val Leu Leu Gln Val Gln Leu Glu Arg Pro Leu Leu Asn

```
                    20                  25                  30
Phe Thr Val Cys Leu Arg Ser Tyr Thr Asp Leu Thr Arg Pro His Ser
            35                  40                  45

Leu Phe Ser Tyr Ala Thr Lys Ala Gln Asp Asn Glu Ile Leu Leu Phe
        50                  55                  60

Lys Pro Lys Pro Gly Glu Tyr Arg Phe Tyr Val Gly Gly Lys Tyr Val
65                  70                  75                  80

Thr Phe Arg Val Pro Glu Asn Arg Gly Glu Trp Glu His Val Cys Ala
                85                  90                  95

Ser Trp Glu Ser Gly Ser Gly Ile Ala Glu Phe Trp Leu Asn Gly Arg
            100                 105                 110

Pro Trp Pro Arg Lys Gly Leu Gln Lys Gly Tyr Glu Val Gly Asn Glu
            115                 120                 125

Ala Val Val Met Leu Gly Gln Glu Gln Asp Ala Tyr Gly Gly Gly Phe
        130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
                165                 170                 175

Arg Leu Pro Pro Ala Pro Leu Ala Trp Gly Arg Leu Arg Tyr Glu Ala
            180                 185                 190

Lys Gly Asp Val Val Lys Pro Arg Leu Arg Glu Ala Leu Gly Ala
            195                 200                 205

<210> SEQ ID NO 3
<211> LENGTH: 205
<212> TYPE: PRT
<213> ORGANISM: Bos taurus

<400> SEQUENCE: 3

Gln Thr Asp Leu Arg Gly Lys Val Phe Val Phe Pro Arg Glu Ser Ser
1               5                   10                  15

Thr Asp His Val Thr Leu Ile Thr Lys Leu Glu Lys Pro Leu Lys Asn
            20                  25                  30

Leu Thr Leu Cys Leu Arg Ala Tyr Ser Asp Leu Ser Arg Gly Tyr Ser
        35                  40                  45

Leu Phe Ser Tyr Asn Ile His Ser Lys Asp Asn Glu Leu Leu Val Phe
    50                  55                  60

Lys Asn Gly Ile Gly Glu Tyr Ser Leu Tyr Ile Gly Lys Thr Lys Val
65                  70                  75                  80

Thr Val Arg Ala Thr Glu Lys Phe Pro Ser Pro Val His Ile Cys Thr
                85                  90                  95

Ser Trp Glu Ser Ser Thr Gly Ile Ala Glu Phe Trp Ile Asn Gly Lys
            100                 105                 110

Pro Leu Val Lys Arg Gly Leu Lys Gln Gly Tyr Ala Val Gly Ala His
            115                 120                 125

Pro Lys Ile Val Leu Gly Gln Glu Gln Asp Ser Tyr Gly Gly Gly Phe
        130                 135                 140

Asp Lys Asn Gln Ser Phe Met Gly Glu Ile Gly Asp Leu Tyr Met Trp
145                 150                 155                 160

Asp Ser Val Leu Ser Pro Glu Glu Ile Leu Leu Val Tyr Gln Gly Ser
                165                 170                 175

Ser Ser Ile Ser Pro Thr Ile Leu Asp Trp Gln Ala Leu Lys Tyr Glu
            180                 185                 190
```

```
Ile Lys Gly Tyr Val Ile Val Lys Pro Met Val Trp Gly
    195                 200                 205
```

```
<210> SEQ ID NO 4
<211> LENGTH: 204
<212> TYPE: PRT
<213> ORGANISM: Cricetulus migratorius

<400> SEQUENCE: 4
```

```
Gln Thr Asp Leu Thr Gly Lys Val Phe Val Phe Pro Arg Glu Ser Glu
1               5                   10                  15

Ser Asp Tyr Val Lys Leu Ile Pro Arg Leu Glu Lys Pro Leu Glu Asn
            20                  25                  30

Phe Thr Leu Cys Phe Arg Thr Tyr Thr Asp Leu Ser Arg Pro His Ser
        35                  40                  45

Leu Phe Ser Tyr Asn Thr Lys Asn Lys Asp Asn Glu Leu Leu Ile Tyr
    50                  55                  60

Lys Glu Arg Met Gly Glu Tyr Gly Leu Tyr Ile Glu Asn Val Gly Ala
65              70                  75                  80

Ile Val Arg Gly Val Glu Glu Phe Ala Ser Pro Val His Phe Cys Thr
                85                  90                  95

Ser Trp Glu Ser Ser Ser Gly Ile Ala Asp Phe Trp Val Asn Gly Ile
            100                 105                 110

Pro Trp Val Lys Lys Gly Leu Lys Lys Gly Tyr Thr Val Lys Thr Gln
        115                 120                 125

Pro Ser Ile Ile Leu Gly Gln Glu Gln Asp Asn Tyr Gly Gly Gly Phe
    130                 135                 140

Asp Lys Ser Gln Ser Phe Val Gly Glu Met Gly Asp Leu Asn Met Trp
145             150                 155                 160

Asp Ser Val Leu Thr Pro Glu Glu Ile Lys Ser Val Tyr Glu Gly Ser
                165                 170                 175

Trp Leu Glu Pro Asn Ile Leu Asp Trp Arg Ala Leu Asn Tyr Glu Met
            180                 185                 190

Ser Gly Tyr Ala Val Ile Arg Pro Arg Val Trp His
        195                 200
```

```
<210> SEQ ID NO 5
<211> LENGTH: 2411
<212> TYPE: DNA
<213> ORGANISM: Homo sapiens

<400> SEQUENCE: 5
```

```
gtctcttaaa acccactgga cgttggcaca gtgctgggat gactatggag acccaaatgt      60
ctcagaatgt atgtcccaga aacctgtggc tgcttcaacc attgacagtt ttgctgctgc     120
tggcttctgc agacagtcaa gctgctcccc caaaggctgt gctgaaactt gagccccgt      180
ggatcaacgt gctccaggag gactctgtga ctctgacatg ccaggggct cgcagccctg      240
agagcgactc cattcagtgg ttccacaatg gaatctcat tcccacccac acgcagccca     300
gctacaggtt caaggccaac aacaatgaca gcggggagta cacgtgccag actggccaga    360
ccagcctcag cgaccctgtg catctgactg tgctttccga atggctggtg ctccagaccc    420
ctcacctgga gttccaggag ggagaaacca tcatgctgag gtgccacagc tggaaggaca   480
agcctctggt caaggtcaca ttcttccaga atggaaaatc ccagaaattc tcccatttgg   540
atcccacctt ctccatccca caagcaaacc acagtcacag tggtgattac cactgcacag   600
gaaacatagg ctacacgctg ttctcatcca agcctgtgac catcactgtc caagtgccca   660
```

```
gcatgggcag ctcttcacca atggggatca ttgtggctgt ggtcattgcg actgctgtag    720
cagccattgt tgctgctgta gtggccttga tctactgcag gaaaaagcgg atttcagcca    780
attccactga tcctgtgaag gctgcccaat ttgagccacc tggacgtcaa atgattgcca    840
tcagaaagag acaacttgaa gaaaccaaca atgactatga aacagctgac ggcggctaca    900
tgactctgaa ccccagggca cctactgacg atgataaaaa catctacctg actcttcctc    960
ccaacgacca tgtcaacagt aataactaaa gagtaacgtt atgccatgtg gtcatactct   1020
cagcttgctg agtggatgac aaaaagaggg gaattgttaa aggaaaattt aaatggagac   1080
tggaaaaatc ctgagcaaac aaaaccacct ggcccttaga aatagcttta actttgctta   1140
aactacaaac acaagcaaaa cttcacgggg tcatactaca tacaagcata agcaaaactt   1200
aacttggatc atttctggta aatgcttatg ttagaaataa gacaacccca gccaatcaca   1260
agcagcctac taacatataa ttaggtgact agggactttc taagaagata cctacccccca   1320
aaaaacaatt atgtaattga aaaccaaccg attgccttta ttttgcttcc acattttccc   1380
aataaatact tgcctgtgac attttgccac tggaacacta aacttcatga attgcgcctc   1440
agatttttcc tttaacatct ttttttttt tgacagagtc tcaatctgtt acccaggctg   1500
gagtgcagtg gtgctatctt ggctcactgc aaacccgcct cccaggttta agcgattctc   1560
atgcctcagc ctcccagtag ctgggattag aggcatgtgc catcataccc agctaatttt   1620
tgtatttttt attttttttt tttagtagag acagggtttc gcaatgttgg ccaggccgat   1680
ctcgaacttc tggcctctag cgatctgccc gcctcggcct cccaaagtgc tgggatgacc   1740
agcatcagcc ccaatgtcca gcctctttaa catcttcttt cctatgccct ctctgtggat   1800
ccctactgct ggtttctgcc ttctccatgc tgagaacaaa atcacctatt cactgcttat   1860
gcagtcggaa gctccagaag aacaaagagc ccaattacca gaaccacatt aagtctccat   1920
tgttttgcct tgggatttga gaagagaatt agagaggtga ggatctggta tttcctggac   1980
taaattcccc ttggggaaga cgaagggatg ctgcagttcc aaaagagaag gactcttcca   2040
gagtcatcta cctgagtccc aaagctccct gtcctgaaag ccacagacaa tatggtccca   2100
aatgactgac tgcaccttct gtgcctcagc cgttcttgac atcaagaatc ttctgttcca   2160
catccacaca gccaatacaa ttagtcaaac cactgttatt aacagatgta gcaacatgag   2220
aaacgcttat gttacaggtt acatgagagc aatcatgtaa gtctatatga cttcagaaat   2280
gttaaaatag actaacctct aacaacaaat taaaagtgat tgtttcaagg tgatgcaatt   2340
attgatgacc tattttattt ttctataatg atcatatatt acctttgtaa taaaacatta   2400
taaccaaaac a                                                        2411
```

<210> SEQ ID NO 6
<211> LENGTH: 316
<212> TYPE: PRT
<213> ORGANISM: Homo sapiens

<400> SEQUENCE: 6

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
```

```
            50                  55                  60
Arg Ser Pro Glu Ser Asp Ser Ile Gln Trp Phe His Asn Gly Asn Leu
 65                  70                  75                  80

Ile Pro Thr His Thr Gln Pro Ser Tyr Arg Phe Lys Ala Asn Asn Asn
                 85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Ile Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 7
<211> LENGTH: 601
<212> TYPE: DNA
<213> ORGANISM: Homo sapiens

<400> SEQUENCE: 7
tccaagctct ggccccctact tgttggtcaa tacttagcca ggcttccacc ccactcctct     60
ttgctccagt gcccaatttt gctgctatgg gctttctcag acctccatgt aggcccatgt    120
gacctcagcc cttgtccatc ccctcttctc ccctccctac atcttggcag actccccata    180
ccttggacag tgatggtcac aggcttggat gagaacagcg tgtagcctat gtttcctgtg    240
cagtggtaat caccactgtg actgtggttt gcttgtggga tggagaaggt gggatccaaa    300
ygggagaatt tctgggattt ccattctgg aagaatgtga ccttgaccag aggcttgtcc    360
ttccagctgt ggcacctcag catgatggtt tctccctcct ggaactccag gtgaggggtc    420
tggagcacca gccattctga agacacaaa tatgataaga aaaagttgta aggatagatt    480
ccaagggttt ttcagtctca gaggtacgtt actcacagaa cttgacatga tgtctggcag    540
acagaaatga agatgcttca tgacagatgt gagcattctc ttataggcaa tatatggtat    600
t                                                                    601
```

```
<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atcccagaaa ttctccca                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcccagaaa ttctcccg                                                     18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caattttgct gctatgggc                                                    19

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 6-10 His residues

<400> SEQUENCE: 11

His His His His His His His His His His
1               5                   10
```